(12) United States Patent
Nakai et al.

(10) Patent No.: US 6,605,420 B2
(45) Date of Patent: Aug. 12, 2003

(54) PHOTOGRAPHIC PROCESSING COMPOSITION CONTAINING BISTRIAZINYL ARYLENEDIAMINE DERIVATIVE

(75) Inventors: Yasufumi Nakai, Kanagawa (JP); Keizo Kimura, Kanagawa (JP); Masashi Ogiyama, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/933,019

(22) Filed: Aug. 21, 2001

(65) Prior Publication Data
US 2002/0055071 A1 May 9, 2002

(30) Foreign Application Priority Data
Aug. 22, 2000 (JP) ...................... P.2000-251175

(51) Int. Cl.$^7$ .............. G03C 5/26; G03C 7/30; G03C 7/46
(52) U.S. Cl. ................ 430/486; 430/933
(58) Field of Search ............. 544/3; 430/486, 430/933

(56) References Cited

U.S. PATENT DOCUMENTS

| 3,649,288 A | * | 3/1972 | Shiba et al. | ................ 430/573 |
|---|---|---|---|---|
| 3,725,074 A | * | 4/1973 | Shiba et al. | ................ 430/570 |
| 3,887,380 A | * | 6/1975 | Shiba et al. | ................ 430/577 |
| 4,021,247 A | | 5/1977 | Hinata et al. | ............... 96/94 R |
| 5,395,742 A | | 3/1995 | Deguchi et al. | |
| 6,153,364 A | | 11/2000 | Goswami et al. | ........... 430/434 |
| 6,153,365 A | | 11/2000 | Goswami et al. | ........... 430/455 |
| 6,232,052 B1 | | 5/2001 | Goswami et al. | ........... 430/461 |
| 6,232,053 B1 | | 5/2001 | Goswami et al. | ........... 430/486 |

FOREIGN PATENT DOCUMENTS

| EP | 0 626 374 A2 | 11/1994 |
|---|---|---|
| JP | 6-329936 | * 11/1994 |
| JP | 6-332127 | * 12/1994 |

* cited by examiner

*Primary Examiner*—Hoa Van Le
(74) *Attorney, Agent, or Firm*—Sughrue Mion, PLLC

(57) ABSTRACT

A processing composition for silver halide photographic light-sensitive materials, comprises a bis[2,6-diaminotriazin-4-yl]arylenediamine derivative having at least one of a sulfonic acid group, a carboxylic group and a hydroxyl group within the molecule. This processing composition can be applied to a color developer, a bleaching agent, a fixing agent, a bleach-fixing agent and a stabilizing agent and also to a processing agent in a concentration on use, a concentrated processing agent and a solid processing agent.

13 Claims, No Drawings

PHOTOGRAPHIC PROCESSING COMPOSITION CONTAINING BISTRIAZINYL ARYLENEDIAMINE DERIVATIVE

BACKGROUND OF THE INVENTION

1. Field of the Invention

The present invention relates to a processing composition for silver halide color photographic light-sensitive materials, more specifically, the present invention relates to a composition having an excellent function of reducing staining ascribable to residual sensitizing dyes in the processed light-sensitive material.

2. Description of the Related Art

With remarkable progress of digital camera and color printer, the processing of a silver halide color photographic light-sensitive material is demanded to quickly provide a high-quality image to users. However, since mere shortening of the processing time in conventional methods results in the completion of processing before sensitizing dyes in the light-sensitive material are thoroughly washed out, the highlight part or background part in the white portion of a color print is colored by a large amount of residual sensitizing dyes and the product cannot endure the viewing. In the case of a color negative film, the density in the minimum density part increases, whereby the color balance is lost and an appropriate print cannot be provided.

In recent years, use of silver halide tabular grains is an important basic technique in the preparation of a high-sensitivity light-sensitive material for photographing. This technique is advantageous in that since the amount of sensitizing dyes used per unit volume can be increased, the sensitivity and the sensitivity-graininess ratio are improved, but it has a problem that the amount of sensitizing dyes remaining in the processed light-sensitive material increases. Depending on the processing conditions, the increase in the amount of residual sensitizing dyes cannot be ignored and this causes a phenomenon such as lost of color balance due to increase in the density in the minimum density part of a color negative film or coloration of the highlight part of a color reversal film.

*Research Disclosure*, No. 20733 discloses a method of using a bistriazinylaminostilbene disulfonic acid compound as one example of the method for removing the residual color ascribable to sensitizing dyes. This method is widely used in the processing of color photographic light-sensitive materials. JP-A-6-329936 (the term "JP-A" as used herein means an "unexamined published patent application") also discloses a bistriazinylaminostilbene disulfonic acid compound having excellent solubility and capable of reducing the residual color even in the processing shortened in the processing time.

Along with this quick processing of a photographic light-sensitive material, it is also demanded to reduce or maximally recycle the waste containers of processing agents or to more concentrate the processing compositions so as to reduce the cost for transportation or storage of the processing agents or processing chemicals. Accordingly, the additives used for the purpose of reducing the residual color must be suited for this concentration. However, a compound having an effect of reducing the residual color and capable of stably dissolving even in the state concentrated to a high salt concentration and satisfactorily providing the effect even in the processing reduced in the processing time has not yet been found out.

SUMMARY OF THE INVENTION

An object of the present invention is to solve the above-described problems in the techniques of the related art and provide a processing composition for silver halide color photographic light-sensitive materials, which can reduce the staining ascribable to the residual sensitizing dyes in the processed light-sensitive material and can be free of deposition of precipitates during the low-temperature storage of the processing composition.

The object of the present invention can be attained by the following inventions.

(1) A processing composition for silver halide photographic light-sensitive materials, comprising a compound represented by the following formula (I):

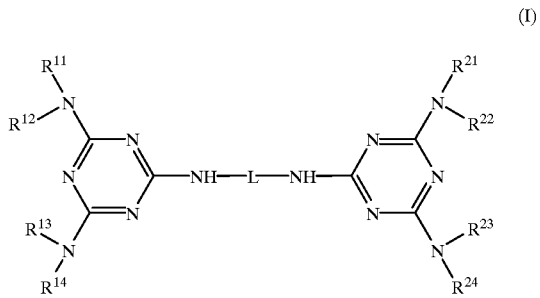

wherein $R^{11}$, $R^{12}$, $R^{13}$, $R^{14}$, $R^{21}$, $R^{22}$, $R^{23}$ and $R^{24}$ each represents a hydrogen atom, an alkyl group, an aryl group or a heterocyclic group, L represents a phenylene group or a naphthylene group, and the pairs $R^{11}$ and $R^{12}$, $R^{13}$ and $R^{14}$, $R^{21}$ and $R^{22}$, and $R^{23}$ and $R^{24}$ each may be combined with each other to form a ring, provided that at least one group represented by —$SO_3K$, —$CO_2M$ or —OH (wherein M represents a hydrogen atom, an alkali metal, an alkaline earth metal, ammonium or pyridinium) is contained within the molecule, that the case where three or more of $R^{11}$, $R^{12}$, $R^{13}$, $R^{14}$, $R^{21}$, $R^{22}$, $R^{23}$ and $R^{24}$ $R^{11}$, $R^{12}$, $R^{13}$, $R^{14}$, $R^{21}$, $R^{22}$, $R^{23}$ and $R^{24}$ are an aryl group and the case where at least one of $R^{11}$, $R^{12}$, $R^{13}$ and $R^{14}$ and at least one of $R^{21}$, $R^{22}$, $R^{23}$ and $R^{24}$ are combined with each other to form a ring are excluded, and that a group represented by —N=N—0 is not contained within the molecule (2) An image formation method comprising using the processing composition for silver halide photographic light-sensitive materials described in (1).

(3) A compound represented by the following formula (I):

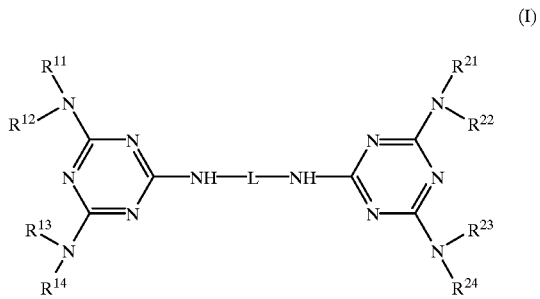

wherein $R^{11}$, $R^{12}$, $R^{13}$, $R^{14}$, $R^{21}$, $R^{22}$, $R^{23}$ and $R^{24}$ each represents a hydrogen atom, an alkyl group, an aryl group or a heterocyclic group, L represents a phenylene group or a naphthylene group, and the pairs $R^{11}$ and $R^{12}$, $R^{13}$ and $R^{14}$, $R^{21}$ and $R^{22}$, and $R^{23}$ and $R^{24}$ each may be combined with each other to form a ring, provided that at least one group represented by —$SO_3M$, —$CO_2M$ or —OH (wherein X represents a hydrogen atom, an alkali metal, an alkaline earth metal, ammonium or pyridinium) is contained within the molecule, that the case where three or more of $R^{11}$, $R^{12}$, $R^{13}$, $R^{14}$, $R^{21}$, $R^{22}$, $R^{23}$ and $R^{24}$ are an aryl group and the case where at least one of $R^{11}$, $R^{12}$, $R^{13}$ and $R^{14}$ and at least one of $R^{21}$, $R^{22}$, $R^{23}$ and $R^{24}$ are combined with each other to form a ring are excluded, and that a group represented by —N═N—O is not contained within the molecule.

The above-described compound of the present invention not only affords the means for attaining the object of the present invention but also has the following excellent properties. The compound of the present invention does not emit fluorescence and therefore, when used in combination with a bis(triazinylamino)stilbene disulfonic acid compound in the processing of a color print material, the fluorescent brightness and reduction in staining ascribable to sensitizing dyes can be independently controlled. Accordingly, the compound of the present invention can be preferably used in the processing of a color negative film or a color reversal film, where the processed light-sensitive material is not required to have fluorescent brightness. Furthermore, since the compound of the present invention is highly stable in the bleach-fixing composition or fixing composition as compared with the bis(triazinylamino)stilbene disulfonic acid compound and free of any deterioration in aging, so that stable processing performance can be maintained irrelevantly to the fluctuation in the processing amount per day or processing operation conditions.

DETAILED DESCRIPTION OF THE INVENTION

The compound of formula (I) is described in detail below. The alkyl group represented by $R^{11}$, $R^{12}$, $R^{13}$, $R^{14}$, $R^{21}$, $R^{22}$, $R^{23}$ and $R^{24}$ is a substituted or unsubstituted alkyl group hating from 1 to 20, preferably from 1 to 8, more preferably from 1 to 4 carbon atoms and examples thereof include a methyl group, an ethyl group, an i-propyl group, an n-propyl group, an n-octyl group, a sulfomethyl group, a 2-hydroxyethyl group, a 3-hydroxpropyl group, a 2-hydroxypropyl group, a 2-sulfoethyl group, a 2-methoxyethyl group, a 2-(2-hydroxyethoxy)ethyl group, a 2-[2-(2-hydroxyethoxy)ethoxy]ethyl group, a 2-(2-[2-(2-hydroxyethoxy)ethoxy]ethyl group, a 2,3-dihydroxypropyl group, a 3,4-dihydroxybutyl group and 2,3,4,5,6-pentahydroxyhexyl group.

The aryl group represented by $R^{11}$, $R^{12}$, $R^{13}$, $R^{14}$, $R^{21}$, $R^{22}$, $R^{23}$ and $R^{24}$ is a substituted or unsubstituted aryl group having from 6 to 20, preferably from 6 to 10, more preferably from 6 to 8 carbon atoms and examples thereof include a phenyl group, a naphthyl group, a 3-carboxyphenyl group, a 4-carboxyphenyl group, a 3,5-dicarboxyphenyl group, a 4-methoxyphenyl group, a 2-sulfophenyl group and a 4-sulfophenyl group. The heterocyclic group represented by $R^{11}$, $R^{12}$, $R^{13}$, $R^{14}$, $R^{21}$, $R^{22}$, $R^{23}$ and $R^{24}$ is a monovalent group resulting from excluding one hydrogen atom from a substituted or unsubstituted 5- or 6-membered aromatic or nonaromatic heterocyclic compound having from 2 to 20, preferably from 2 to 10, more preferably from 3 to 8 carbon atoms and examples thereof include a 2-furyl group, a 2-thienyl group, a 2-pyrimidinyl group and a 2-benzothiazolyl group.

$R^{11}$, $R^{12}$, $R^{13}$, $R^{14}$ $R^{21}$, $R^{22}$, $R^{23}$ and $R^{24}$ each is preferably a hydrogen atom, an alkyl group or an aryl group, more preferably a hydrogen atom, a methyl group, an ethyl group, an n-propyl group, a sulfomethyl group, a 2-hydroxyethyl group, a 3-hydroxypropyl group, a 2-hydroxypropyl group, a 2-sulfoethyl group, a 2-methoxyethyl group, 2-(2-hydroxyethoxy)ethyl group, a 2-[2-(2-hydroxyethoxy)ethoxy]ethyl group, a 2,3-dihydroxypropyl group, a 3,4-dihydroxybutyl group, a phenyl group, a 3-carboxyphenyl group, a 4-carboxyphenyl group, a 3,5-dicarboxyphenyl group, a 4-methoxyphenyl group, a 2-sulfophenyl group or a 4-sulfophenyl group, still more preferably a hydrogen atom, a methyl group, an ethyl group, a sulfomethyl group, a 2-hydroxyethyl group, a 2-sulfoethyl group, a 2-(2-hydroxyethoxy)ethyl group, a 2,3-dihydroxypropyl group, a phenyl group, a 3-carboxyphenyl group, a 4-carboxyphenyl group, a 2-sulfophenyl group or a 4-sulfophenyl group, particularly preferably a hydrogen atom, a methyl group, a sulfomethyl group, a 2-hydroxyethyl group, a 2-sulfoethyl group, a 2-(2-hydroxyethoxy)ethyl group, a 2,3-dihydroxypropyl group, a phenyl group or a 4-sulfophenyl group.

The phenylene group or naphthylene group represented by L is a substituted or unsubstituted phenylene or naphthylene group having from 6 to 20, preferably from 6 to 15, more preferably from 6 to 11 carbon atoms and examples thereof include 1,4-phenylene, 1,3-phenylene, 1,2phenylene, 1,5-naphthylene, 1,8-naphthylene, 4-carboxy-1,2-phenylene, 5-carboxy-1,3-phenylene, 3-sulfo-1,4-phenylene, 5-sulfo-1,3-phenylene, 2,5-dimethoxy-1,4-phenylene and 2,6-dichloro-1,4-phenylene.

L is preferably 1,4-phenylene, 1,3-phenylene, 1,2-phenylene, 1,5-naphthylene, 5-carboxy-1,3-phenylene or 5-sulfo-1,3-phenylene, more preferably 1,4-phenylene or 1,3-phenylene.

The ring formed by each pair $R^{11}$ and $R^{12}$, $R^{13}$ and $R^{14}$, $R^{21}$ and $R^{22}$, or $R^{23}$ and $R^{24}$ combined with each other is preferably a 5- or 6-membered ring. Examples of the ring include a pyrrolidine ring, a piperidine ring, a piperazine ring and a morpholine ring.

Among alkali metals and alkaline earth metals represented by M, preferred are Na and K. Examples of the ammonium group include an ammonium group, a triethylammonium group and a tetrabutylammoninm group. M is most preferably Na of K.

The compound of the present invention may contains at least one group represented by —$SO_3M$, —$CO_2M$ or —OH in the molecule, at the terminal of $R_{11}$, $R_{12}$, $R_{13}$, $R_{14}$, $R_{21}$, $R_{22}$, $R_{23}$ or $R_{24}$, or on the phenylene or naphthylene group of L.

Specific examples of the compound of the present invention are set forth below, however, the present invention is not limited thereto.

A-1)

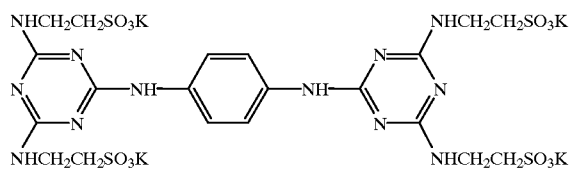

A-2)

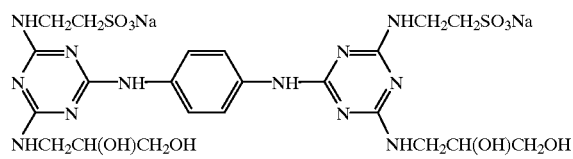

-continued
A-3)
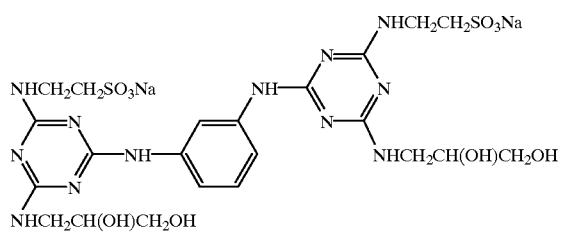
A-4)
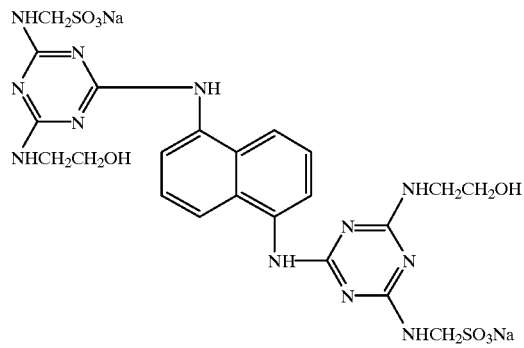
A-5)
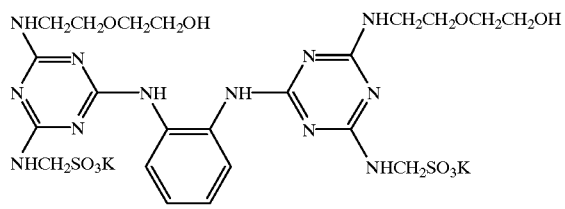
A-6)
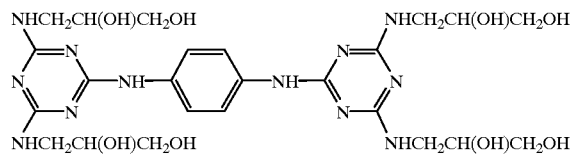
A-7)
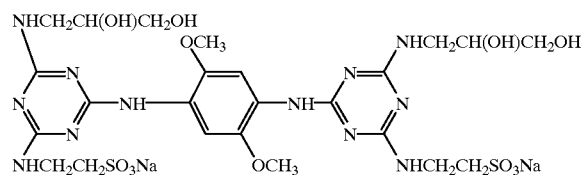
A-8)
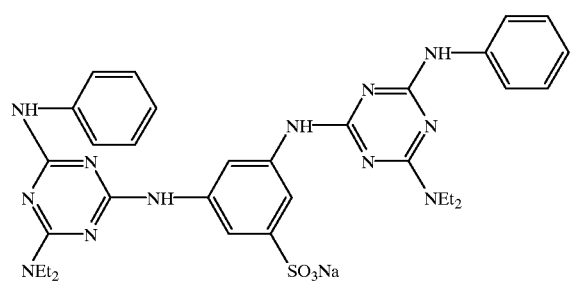
A-9)
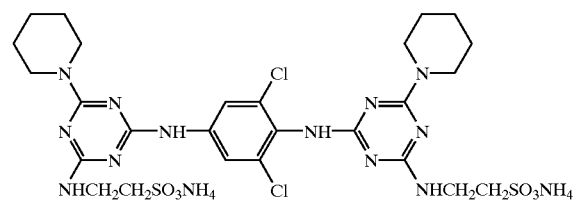
A-10)
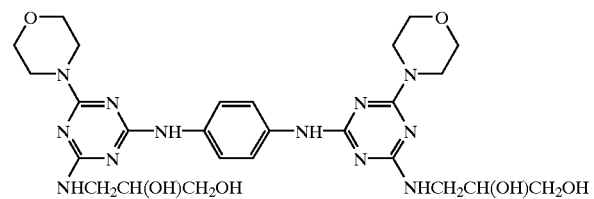
A-11)
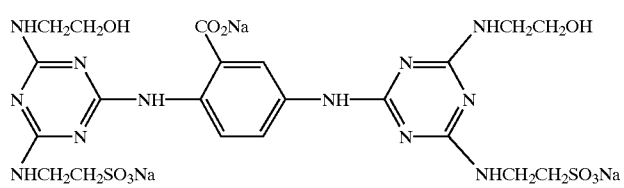
A-12)
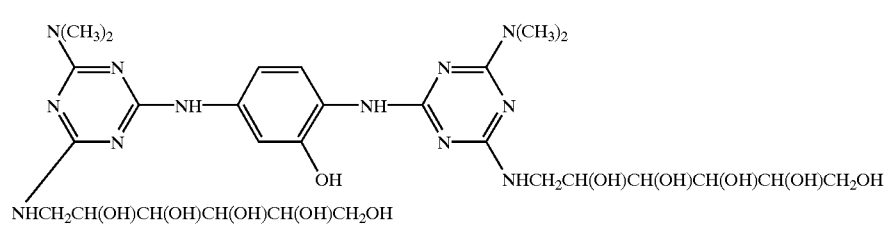

-continued
A-13)
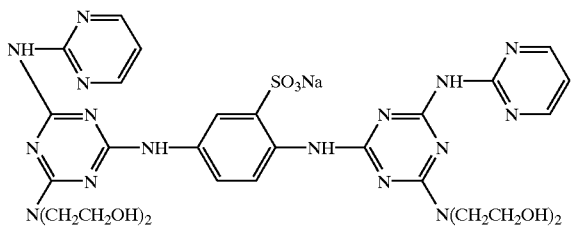
A-14)
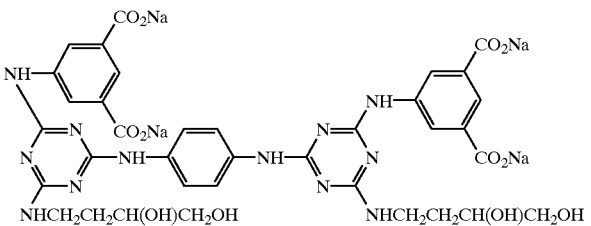
A-15)
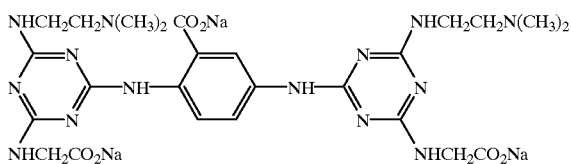
A-16)
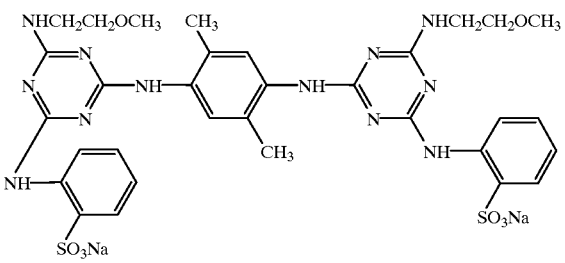
A-17)
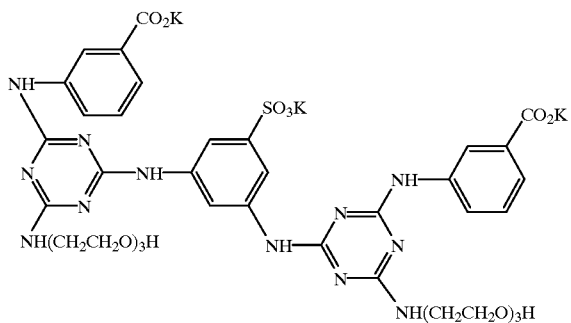
A-18)
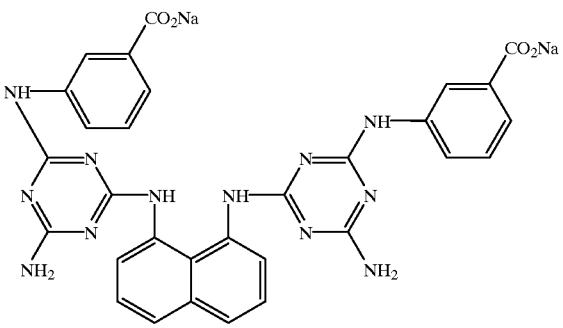
A-19)
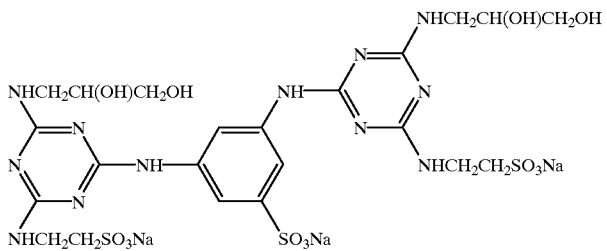
A-20)
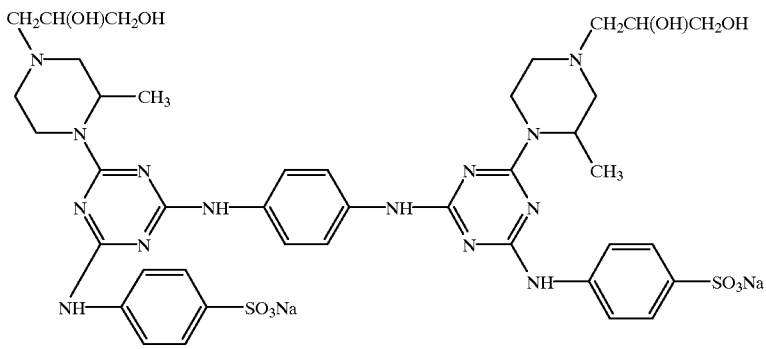

-continued
A-21)
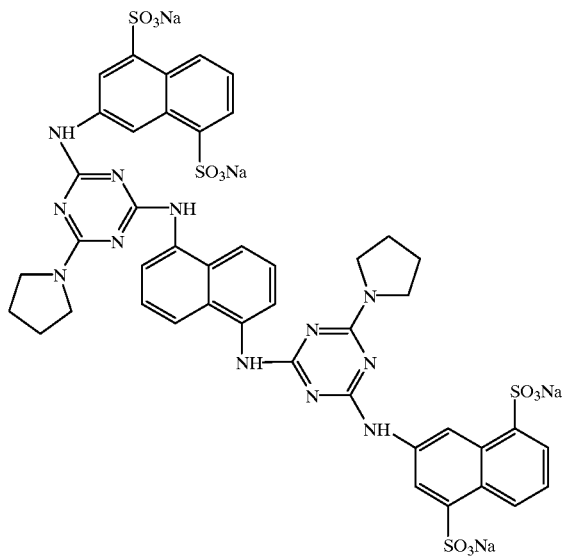
A-22)
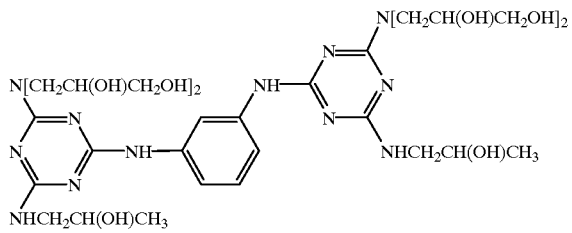
A-23)
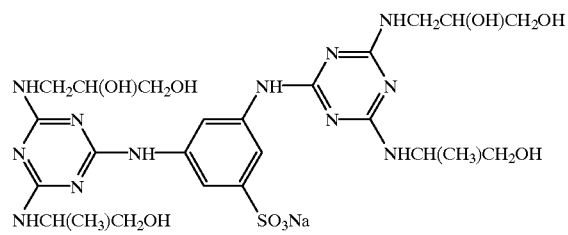
A-24)
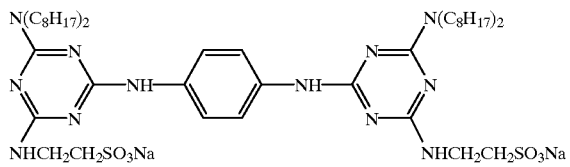
A-25)
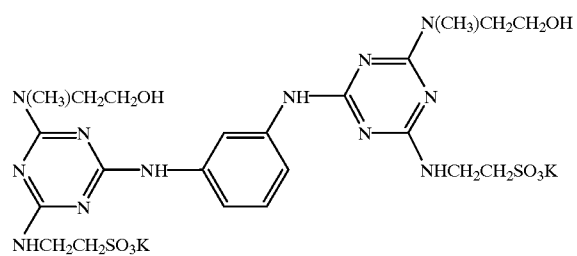
A-26)
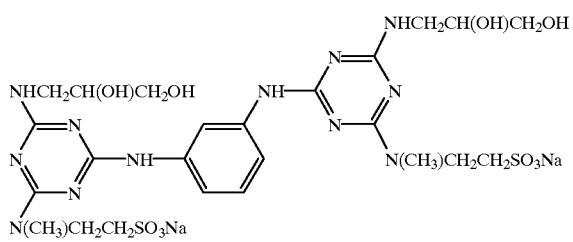
A-27)
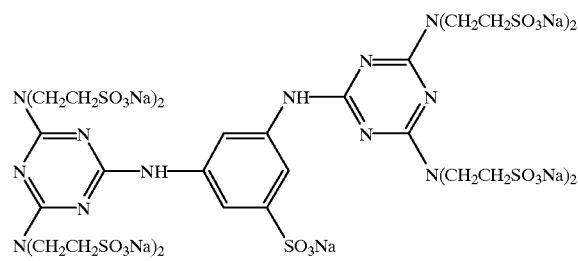
A-28)
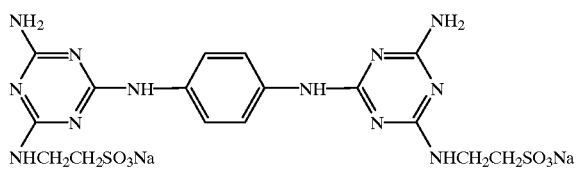

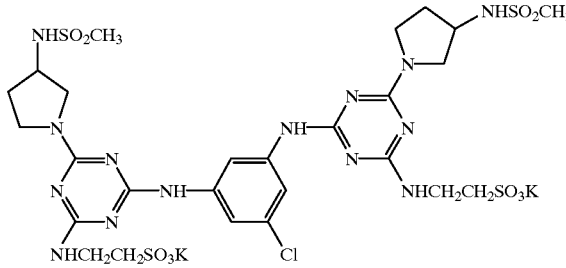
A-29)

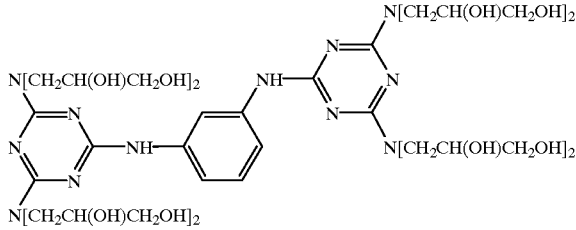
A-30)

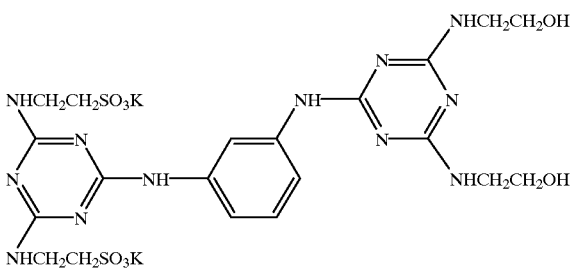
A-31)

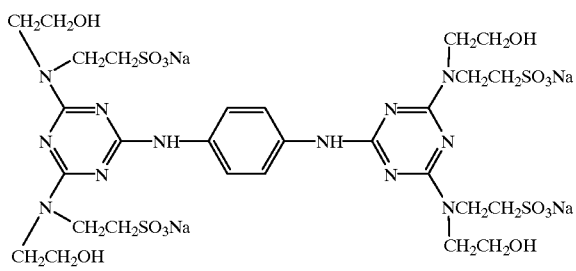
A-32)

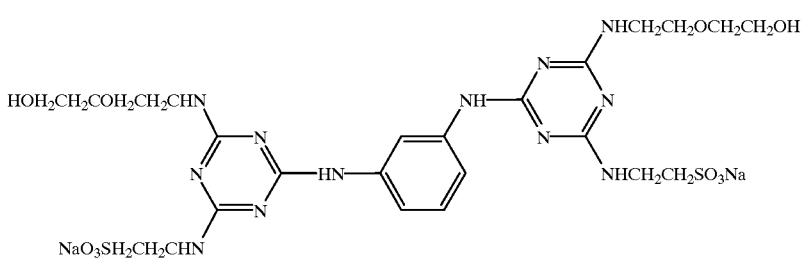
A-33)

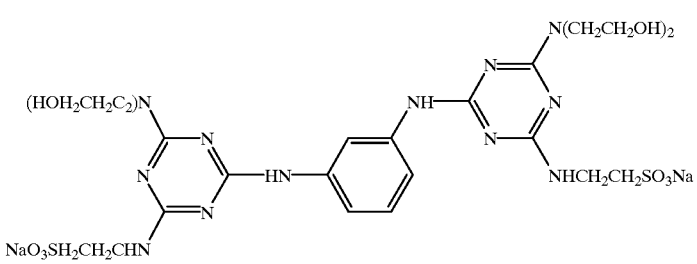
A-34)

The compound represented by formula (I) can be synthesized by referring, for example, to Hirotsugu Matsui, *Yuki Gosei Kagaku Kyokai Shi* (*Journal of Organic Synthetic Chemistry Association*), Vol. 17, page 528 (1959) and Japanese Patent No. 2,618,748. More specifically, a method of reacting cyanuric chloride with a phenylenediamine derivative or a naphthalenediamine derivative and subsequently with an amine is preferred. A method of reacting the phenylenediamine derivative or naphthalenediamine derivative through two stages or at the final stage is also preferred. Examples of the solvent used for this reaction include water and organic solvents such as alcohols, ketones, ethers and amides. Among these, water and water-soluble organic solvents are preferred. A mixed solvent thereof may also be used and among the mixed solvents, a mixed solvent of water and acetone is most preferred. Examples of the base used include organic bases such as triethylamine, pyridine and 1,8-diazabicyclo[5,4,0]-7-undecene, and inorganic bases such as sodium hydroxide, potassium hydroxide, sodium carbonate, potassium carbonate, sodium hydrogencarbonate and potassium hydrogencarbonate. Among these, inorganic bases are preferred and in particular, sodium hydroxide, potassium hydroxide, sodium carbonate and potassium carbonate are more preferred. The reaction temperature is from −20 to 150° C., preferably from −10 to 100° C. To speak more specifically, the reaction temperature is preferably −10 to 10° C. at the first stage, from 0 to 40° C. at the second stage and from 40 to 100° C. at the third stage.

SYNTHESIS EXAMPLE 1

Compound (A-2) of the present invention was synthesized through the synthesis reaction route shown below.

Compound (A-2)

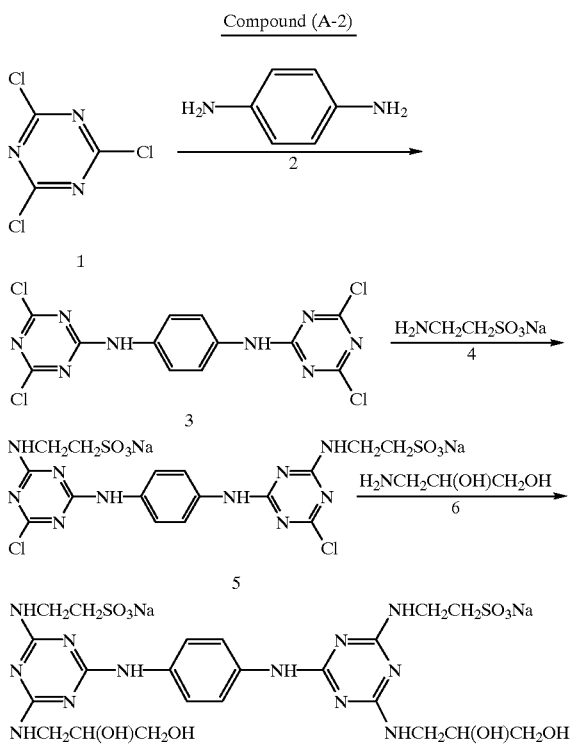

Synthesis of Compound 3

Into a three-neck flask, 37.6 g of Compound (1) and 280 ml of acetone were charged and while stirring in an ice-acetone bath, a solution containing 10.8 g of Compound (2) and 10 ml of acetone was added dropwise over 10 minutes while keeping the inner temperature at −7 to 2° C. After the completion of dropwise addition, a solution containing 10.6 g of sodium carbonate and 100 ml of water was added dropwise over 10 minutes. At this time, the inner temperature was from 2 to 7° C. After the completion of dropwise addition, the ice-acetone bath was removed and stirring was continued for 30 minutes. The precipitated crystals were suction-filtered to obtain the objective Compound (3) as a crude product. This product was intactly used in the next step.

Synthesis of Compound 5

Into a three-neck flask, 25.0 g of Compound (4) and 250 ml of water were charged and while stirring, 21.2 g of sodium carbonate was added and dissolved. Subsequently, Compound (3) obtained above was added and the mixture was stirred at an inner temperature of 85° C. for 5 hours. After the completion of stirring, the reaction solution was cooled to room temperature and the precipitated crystals were suction-filtered to obtain the objective Compound (5) as a crude product. This product was intactly used in the next step.

Synthesis of Compound A-2

Into a three-neck flask, Compound (5), 45.6 g of compound (5) and 200 ml of water were charged and the mixture was stirred at an inner temperature of 85° C. for 10 hours. The reaction mixture was concentrated by a rotary evaporator and thereto, 500 ml of ethanol was added. The obtained crystals were suction-filtered to obtain 111.2 g of the objective Compound A-2. The purity of this compound was examined by liquid chromatography and found to be 64.5% (yield: 98%). The conditions for the liquid chromatography were as follows.

Column: TSK-gel ODS-80 TM (produced by Tosoh Corp.)

Eluent:
Solution A: obtained by adding 20 ml of PIC A reagent solution (produced by Waters) to 1 liter of water
Solution B: obtained by adding 20 ml of PIC A reagent solution (produced by Waters) to a mixed solution containing 800 ml of methanol and 200 ml of water.
Solution A/Solution B: changed in accordance with a gradient from 50/50 (0 min) to 0/100 (35 min)
Detection wavelength: 254 nm The purity was determined by the peak area recorded on a chart under the above-described conditions.

SYNTHESIS EXAMPLE 2

Compound (A-3) of the present invention was synthesized through the synthesis reaction route shown below.

Compound (A-3)

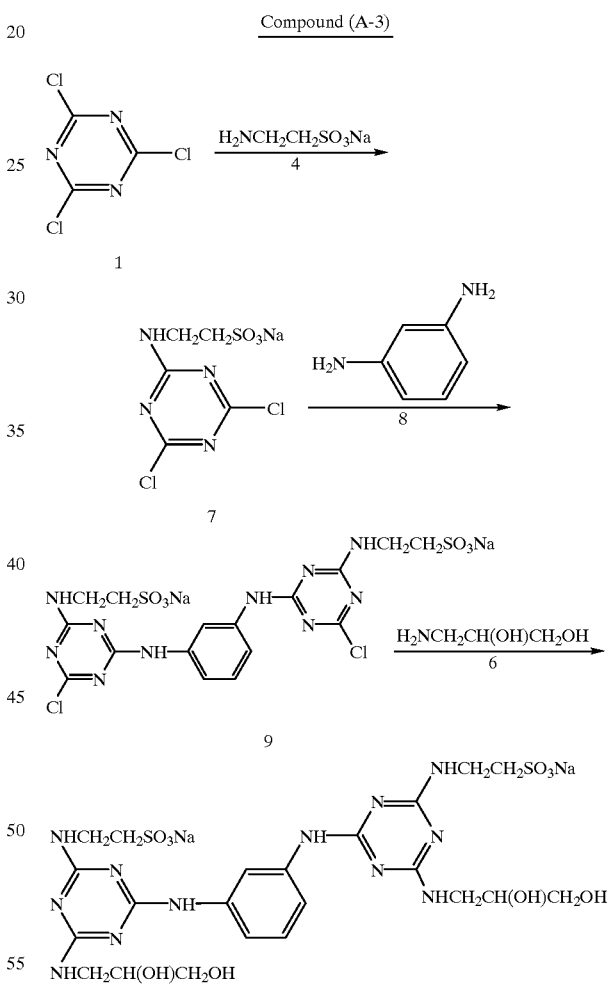

Synthesis of Compound 9

Into a three-neck flask, 37.6 g of Compound (1) and 280 ml of acetone were charged and the mixture was stirred in an ice-acetone bath. Thereto, a solution containing 25.0 g of Compound (4), 21.2 g of sodium carbonate and 250 ml of water was added dropwise over 15 minutes at an inner temperature of −7 to −2° C. After the completion of dropwise addition, the ice-acetone bath was removed and stirring was continued in an ice-cooling bath for 30 minutes. Thereto, a solution obtained by dissolving 10.8 g of Compound (8) in 100 ml of acetone was added dropwise over 10 minutes and subsequently, a solution obtained by dissolving 10.6 g of sodium carbonate in 30 ml of water was added dropwise over 5 minutes. Thereafter, the ice bath was removed and stirring was continued for 3 hours. The precipitated crystals were suction-filtered to obtain the objective Compound (9) as a crude product. This product was intactly used in the next step.

Synthesis of Compound A-3

Into a three-neck flask, Compound (9) obtained above, 45.6 g of Compound (6) and 200 ml of water were charged and after stirring at an inner temperature of 85° C. for 5 hours, 150 ml of water was distilled off by a rotary evaporator. Thereto, 600 ml of methanol was added and the precipitated crystals were suction-filtered. After adding 50 ml of water, the crystals were dissolved under heating and thereto, 600 ml of methanol was added. The precipitated crystals were suction-filtered to obtain 89.0 g of the objective Compound A-3. The purity of this compound was examined by liquid chromatography and found to be 58.0% (yield: 71%). The conditions for the liquid chromatography were the same as those in Synthesis Example 1.

SYNTHESIS EXAMPLE 3

Compound (A-23) of the present invention was synthesized through the synthesis reaction route shown below.

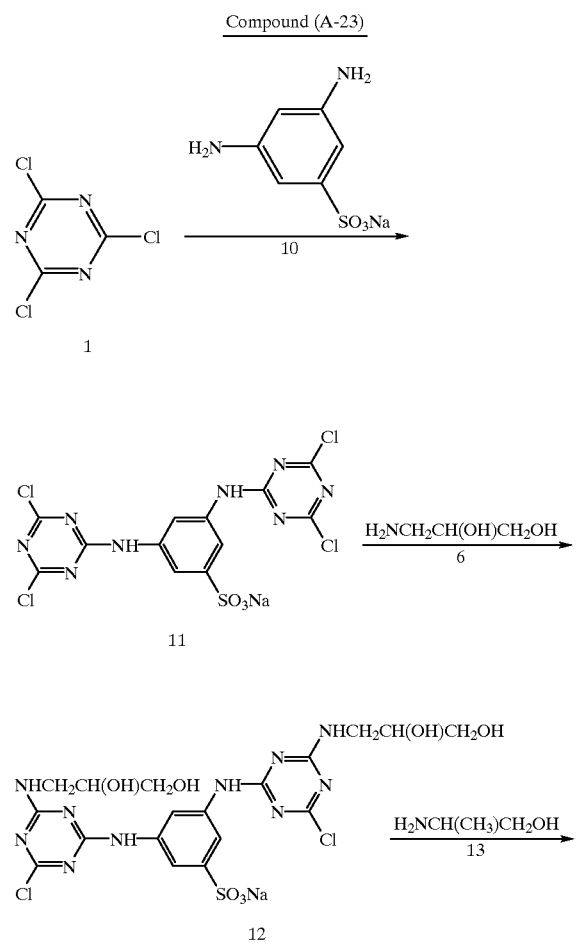

-continued

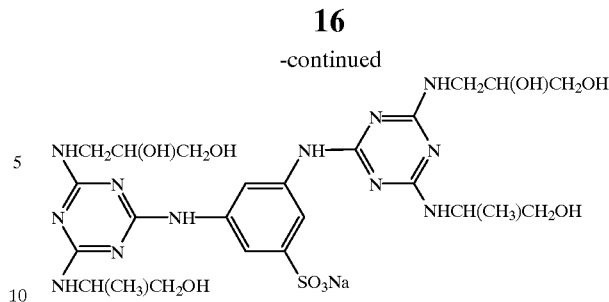

Synthesis of Compound 12

Into a three-neck flask, 37.6 g of Compound (1) and 280 ml of acetone were charged and the mixture was stirred in an ice-acetone bath. Thereto, a solution containing 21.0 g of Compound (10), 10.6 g of sodium carbonate and 250 ml of water was added dropwise over 15 minutes while keeping the inner temperature at −7 to 0° C. After the completion of dropwise addition, the ice-acetone bath was removed and stirring was continued in an ice-cooling bath for 30 minutes. Thereto, a solution obtained by dissolving 18.2 g of Compound (6) in 100 ml of acetone was added dropwise over 10 minutes and subsequently, a solution obtained by dissolving 10.6 g of sodium carbonate in 30 ml of water was added dropwise over 5 minutes. Thereafter, the ice bath was removed and stirring was continued for 3 hours. The precipitated crystals were suction-filtered to obtain the objective Compound (12) as a crude product. This product was intactly used in the next step.

Synthesis of Compound A-23

Into a three-neck flask, Compound (12) obtained above, 37.6 g of Compound (13) and 300 ml of water were charged and after stirring at an inner temperature of 85° C. for 5 hours, 150 ml of water was distilled off by a rotary evaporator. Thereto, 600 ml of methanol was added and the precipitated crystals were suction-filtered. After adding 60 ml of water, the crystals were dissolved under heating and thereto, 600 ml of methanol was added. The precipitated crystals were suction-filtered to obtain 58.7 g of the objective Compound A-23. The purity of this compound was examined by liquid chromatography and found to be 72.0% (yield: 61%). The conditions for the liquid chromatography were the same as those in Synthesis Example 1.

In the case where the compound of the present invention has a plurality of asymmetric carbons, a plurality of stereoisomers is present for the same structure and the present invention includes all possible stereoisomers. Out of multiple stereoisomers, only one stereoisomer or a mixture of several stereoisomers may be used.

In the processing composition of the present invention, one compound represented by formula (I) may be used or a plurality of the compounds may be used in combination. The number of compounds and the kind of the processing composition into which the compound is incorporated may be freely selected. The compound of the present invention may also be used in combination with one or a plurality of bis(triazinylarino)stilbene disulfonic acid compounds). Also at this time, the number of compounds used and the kind of the processing solution into which the compound is incorporated may be freely selected.

The bis(triazinylamino)stilbene disulfonic acid compound used in combination with the compound of the present invention may be a known or commercially available diaminostilbene-base fluorescent brightening agent. Preferred examples of known bis(triazinylamino)stilbene disulfonic acid compounds include the compounds described in JP-A-6-329936, JP-A-7-140625 and JP-A-10-

104809. Commercially available compounds are described, for example, in *Senshoku Note* (*Dyeing Note*), 19th ed., pp. 165–168, Sensyoku Sha. Among the products described therein, Blankophor BSUliq. REU and Hakkol BRK are preferred.

The compound of the present invention may be used in combination with a compound having a triazine ring other than bis(triazinylamino)stilbene disulfonic acid compounds in order to further improve solubility or residual color reduction effect. The compound having a triazine ring to be used in combination may be used singly or in combination. Examples of the compound having a triazine ring are set forth below, however, the present invention is not limited thereto.

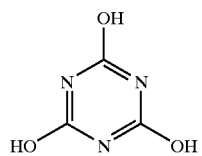

T-1

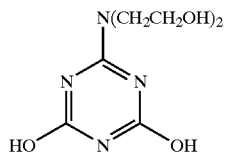

T-2

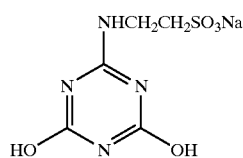

T-3

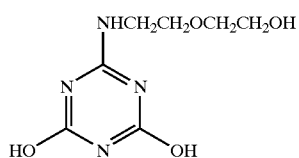

T-4

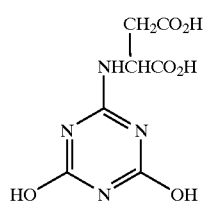

T-5

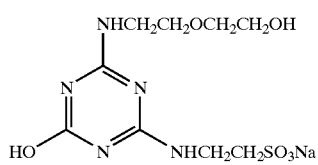

T-6

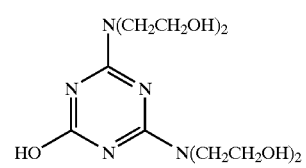

T-7

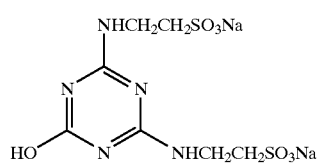

T-8

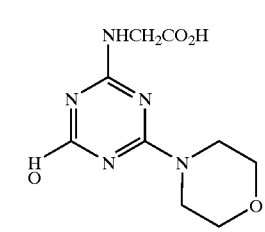

T-9

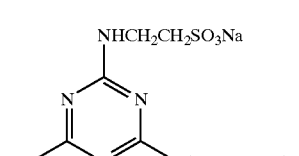

T-10

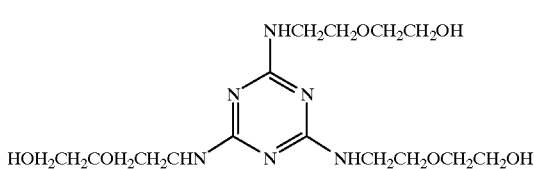

T-11

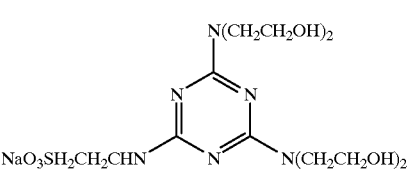

T-12

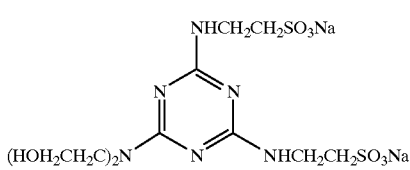

T-13

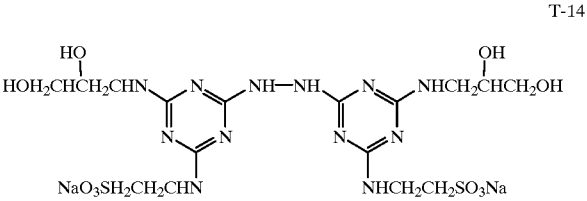

T-14

-continued
T-15
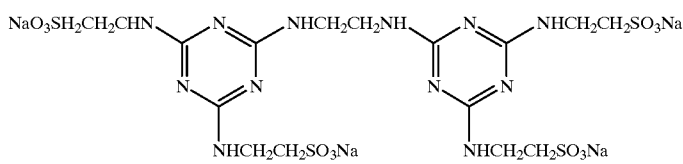
T-16
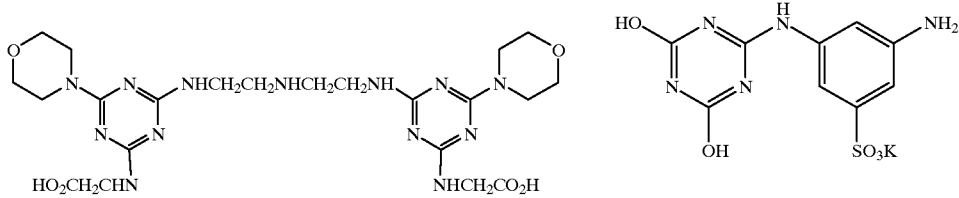
T-17
T-18
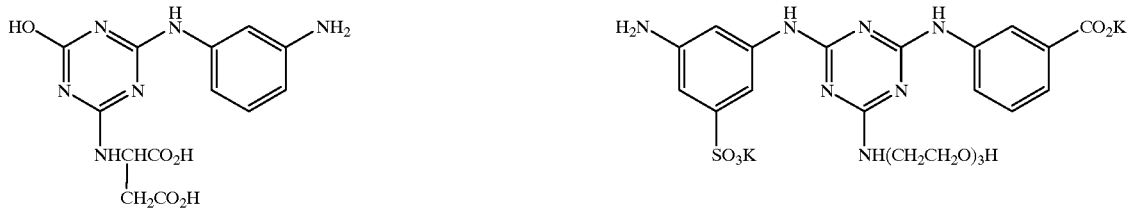
T-19
T-20
T-20
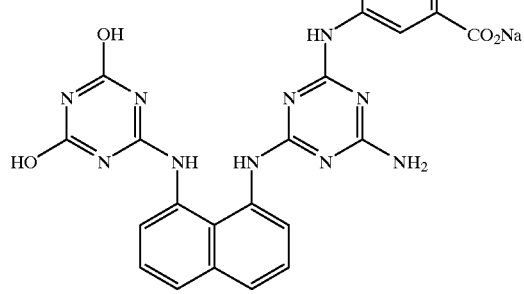
T-21
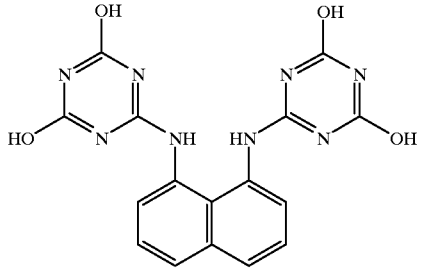
T-22
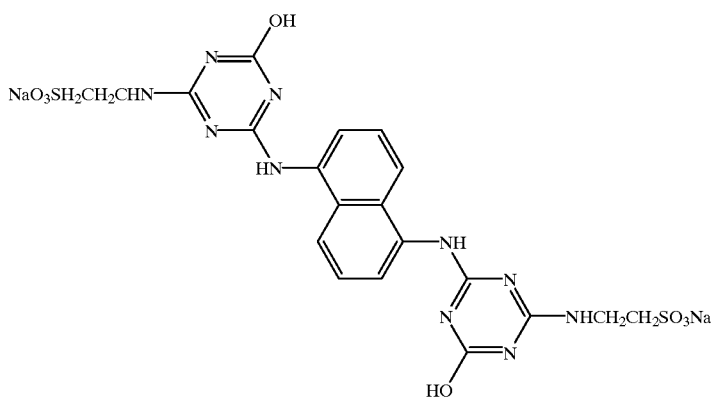

-continued

T-23
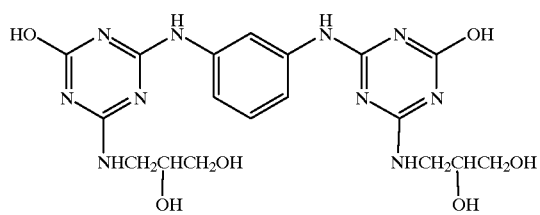

T-24
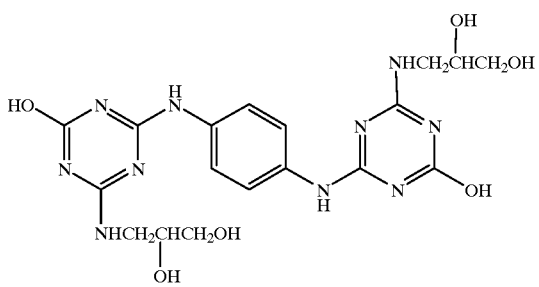

T-25
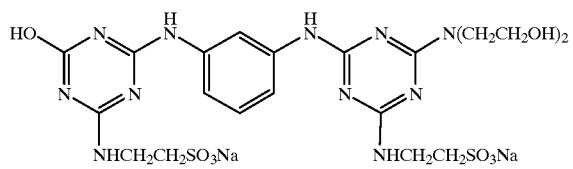

T-26
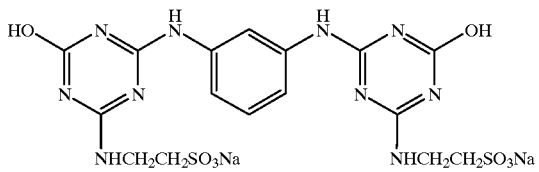

T-27
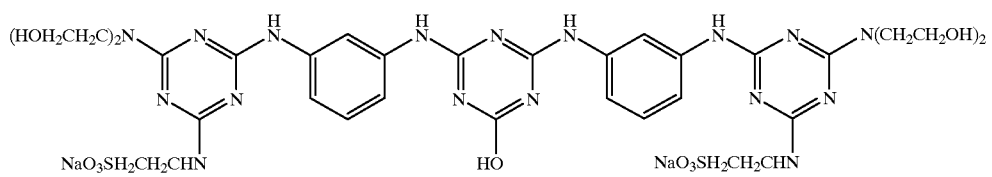

T-28
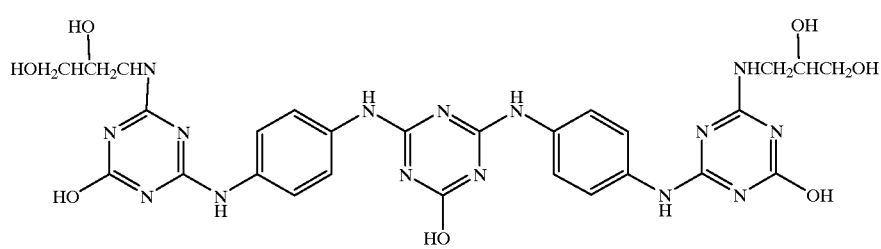

T-29
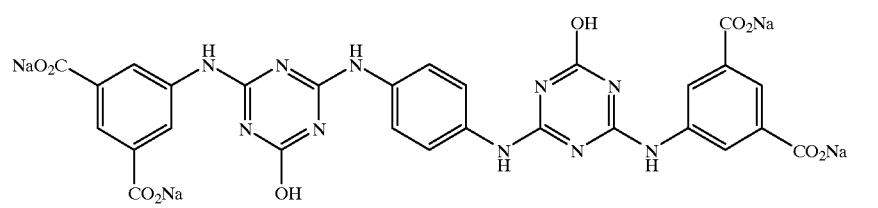

T-30
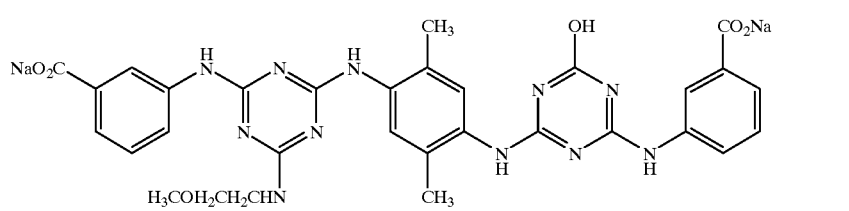

T-31
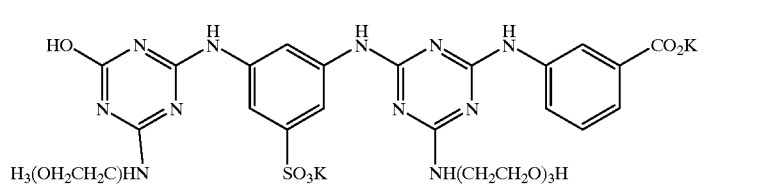

The processing composition for use in the present invention is described in detail below. The processing composition for use in the present invention means a processing composition necessary for the processing in performing the image information of a silver halide color photographic light-sensitive material. Specific examples thereof include a color developing composition, a bleaching composition, a bleach-fixing composition, a fixing composition, a water washing composition and a stabilizing composition. The processing solution may also be a black-and-white developing composition, a reversal composition or a prebleaching composition. These processing compositions may be prepared as a tank solution or a replenisher and may be prepared to have a concentration on use or as a concentrated solution. In the case of a concentrated solution, the processing composition of the present invention is mixed with water on use at a predetermined ratio and used as a replenisher or a tank solution. The compound of the present invention is characterized in that the composition formed in the state of a solution has excellent precipitation stability, however, the compound of the present invention may also be used for a processing solution in the granular, tablet, powder or slurry form.

The composition of the present invention may also be an additive composition. The term "additive composition" as used herein means a composition which is added to a tank solution or a replenisher necessary for the processing in performing the image formation of a silver halide color photographic light-sensitive material before or during the processing and exerts a function of controlling the photographic performance.

In the processing composition of the present invention, the concentration of the compound of formula (I) is, in the case of a working solution, from 0.05 to 20 mmol/L, preferably from 0.15 to 15 mmol/L, more preferably from 0.2 to 10 mmol/L. In the case where the processing composition of the present invention is diluted with water or another processing composition and then used, the concentration in the processing composition is a value obtained by multiplying the concentration magnification by the concentration in a solution on use. The "concentration magnification" used herein means, as commonly used in the art, a ratio between the component concentration in the processing composition and the component concentration in the processing solution on use.

The concentration of the bis(triazinylamino)stilbene disulfonic acid compound may be, in the case of a working solution, from 0.05 to 20 mmol/L, preferably from 0.1 to 10 mmol/L, more preferably 0.2 to 10 =mmol/L. In the case where the processing composition of the present invention is diluted with water or another processing composition and then used, the concentration in the processing composition is a value obtained by multiplying the concentration magnification by the concentration in a solution on use.

The concentration of the compound having a triazine ring other than the bis(triazinylamino)stilbene disulfonic acid compound may be, in the case of a working solution, from 0.01 to 10 mmol/L, preferably from 0.05 to 5 mmol/L, more preferably 0.1 to 5 mmol/L. In the case where the processing composition of the present invention is diluted with water or another processing composition and then used, the concentration in the processing composition is a value obtained by multiplying the concentration magnification by the concentration in a solution on use.

In the image formation method of the present invention, at least one processing step uses the processing composition of the present invention. The present invention may be used in a plurality of steps or all steps.

The process for producing the processing composition of the present invention includes several methods but good results may be obtained by the following three processes. In the practice of the present invention, the production process is, however, not limited to these three processes.

Process A

A process of previously introducing a small amount of water into a mixing tank and sequentially charging constituent chemicals thereinto while stirring.

Process B

A process of previously mixing constituent chemicals in a mixing tank and charging a small amount of water en bloc.

Process C

A process of previously classifying the constituent chemicals into appropriate groups, dissolving each group in water or a hydrophilic organic solvent to form a concentrated solution and mixing respective concentrated solutions.

A production process partially employing these processes may also be used.

The processing composition of the present invention may be a developing composition, a bleach-fixing composition, a fixing composition, a water washing or stabilizing composition or an additive composition and these processing compositions are described below one by one.

The color developing composition of the present invention contains a color developing agent and the color developing agent is preferably a known aromatic primary amine color developing agent, more preferably a p-phenylenediamine derivative. Typical examples thereof are set forth below, however, the present invention is not limited thereto. Recently, in some black-and-white light-sensitive materials, a coupler is added to form a black color and a black-and-white image is formed using a general purpose color developing solution. The processing composition of the present invention can also be applied to such light-sensitive materials.

1) N,N-Diethyl-p-phenylenediamine
2) 4-Amino-N,N-diethyl-3-methylaniline
3) 4-Amino-N-(β-hydroxyethyl) N-methylaniline
4) 4-Amino-N-ethyl-N-(β-hydroxyethyl)aniline
5) 4-Amino-3-methyl-N-ethyl-N-(β-hydroxyethyl)aniline
6) 4-Amino-3-methyl-N-ethyl-N-(3-hydroxypropyl)aniline
7) 4-Amino-3-methyl-N-ethyl-N-(4-hydroxybutyl)aniline
8) 4-Amino-3-methyl-N-ethyl-N-(β-methanesulfonamidoethyl)aniline
9) 4-Amino-N,N-diethyl-3-(β-hydroxyethyl)aniline
10) 4-Amino-3-methyl-N-ethyl-N-(β-methoxyethyl)aniline
11) 4-Amino-3-methyl-N-(β-ethoxyethyl)-N-ethylaniline
12) 4-Amino-3-methyl-N-(3-carbamoylpropyl)-N-n-propylaniline
13) 4-Amino-3-methyl-N-(4-carbarmoylbutyl)-N-n-propylaniline
14) N-(4-Amino-3-methylphenyl)-3-hydroxypyrrolidine
15) N-(4-Amino-3-methylphenyl)-3-hydroxymethylpyrrolidine
16) N-(4-Amino-3-methylphenyl)-3-pyrrolidinecarboxamide Among these p-phenylenediamine derivatives, Compounds 5) to 8) and 12) are preferred, and Compounds 5) and 8) are more preferred. These p-phenylenediamine derivatives in the state of a solid are usually a sulfate, a hydrochloride, a p-toluenesulfonate, a naphthalenedisulfonate or an N,N-bis(sulfonatoethyl)hydroxylamine. These derivatives may also be added as a free form having no counter salt. The concentration of the aromatic primary amine developing agent is from 4 to 100 mmol/L, preferably from 6 to 50 mmol/L, more preferably from 8 to 25 mmol/L, in the solution on use.

The color developer of the present invention may contain a compound capable of preventing the precipitation of color developing agent and examples thereof include polyethylene glycols, arylsulfonic acids, alkylsulfonic acids and urea compounds described in JP-A-11-174643. Among these, diethylene glycol, polyethylene glycol 300, p-toluenesulfonic acid and salts thereof, a linear alkylsulfonic acid having from 5 to 9 carbon atoms and salts thereof, and ethylene urea are preferred, because these scarcely affect the photographic properties and exhibit good effect.

The color developing composition of the present invention preferably contains a compound capable of preventing the color developing agent from deterioration due to air oxidation, namely, a preservative. Sulfite and hydroxylamine are preferred as the inorganic preservative. Such an inorganic preservative exhibits an extremely high preservation activity and is preferably used in combination with an organic preservative. Depending on the light-sensitive material to be processed, sulfite and hydroxylamine sometimes adversely affect the photographic properties during the process of color development and therefore, in some cases, only either one is used or these are not substantially contained but only an organic preservative is used.

Examples of effective organic preservatives include hydroxyamine derivatives, hydroxamic acids, hydrazides, phenols, α-hydroxyketones, α-aminoketones, saccharides, monoamines, diamines, polyamines, quaternary ammonium salts, nitroxyl radicals, alcohols, oximes, diamides, condensed cyclic amines, cyclic amides, salicylic acids, polyethyleneimines, alkanolamines and aromatic polyhydroxy compounds. Among these organic preservatives, hydroxylamine derivatives described in JP-A-3-56456 and JP-A-3-33845, and compounds described in JP-A-3-33846 and JP-A-6-148841 are preferred.

The hydroxylamine derivative is preferably used in combination with an alkanolamine from the standpoint of improving the stability of color developer in the continuous processing. Examples of the compound with which the hydroxylamine is preferably used in combination include triisopropanolamine and triethanolamine. A combination use with a cyclic amide compound is also preferred and among the cyclic amide compounds, ε-caprolactam is particularly preferred.

The pH of the color developing composition of the present invention is preferably from 9.5 to 13.5 and the color developer prepared therefrom is from 9.0 to 12.2, preferably from 9.9 to 11.2. In order to maintain the pH, a buffer is preferably added and the buffer is preferably a potassium or sodium salt of an inorganic salt such as carbonate, bicarbonate, phosphate, borate and tetraborate. Also, an organic compound such as 5-sulfosalicylic acid, β-alanine, proline and trishydroxyaminomethane is preferably used, however, the present invention is not limited to these compounds. The buffer is incorporated to a concentration of 0.1 mol/L or more, preferably from 0.1 to 0.4 mol, in terms of a concentration of color developing replenisher.

The color developing composition of the present invention may contain various chelating agents as a precipitation inhibitor, such as calcium and magnesium. The chelating agents may be used individually or in combination of two or more. Preferred compounds therefor include nitrilotriacetic acid, diethylenetriaminepentaacetic acid, ethylenediaminetetraacetic acid, N,N,N-trimethylenephosphonic acid, ethylenediamine-N,N,N',N'-tetramethylenesulfonic acid, ethylenediaminesuccinic acid (s,s form), 2-phosphonobutane-1,2,4-tricarboxylic acid, 1-hydroxyethylidene-1,1-dihosphonic acid and 1,2-dihydroxybenzen-4,6-disulfonic acid. The chelating agent may be sufficient if it is added in an amount large enough to conceal metal ion in the color developer. The chelating agent is usually added to a concentration of approximately from 0.1 to 10 g/L.

If desired, an arbitrary development accelerator may be added to the color developing composition of the present invention. Examples of the development accelerator include polyalkylene oxide, 1-phenyl-3-pyrazolidones, alcohols and carboxylic acids.

In addition, an arbitrary antifoggant may be added to the color developing composition of the present invention. Examples of the antifoggant include metal halides such as potassium bromide and potassium iodide, and organic antifoggants represented by a nitrogen-containing heterocyclic compound. Examples of the organic antifoggant include benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole, indazole, hydroxyazaindolidine and adenine. Other than these, an alkylcarboxylic acid, an arylcarboxylic acid or a saccharide may also be added, if desired.

In the color development applied to the present invention, the processing temperature is, in the case of a color print light-sensitive material, from 30 to 55° C., preferably from 35 to 50° C., more preferably from 38 to 45° C. The developing time is from 5 to 90 seconds, preferably from 6 to 60 seconds, more preferably from 10 to 45 seconds. The replenishing amount, which is preferably smaller, is suitably from 15 to 200 mL, preferably from 20 to 120 mL, more preferably from 30 to 60 mL, per 1 $m^2$ of the light-sensitive material.

In the case of a color negative film, the processing temperature is from 30 to 55° C., preferably from 35 to 50° C., more preferably from 38 to 45° C. The developing time is from 45 seconds to 5 minutes, preferably from 60 seconds to 4 minutes, more preferably from 90 seconds to 3 minutes to 15 seconds. The replenishing amount, which is preferably smaller, is suitably from 10 to 200 mL, preferably from 12 to 60 mL, more preferably from 15 to 30 mL, per 1 roll of 24 exp.

In the case of a color reversal film, the processing temperature is from 32 to 45° C., preferably from 35 to 40° C., more preferably 36.5 to 39.5° C. The developing time is from 4 to 8 minutes, preferably from 5 to 7 minutes more preferably from 5 minutes 30 seconds to 6 minutes 30 seconds. The replenishing amount, which is preferably smaller, is suitably from 1,000 to 3,000 mL, preferably from 1,500 to 2,800 mL, more preferably from 2,000 to 2,400 mL, per 1 $m^2$ of the light-sensitive material.

The color developing composition obtained by concentrating the replenisher described in JP-A-11-174643, JP-A-11-194461 and JP-A-11-194462 is a preferred embodiment.

The bleaching agent for use in the bleaching composition and the bleach-fixing composition of the present invention may be a known bleaching agent but in particular, an organic complex salt (a complex salt of, for example, an aminopolycarboxylic acid or an organic acid such as citric acid, tartaric acid and malic acid), a persulfate and a hydrogenperoxide of iron(III) are preferred. Two or more bleaching agents may also be used in combination.

Among these, an organic complex salt of iron(III) is preferred in view of rapid processability and environmental antipollution. Examples of the aiminopolycarboxylic acid or a salt thereof useful for forming an organic complex salt of iron(III) include compounds such as biodegradable ethylenediaminesuccinic acid (ss-form), biodegradable N-2-carboxylatoethyl)-L-aspartic acid, biodegradable β-alaninediacetic acid, biodegradable methyliminodiacetic acid, ethylenediaminetetraacetic acid, diethylenetriaminepentaacetic acid, 1,3-propylenediaminetetraacetic acid, nitrilotriacetic acid, cyclohexanediaminetetraacetic acid, iminodiacetic acid and glycol ether diaminetetraacetic acid. These compounds may be in the form of a sodium salt, a potassium salt, a lithium salt or an ammonium salt. Among these compounds, ethylenediaminesuccinic acid (s,s-form), N-(2-carboxylatoethyl)-L-aspartic acid, β-alaninediacetic acid, methyliminodiacetic acid, ethylenediaminetetraacetic acid, diethylenetriaminepentaacetic acid and 1,3-propylenediaminetetraacetic acid are preferred because their iron(III) complex salts provide good photographic properties. The ferric complex salt may be used in the complex salt form or a ferric ion complex salt may be formed from a ferric salt such as ferric sulfate, ferric chloride, ferric nitrate, ammonium ferric nitrate and ferric phosphate, using a chelating agent such as aminopolycarboxylic acid. The chelating agent may also be used in excess of the amount necessary for the formation of a ferric ion complex salt. The concentration of the bleaching agent in the bleaching or bleach-fixing solution is, in terms of a concentration in a solution on use, from 0.01 to 1.0 mol/L, preferably from 0.05 to 0.50 mol/L, more preferably from 0.1 to 0.5 mol/L.

A buffer is also preferably added to the bleaching or bleach-fixing solution. The buffer selected varies depending on the intended pH, however, preferred examples of the compound therefor include organic acids such as succinic acid, maleic acid, glycolic acid, malonic acid, fumaric acid, sulfosuccinic acid and acetic acid, organic bases such as imidazole and dimethylimidazole, and the compounds represented by formulae (A-a) and (B-b) of JP-A-9-211819. The amount of this compound added is preferably from 0.005 to 3.0 mol/L, more preferably from 0.05 to 1.5 mol/L, in a solution on use. The pH region of the bleaching solution is preferably from 2 to 7, more preferably from 3 to 6. In the case of the bleach-fixing solution, the pH is preferably from 3 to 8, more preferably from 4 to 7.

In the bleach-fixing of a color print light-sensitive material applied to the present invention, the processing temperature is from 30 to 55° C., preferably from 35 to 50° C., more preferably from 38 to 45° C. The bleach-fixing time is from 5 to 90 seconds, preferably from 8 to 60 seconds, more preferably from 10 to 45 seconds. The replenishing amount, which is preferably smaller, is suitably from 20 to 200 mL, preferably from 25 to 120 mL, more preferably from 30 to 50 mL, per 1 $m^2$ of the light-sensitive material.

In the bleaching of a color negative film, the processing temperature is from 30 to 55° C., preferably from 35 to 50° C., more preferably from 38 to 45° C. The bleaching time is from 12 seconds to 2 minutes, preferably from 15 seconds to 1 minute and 15 seconds, more preferably from 18 to 60 seconds. The replenishing amount, which is preferably smaller, is suitably from 2.5 to 50 mL, preferably from 3 to 25 mL, more preferably from 4 to 12 mL, per 1 roll of 24 exp.

In the bleaching of a color reversal film, the processing temperature is from 30 to 45° C., preferably from 33 to 40° C., more preferably from 37 to 39° C. The bleaching time is from 4 to 8 minutes, preferably from 5 to 7 minutes, more preferably from 5 minutes and 30 seconds to 6 minutes and 30 seconds. The replenishing amount, which is preferably smaller, is suitably from 160 to 400 mL, preferably from 180 to 300 mL, more preferably from 200 to 250 mL, per 1 $m^2$ of the light-sensitive material.

The fixing agent for use in the bleach-fixing composition and the fixing composition of the present invention is a known fixing agent. Specific examples thereof include thiosulfates such as sodium thiosulfate and ammonium thiosulfate; thiocyanates such as sodium thiocyanate and ammonium thiocyanate; ethylenebisglycolic acid, 3,6-dithia-1,8-octanediol and thioether compounds described in JP-A-4-317055; thioureas; and water-soluble silver halide dissolving agents described in JP-A-4-143757 and JP-A-4-230749, such as mesoionic compound. These may be used individually or in combination of two or more thereof. The fixing agent is preferably a thiosulfate, more preferably ammonium thiosulfate. The concentration of the fixing gent in the fixing solution or bleach-fixing solution is preferably from 0.3 to 2 mol/L, more preferably from 0.5 to 1.5 mol/L.

The bleach-fixing composition or the fixing composition preferably contains a buffer. Preferred examples of the buffer include heterocyclic organic bases such as imidazole and dimethylimidazole, aminoalkylenesulfonic acid such as taurine, and dibasic acids such as succinic acid, maleic acid and malonic acid. The pH is preferably from 3 to 8, more preferably from 4 to 7.

The bleach-fixing composition and the fixing composition of the present invention preferably contain, as a preservative, a compound capable of releasing sulfite ion, namely, a sulfite, a bisulfite or a metabisulfite. This compound is preferably added in the form of a potassium salt, a sodium salt or an ammonium salt. Also, an arylsulfinic acid such as p-toluenesulfinic acid, m-carboxybenzenesulfinic acid and p-aminobenzenesulfinic acid, is preferably contained. Such a compound is preferably contained to a concentration of 0.02 to 1.0 mol/L in a solution on use. Other than those described above, an ascorbic acid, a carbonyl bisulfite adduct or a carbonyl compound may be added as the preservative.

The bleach-fixing composition and the fixing composition of the present invention may also contain a mercapto nitrogen-containing heterocyclic compound capable of forming stable silver ion so as to improve the image preservability, such as mercaptotriazole, aminomercaptotriazole and N-methylmercaptoimidazole, or a bisamidine, a bisguanidine or a monoamidine described in JP-A-5-303185, which accelerates the washing out of developing agent. Other than these, a polymer such as polyethylene glycol or polyvinylpyrrolidone, a chelating agent, a defoaming agent, an antifungal and the like may be added, if desired, to the bleaching composition and the fixing composition of the present invention.

In the bleach-fixing of a color print light-sensitive material applied to the present invention, the processing temperature, the bleach-fixing time and the replenishing amount are the same as those described above. In the fixing of a color negative film, the processing temperature is from 30 to 55° C., preferably from 35 to 50° C., more preferably from 38 to 45° C. The bleaching time is from 20 seconds to 2 minutes, preferably from 30 seconds to 1 minute and 40 seconds, more preferably from 35 seconds to 1 minute and 20 seconds. The replenishing amount, which is preferably smaller, is suitably from 4 to 60 mL, preferably from 5 to 40 mL, more preferably from 6 to 30 mL, per 1 roll of 24 exp.

In the fixing of a color reversal film, the processing temperature is from 30 to 45° C., preferably from 33 to 40° C., more preferably from 37 to 39° C. The fixing time is from 2 to 6 minutes, preferably from 3 to 5 minutes, more preferably from 3 minutes and 30 seconds to 4 minutes and 30 seconds. The replenishing amount, which is preferably smaller, is suitably from 800 to 2,000 mL, preferably from 900 to 1,500 mL, more preferably from 1,000 to 1,250 mL.

The washing composition and the stabilizing composition of the present invention may contain formalin, formaldehyde, pyruvinaldehyde, a formaldehyde bisulfite adduct described in U.S. Pat. No. 4,921,779, or an N-methylol compound described in JP-A-5-34889, so as to inhibit discoloration of a dye and generation of staining, which are ascribable to the residual magenta coupler. Also, washing composition and the stabilizing composition of the present invention preferably contain an arylsulfinic acid such as p-toluenesulfinic acid, m-carboxybenzenesulfinic acid and p-aminobenzenesulfinic acid. Furthermore, a surfactant as a water-cutting agent, a chelating agent as a hard water-softening agent, a buffer for adjusting the pH, a defoaming agent, an antifungal, an antiseptic and the like may be added, if desired.

The pH is preferably from 4 to 10, more preferably from 5 to 8. The processing temperature may be variously selected according to the use and properties of the light-sensitive material, however, the processing temperature is generally from 20 to 50° C., preferably from 25 to 45° C.

The additive composition of the present invention preferably comprises the compound of the present invention and water, however, if desired, a water-soluble aliphatic compound, a bis(triazinylamino)stilbene disulfonic acid compound, a chelating agent, an inorganic salt and the like may be added. The water-soluble aliphatic compound is preferably a glycol such as diethylene glycol and polyethylene glycol 300 (average molecular weight; 300), or an alkanolamine such as triethanolamine and triisopropanolamine. In particular, diethylene glycol is preferred. The additive composition of the present invention can be added to any processing bath or replenisher which is considered necessary for the processing in performing the image formation of a silver halide color photographic light-sensitive material. In the additive composition, the compound of the present invention is preferably concentrated and the concentration ratio to the working solution is from 50 to 4,000 magnifications, preferably from 100 to 2,000 magnifications, more preferably from 200 to 1,000 magnifications. One preferred embodiment is a method of adding the additive composition of the present invention to a fixing bath and/or a fixing replenisher in the color reversal processing, however, the present invention is not limited thereto.

Out of the photographic element which is processed using the present invention, the light-sensitive material may contain any normal silver halide such as silver chloride, silver bromide, silver bromoiodide, silver chlorobromide, silver chloroiodide and a mixture thereof. In one embodiment, the light-sensitive material of the photographic element is a high silver chloride light-sensitive material containing at least 50 mol % or more of silver chloride, preferably at least 90 mol % or more of silver chloride, and in many cases, this is used as a light-sensitive material for color print.

In another embodiment, at least one emulsion in the light-sensitive material mainly comprises silver bromide (at least 50 mol % of silver bromide). The photographic element most preferably has one or more color recording layer and each color recording layer comprises one or more silver halide emulsion, mainly silver bromide emulsion, as used in color negative film or color reversal film. The photographic element containing a light-sensitive material processed by practicing the present invention may be a nmonochromatic element or a multicolor element. The photographic element may also have a magnetic recording layer known in this technical field.

Individual photographic elements are described in detail, for example, in Research Disclosure (hereinafter simply referred to as "RD"), specifically, in RD 17643, pp. 23–27, RD18716, pp. 647–650, RD307105, pp. 866–868 and 873–879, and RD36544, pp. 501–541. These are related to useful (negative or positive) silver halide emulsions and preparation methods thereof, various sensitizers, dye-forming coupler, image dye stabilizer, dye, ultraviolet absorbent, filter, binder, hardening agent, plasticizer, lubricant, coating aid, surfactant, antistatic agent, matting agent, paper or film support, and various image formation methods of a negative or positive image-forming color element.

It is advantageous to construct the processing composition of the present invention in a form such that all components for the solution on use are contained in one composition, namely, a one-part structure. However, if it is not preferred to allow the constituent components to come into contact for a long period of time in the color developing composition, bleach-fixing composition or the like, the constituent components may be separated into two or more liquid agents or solid admixtures and the processing composition may be constructed to have a two-part or three-part structure. These processing agent structures are usually called a one-, two- or three-part structure according to the naming of International Standard ISO5989 (Terms of Mixed Processing Agents). The effects and characteristic features of the invention are not lost even when the processing composition of the present invention is divided into parts. Among these structures, a one-part structure is particularly preferred for the color developing composition.

For the container of the processing composition of the present invention, a known material may be used. The container may be formed of a single material or a composite material, for example, a composite material comprising a material having high gas permeability and a material having high stability against alkali. In view of re-use or recycling, the container is preferably composed by a single construction material. Examples of the material used for the container include polyester resin, polyolefin resin, acrylic resin, ABS resin, epoxy resin, polyamide resin such as nylon, polyurethane resin, polystyrene resin, polycarbonate resin, PVA, polyvinyl chloride, polyvinylidene chloride and polyethylene resin. Among these, a container composed of a single material using a polyester resin such as polyethylene terephthalate and polyethylene naphthalate, or a polyolefin resin such as polyethylene and polypropylene, is preferred. In particular, the container material is more preferably a polyethylene resin and still more preferably a high-density polyethylene resin (HDPE).

Insofar as the processing composition is not affected, the container material for use in the present invention may contain carbon black, titanium white, a pigment, calcium carbonate, a plasticizer having compatibility with the material, and the like. The container material is preferably such that polyethylene occupies 85% or more in the material and a plasticizer is not contained, more preferably such that polyethylene occupies 95% or more and a plasticizer is not contained.

The shape and structure of the container into which the processing composition of the present invention is filled can be freely designed according to the purpose. In addition to a fixed form bottle, a freely shrinkable type described in JP-A-1-235950, a container with a flexible partition described in JP-A-62-134626, and the like may also be used. The container described in JP-A-11-282148 is particularly preferred as the container for the processing composition of the present invention in view of the capacity, space efficiency, self-sustained standing, shape retentivity and re-use/recycling property. A preferred embodiment is a kit where a plurality of compositions of the present invention are filled in containers having the same shape and shame volume and formed of a single constituent material and these containers are integrated into a single cartridge. Examples thereof include the cartridge described in JP-A-2000-3014. The combination of processing compositions in the cartridge can be freely selected. The cartridges described in JP-A-11-295858 and JP-A-11-288068, where a developing composition, a bleaching composition and a fixing composition are integrated, are a preferred embodiment.

The present invention is described in greater detail below by referring to the Examples, including the stability of the processing composition of the present invention against the deposition of precipitates and also the photographic properties. However, the present invention should not be construed as being limited thereto.

EXAMPLE 1

(1) Preparation of Color Developing Composition

A concentrated liquid agent-type color developing composition was prepared according to the following formulation.

| | |
|---|---|
| Compound of the present invention or Comparative Compound | see Table 1 |
| Fluorescent brightening agent (FL-1 shown below) | 1.75 g |
| Triisopropanolamine | 34.0 g |
| Ethylenediaminetetraacetic acid | 15.0 g |
| Sodium sulfite | 0.80 g |
| Polyethylene glycol (average molecular weight: 300) | 40.0 g |
| Sodium 4,5-dihydroxybenzene-1,3-disulfonate | 2.0 g |
| Disodium N,N-bis (sulfonatoethyl) hydroxylamine | 55.0 g |
| 4-Amino-3-methyl-N-ethyl-N-(β-methanesulfonamidoethyl) aniline.3/2 sulfate.monohydrate | 55.0 g |
| Potassium hydroxide | 19.0 g |
| Sodium hydroxide | 24.0 g |
| Potassium carbonate | 100.0 g |
| Water to make a total of | 1,000 mL |
| pH | 13.2 |

Stabilizer (Cpd-1), 10 g of Color Image Stabilizer (Cpd-9), 10 g of Image Stabilizer (Cpd-10), Color Image Stabilizer (Cpd-12), 14 g of Ultraviolet Absorbent (UV-1), 50 g of Ultraviolet Absorbent (TV-2), 40 g of Ultraviolet Absorbent (UV-3) and 60 g of Ultraviolet Absorbent (UV-4) were dissolved. The resulting solution was dispersed by emulsification in 6,500 g of an aqueous 10% gelatin solution containing 25 g of sodium dodecylbenzenesulfonate to prepare Emulsification Dispersion C.

Separately, Silver Chlorobromide Emulsion C (cubic; a 5:5 (by mol of silver) mixture of Large-Size Emulsion C having an average grain size of 0.40 μm and Small-Size Emulsion C having an average grain size of 0.30 μm, where the coefficient of variation of the grain size distribution was 0.09 and 0.11, respectively; the emulsions of respective sizes containing 0.5 mol % of silver bromide partially localized on the surface of a grain basically composed of a silver chloride emulsion).

In this emulsion, Red-Sensitive Sensitizing Dyes G and H shown below each was added in an amount of $9.0 \times 10^{-5}$ mol/mol-Ag to Large-Size Emulsion C and in an amount of $12.0 \times 10^{-5}$/mol-Ag to Small-Size Emulsion C. Furthermore, the chemical ripening of this emulsion was optimally performed by adding a sulfur sensitizer and a gold sensitizer.

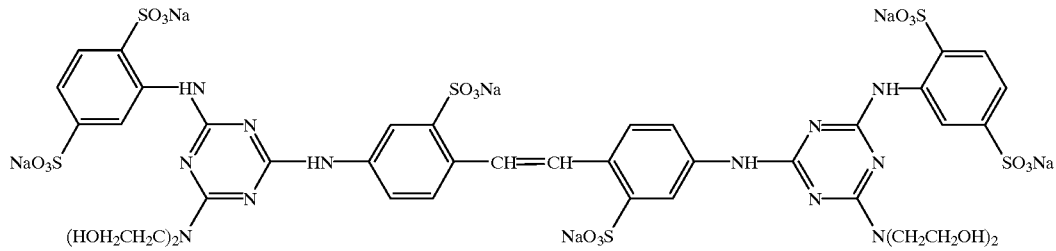

FL-1

(2) Preparation of Light-Sensitive Material Sample

The surface of a support obtained by covering two surfaces of a paper with a polyethylene resin was subjected to a corona discharge treatment, and a gelatin undercoat layer containing sodium dodecylbenzenesulfonate was provided thereon. Subsequently, from first to seventh layers were provided in sequence to prepare Silver Halide Color Photographic Light-sensitive Material P-1 having a layer structure shown below. The coating solutions for respective photographic constituent layers were prepared as follows.

Preparation of Coating Solution for Fifth Layer

In 230 g of Solvent (Solv-6) and 350 ml of ethyl acetate, 300 g of Cyan Coupler (ExC), 250 g of Color Image Emulsification Dispersion C prepared above and Silver Chlorobromide Emulsion C were mixed and dissolved to prepare a coating solution for the fifth layer having a composition shown below in the layer structure formulation for each layer.

Preparation of Coating Solutions for Respective Layers

The coating solutions for the first to fourth layers and for the sixth and seventh layers were also prepared in the same manner as the coating solution for the fifth layer. In each layer, 1-oxy-3,5-dichloro-s-triazine sodium salt was used as the gelatin hardening agent. Furthermore, Antiseptics Ab-1, Ab-2, Ab-3 and Ab-4 were added to each layer to make a total amount of 15.0 mg/m², 60.0 mg/m², 5.0 mg/m² and 10.0 mg/m², respectively.

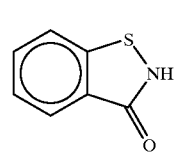

Antiseptic Ab-1

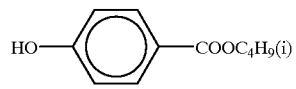

Antiseptic Ab-2

-continued

Antiseptic Ab-3

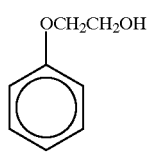

Antiseptic Ab-4

A 1:1:1:1 mixture of a, b, c and d.

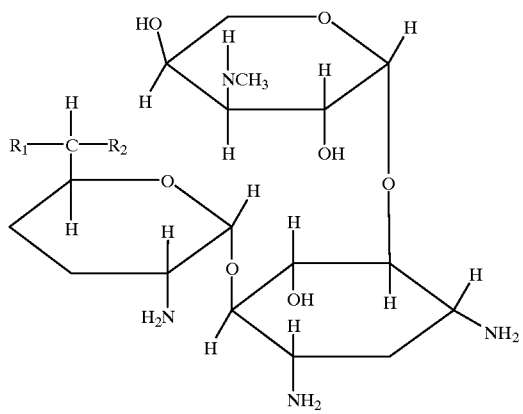

| | $R_1$ | $R_2$ |
|---|---|---|
| $C_1$ | $H_3C-$ | $-NHCH_3$ |
| $C_2$ | $H_3C-$ | $-NH_2$ |
| $C_{10}$ | $H-$ | $-NH_2$ |
| $C_{20}$ | $H-$ | $-NHCH_3$ |

Spectral Sensitization

Spectral sensitizing dyes shown below were used for the silver chlorobromide emulsion of each light-sensitive emulsion layer.

Blue-Sensitive Emulsion Layer

Sensitizing Dye A

Sensitizing Dye B

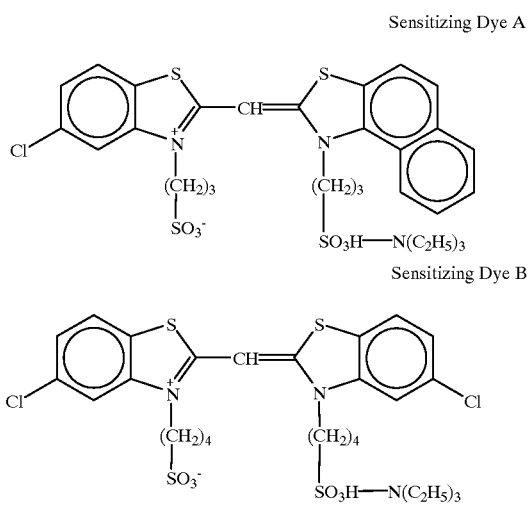

Sensitizing Dye C

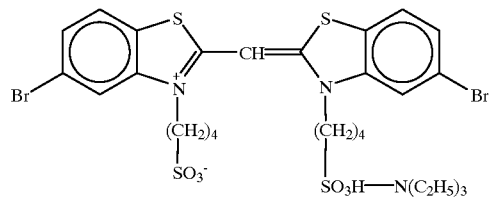

(Sensitizing Dyes A and C each was added in an amount of $0.42 \times 10^{-4}$ mol per mol of silver halide to the large-size emulsion and in an amount of $0.5 \times 10^{-4}$ mol per mol of silver halide to the small size emulsion, and Sensitizing Dye B was added in an amount of $3.4 \times 10^{-4}$ mol per mol of silver halide to the large-size emulsion and in an amount of $4.1 \times 10^{-4}$ mol per mol of silver halide to the small-size emulsion).

Green-Sensitive Emulsion Layer

Sensitizing Dye D

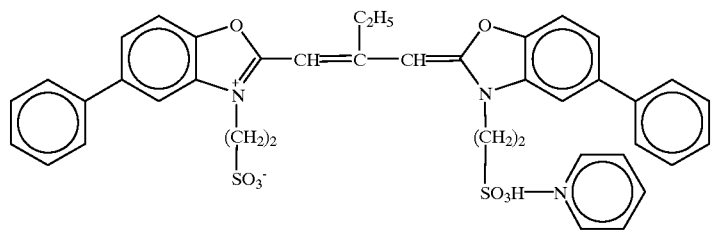

Sensitizing Dye E

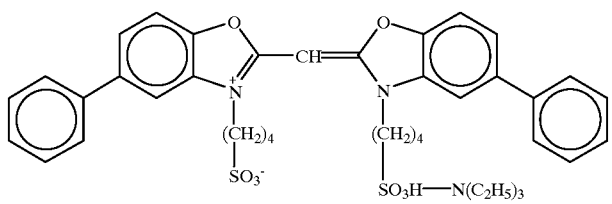

Sensitizing Dye F

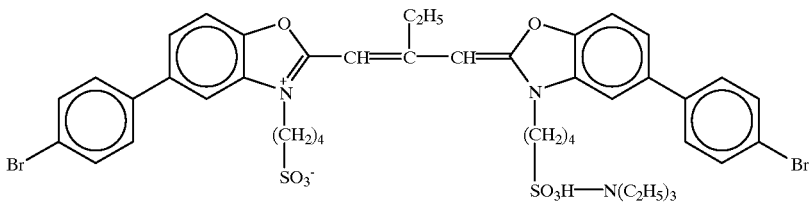

(Sensitizing Dye D was added in an amount of $3.0 \times 10^{-4}$ mol per mol of silver halide to the large-size emulsion and in an amount of $3.6 \times 10^{-4}$ mol per mol of silver halide to the small size emulsion, Sensitizing Dye E was added in an amount of $4.0 \times 10^{-4}$ mol per mol of silver halide to the large-size emulsion and in an amount of $7.0 \times 10^{-5}$ mol per mol of silver halide to the small-size emulsion, and Sensitizing Dye F was added in an amount of $2.0 \times 10^{-4}$ mol per mol of silver halide to the large-size emulsion and in an amount of $2.8 \times 10^{-4}$ mol per mol of silver halide to the small-size emulsion).

Red-Sensitive Emulsion Layer

Sensitizing Dye G

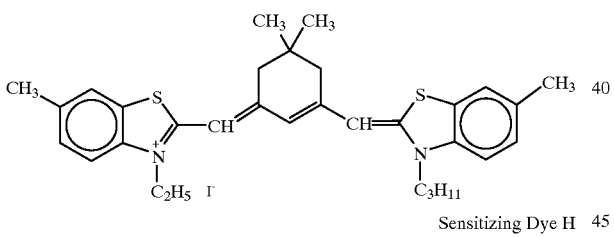

Sensitizing Dye H

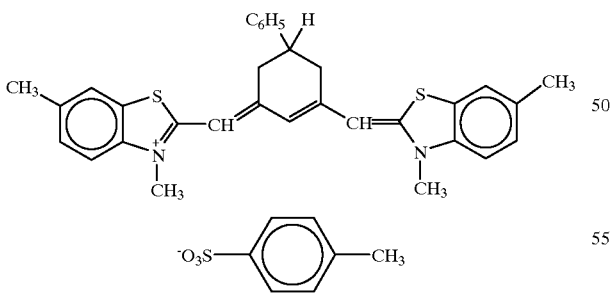

(Sensitizing Dyes G and H each was added in an amount of $8.0 \times 10^{-5}$ mol per mol of silver halide to the large-size emulsion and in an amount of $10.7 \times 10^{-5}$ mol per mol of silver halide to the small size emulsion). Furthermore, Compound I shown below was added to the red-sensitive emulsion layer in an amount of $3.0 \times 10^{-3}$ mol per mol of silver halide.

Compound I

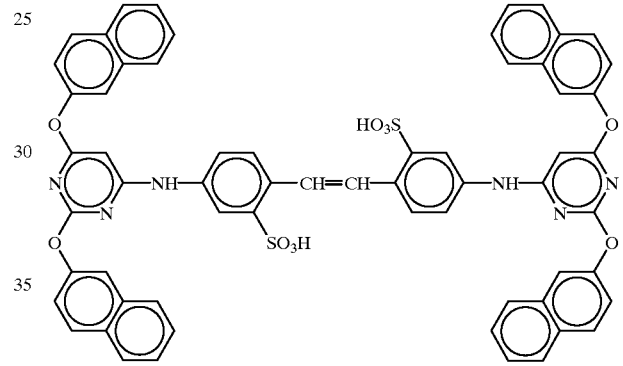

To the blue-sensitive emulsion layer, the green-sensitive emulsion layer and the red-sensitive emulsion layer, 1-(3-methylureidophenyl)-5-mercaptotetrazole was added in an amount of $3.3 \times 10^{-4}$ mol, $1.0 \times 10^{-3}$ mol and $5.9 \times 10^{-4}$ mol, respectively, per mol of silver halide.

This was also added to the second, fourth, sixth and seventh layers to a coverage of 0.2 mg/m$^2$, 0.2 mg/m$^2$, 0.6 mg/m$^2$ and 0.1 mg/m$^2$, respectively.

To the blue-sensitive emulsion layer and the green-sensitive emulsion layer, 4-hydroxy-6-methyl-1,3,3a,7-tetrazaindene was added in an amount of in an amount of $1 \times 10^{-4}$ mol and $2 \times 10^{-4}$ mol, respectively, per mol of silver halide.

To the red-sensitive emulsion layer, a copolymer latex of methacrylic acid and butyl acrylate (weight ratio: 1:1, average molecular weight: 200,000 to 400,000) was added in an amount of 0.05 g/m$^2$.

To the second, fourth and sixth layers, disodium catechol-3,5-disulfonate was added to a coverage of 6 mg/m$^2$, 6 mg/m$^2$ and 18 mg/m$^2$, respectively.

For the anti-irradiation purpose, the dyes shown below (the coated amount is shown in the parenthesis) were added.

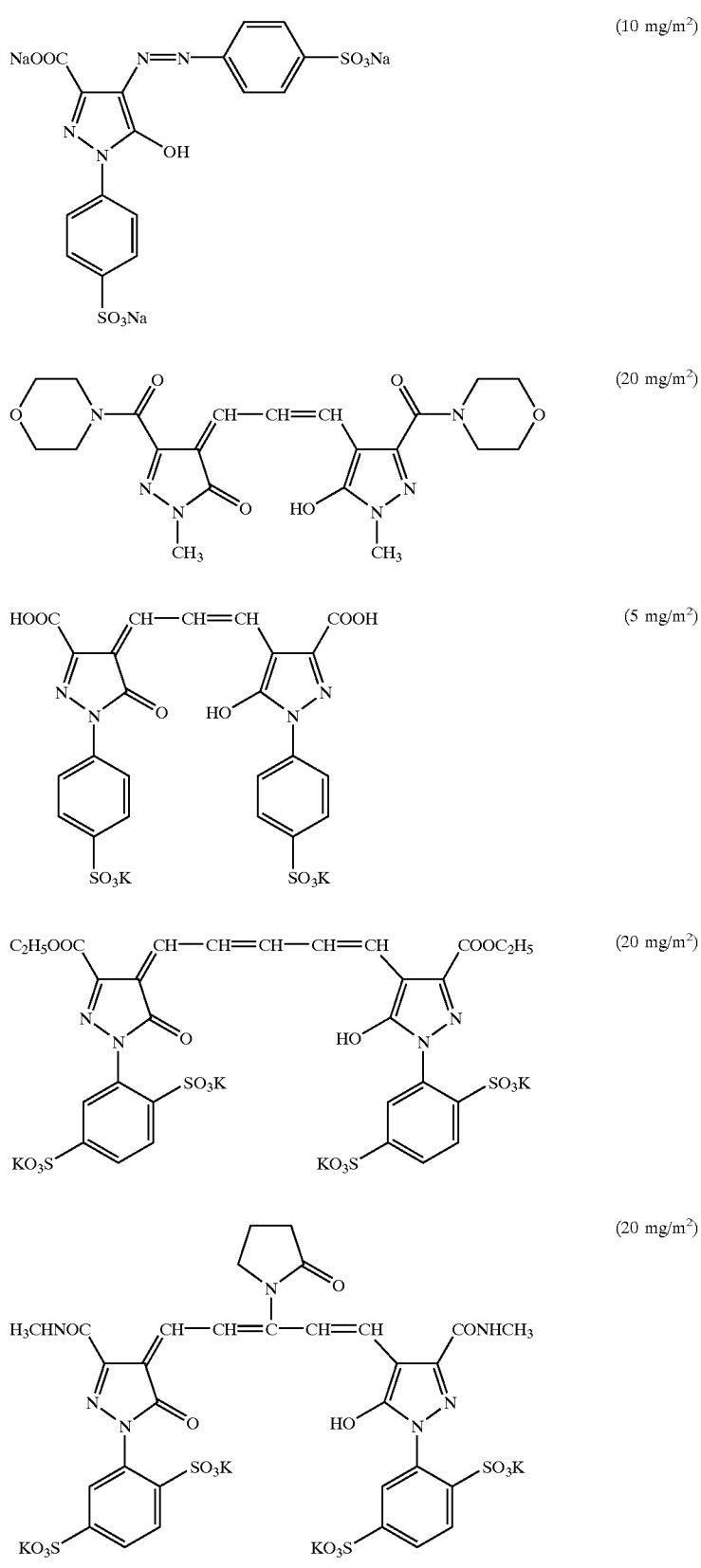

Layer Structure

Each layer structure is shown below. The numeral shows the coated amount (g/m$^2$). In the case of silver halide emulsions, the coated amount is a coated amount in terms of silver.

Support

Polyethylene resin laminated paper

[Polyethylene resin in the first layer side contains a white pigment (TiO$_2$, content: 16 wt %; ZnO, content: 4 wt %), a fluorescent whitening agent (4,4'-bis(5-methylbenzoxazolyl)stilbene, content: 0.03 wt %) and a bluish dye (ultramarine).]

First Layer (blue-sensitive emulsion layer):

| | |
|---|---|
| Silver Chlorobromide Emulsion A (cubic; a 5:5 (by mol as silver) mixture of Large-Size Emulsion A having an average grain size of 0.74 μm and Small-Size Emulsion A having an average grain size of 0.65 μm, where the coefficient of variation of the grain size distribution was 0.08 and 0.10, respectively; the emulsions of respective sizes containing 0.3 mol % of silver bronide partially localized on the surface of a grain using silver chloride as the substrate) | 0.24 |
| Gelatin | 1.25 |
| Yellow Coupler (ExY) | 0.57 |
| Dye Image Stabilizer (Cpd-1) | 0.07 |
| Dye Image Stabilizer (Cpd-2) | 0.04 |
| Dye Image Stabilizer (Cpd-3) | 0.07 |
| Solvent (Solv-1) | 0.21 |

Second Layer (color mixing inhibiting layer):

| | |
|---|---|
| Gelatin | 0.99 |
| Color Mixing Inhibitor (Cpd-4) | 0.09 |
| Color Mixing Inhibitor Aid (Cpd-5) | 0.018 |
| Stabilizer (Cpd-6) | 0.13 |
| Color Mixing Inhibitor (Cpd-7) | 0.01 |
| Solvent (Solv-1) | 0.06 |
| Solvent (Solv-2) | 0.22 |

Third Layer (green-sensitive emulsion layer):

| | |
|---|---|
| Silver Chlorobromide Emulsion A (cubic; a 1:3 (by mol as silver) mixture of Large-Size Emulsion B having an average grain size of 0.45 μm and Small-Size Emulsion B having an average grain size of 0.35 μm, where the coefficient of variation of the grain size distribution was 0.10 and 0.08, respectively; the emulsions of respective sizes containing 0.4 mol % of silver bronide partially localized on the surface of a grain using silver chloride as the substrate) | 0.14 |
| Gelatin | 1.36 |
| Magenta Coupler (ExM) | 0.15 |
| Ultraviolet Absorbent (UV-1) | 0.05 |
| Ultraviolet Absorbent (UV-2) | 0.03 |
| Ultraviolet Absorbent (UV-3) | 0.02 |
| Ultraviolet Absorbent (UV-4) | 0.04 |
| Dye Image Stabilizer (Cpd-2) | 0.02 |
| Color Mixing Inhibitor (Cpd-4) | 0.002 |
| Stabilizer (Cpd-6) | 0.09 |
| Dye Image Stabilizer (Cpd-8) | 0.02 |
| Dye Image Stabilizer (Cpd-9) | 0.03 |
| Dye Image Stabilizer (Cpd-10) | 0.01 |
| Dye Image Stabilizer (Cpd-11) | 0.0001 |
| Solvent (Solv-3) | 0.11 |
| Solvent (Solv-4) | 0.22 |
| Solvent (Solv-5) | 0.20 |

Fourth Layer (color mixing inhibiting layer):

| | |
|---|---|
| Gelatin | 0.71 |
| Color Mixing Inhibitor (Cpd-4) | 0.06 |
| Color Mixing Inhibitor Aid (Cpd-5) | 0.013 |
| Stabilizer (Cpd-6) | 0.10 |
| Color Mixing Inhibitor (Cpd-7) | 0.007 |
| Solvent (Solv-1) | 0.04 |
| Solvent (Solv-2) | 0.16 |

Fifth Layer (red-sensitive emulsion layer):

| | |
|---|---|
| Silver Chlorobromide Emulsion C (cubic; a 5:5 (by mol as silver) mixture of Large-Size Emulsion A having an average grain size of 0.40 μm and Small-Size Emulsion A having an average grain size of 0.30 μm, where the coefficient of variation of the grain size distribution was 0.09 and 0.11, respectively; the emulsions of respective sizes containing 0.5 mol % of silver bromide partially localized on the surface of a grain using silver chloride as the substrate) | 0.20 |
| Gelatin | 1.11 |
| Cyan Coupler (ExC) | 0.25 |
| Dye Image Stabilizer (Cpd-1) | 0.25 |
| Dye Image Stabilizer (Cpd-14) | 0.03 |
| Dye Image Stabilizer (Cpd-15) | 0.10 |
| Dye Image Stabilizer (Cpd-16) | 0.08 |
| Dye Image Stabilizer (Cpd-17) | 0.05 |
| Dye Image Stabilizer (Cpd-18) | 0.01 |
| Solvent (Solv-5) | 0.23 |

Sixth Layer (ultraviolet absorbing layer):

| | |
|---|---|
| Gelatin | 0.46 |
| Ultraviolet Absorbent (UV-1) | 0.14 |
| Ultraviolet Absorbent (UV-2) | 0.05 |
| Ultraviolet Absorbent (UV-3) | 0.04 |
| Ultraviolet Absorbent (UV-4) | 0.06 |
| Solvent (Solv-7) | 0.25 |

Seventh Layer (protective layer):

| | |
|---|---|
| Gelatin | 1.00 |
| Acryl-modified copolymer of polyvinyl alcohol (modification degree: 17%) | 0.04 |
| Liquid paraffin | 0.02 |
| Surface Active Agent (Cpd-13) | 0.01 |

Yellow Coupler (ExY)
A 60:40 (by mol) mixture of:
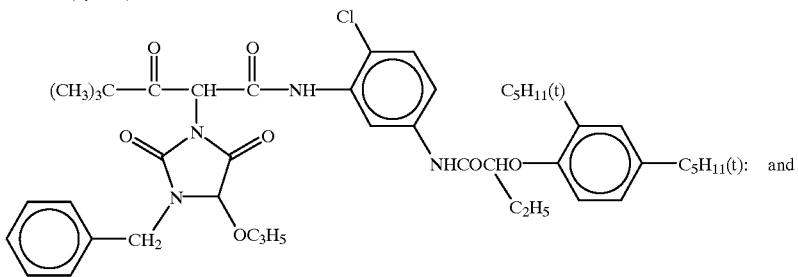
and
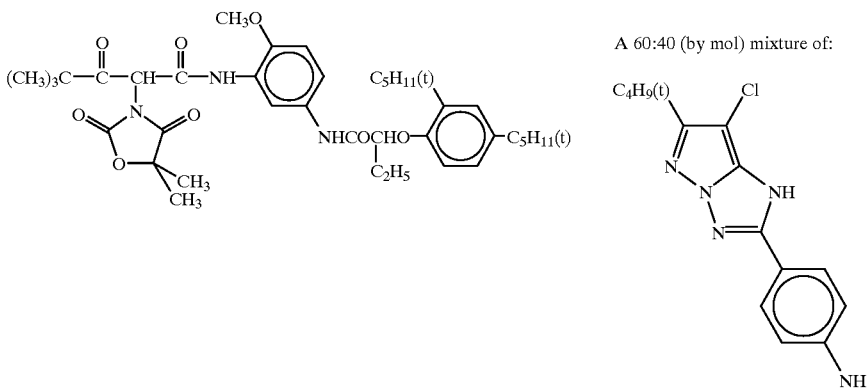
Magenta Coupler (ExM)
A 60:40 (by mol) mixture of:
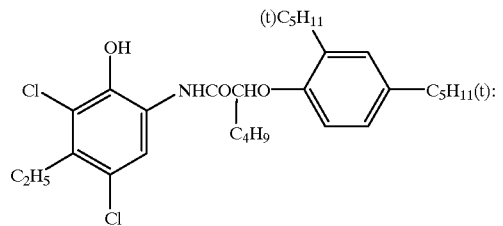
and
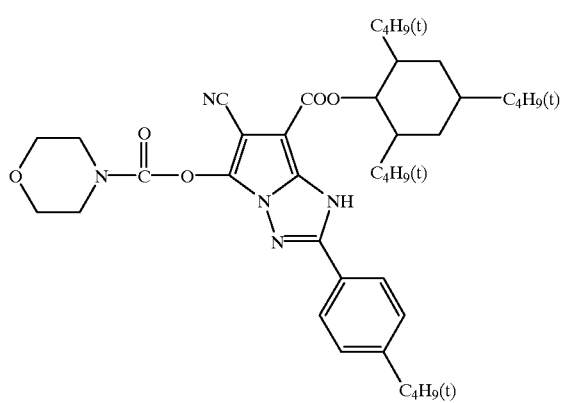
Cyan Coupler (ExC)
A 60:40 (by mol) mixture of C1 and C2
C1
C2
Dye Image Stabilizer (Cpd-1)
$-(CH_2-CH)_n-$
$\quad\quad\quad |$
$\quad\quad\;\; CONHC_4H_9(t)$
Number average molecular weight: 60,000

-continued
Dye Image Stabilizer (Cpd-2)
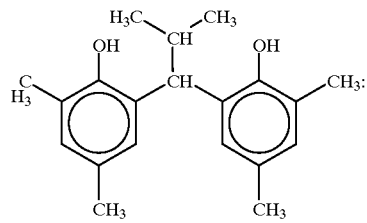
Dye Image Stabilizer (Cpd-3)
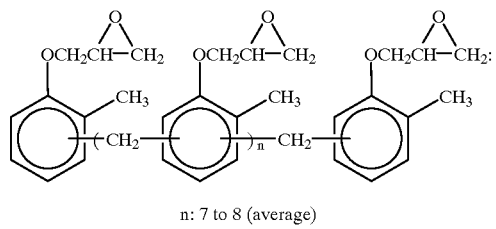
n: 7 to 8 (average)
Color Mixing Inhibitor (Cpd-4)
A 1:1:1 (by mol) mixture of
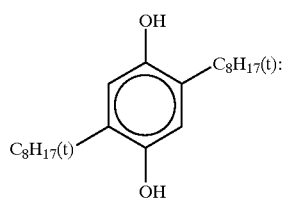
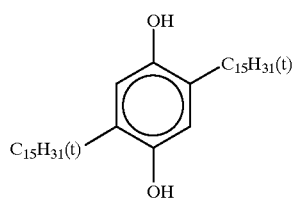
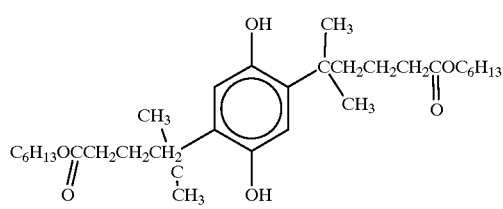
Color Mixing Inhibitory Aid (Cpd-5)
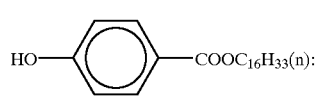
Stabilizer (Cpd-6)
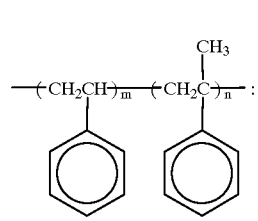
Number average molecular weight: 600
m/n = 10/90
Color Mixing Inhibitor (Cpd-7)
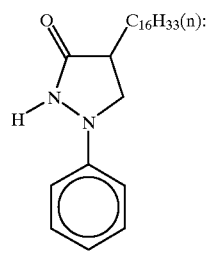
Dye Image Stabilizer (Cpd-8)
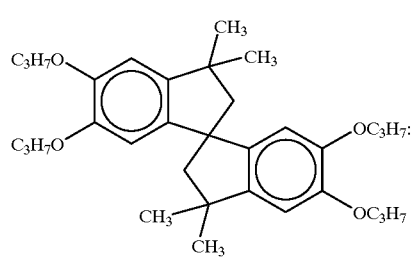
Dye Image Stabilizer (Cpd-9)
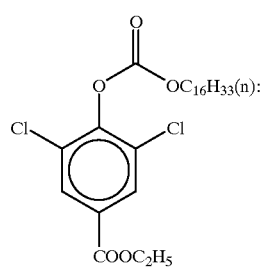
Dye Image Stabilizer (Cpd-10)
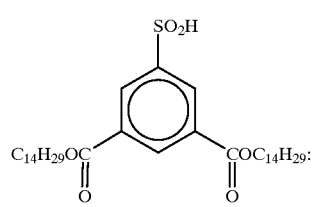
(Cpd-11)
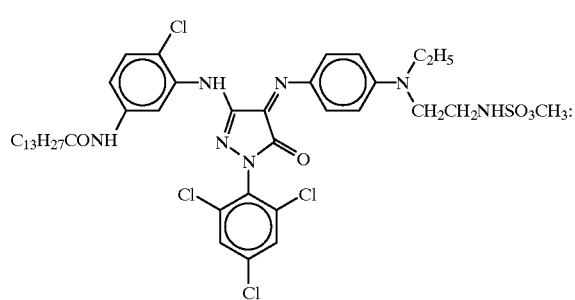

-continued
Dye Image Stabilizer (Cpd-12)
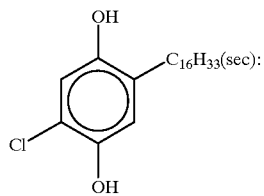
Surface Active Agent (Cpd-13)
A 7:3 (by mol) mixture of
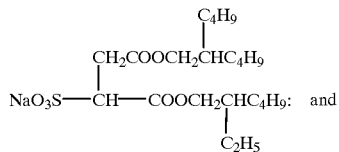 and
(Cpd-14)
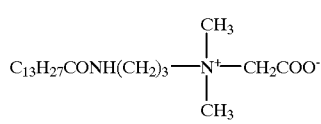
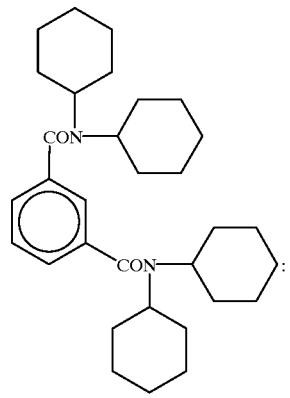
(Cpd-15)
A 1:1 (by mol) mixture of
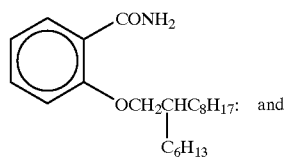 and
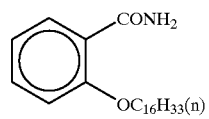
(Cpd-16)
(Cpd-17)
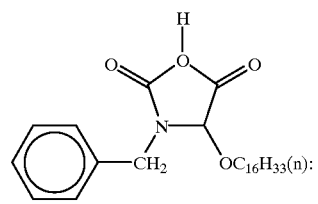
(Cpd-18)
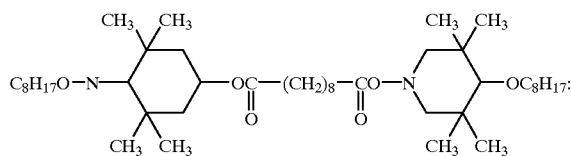
Ultraviolet Absorbent (UV-1)
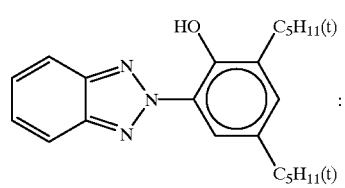
Ultraviolet Absorbent (UV-2)
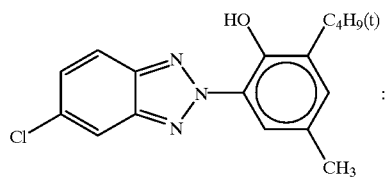
Ultraviolet Absorbent (UV-3)
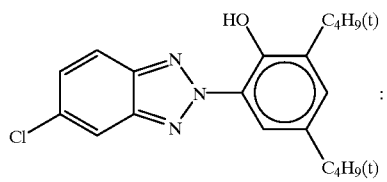

-continued

Ultraviolet Absorbent (UV-4)

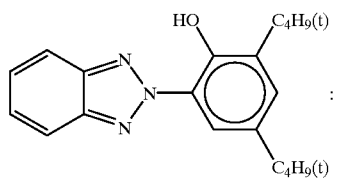

Ultraviolet Absorbent (UV-5)

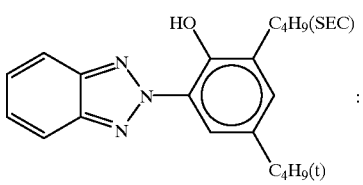

(Solv-1)

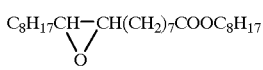

(Solv-2)

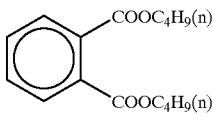

(Solv-3)

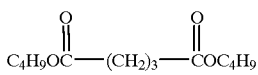

(Solv-4)

$O = P + OC_6H_{13}(n))_3$ (Solv-5)

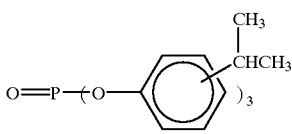

(Solv-6)

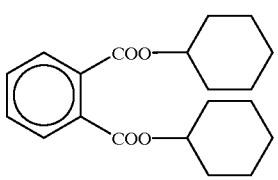

(Solv-7)

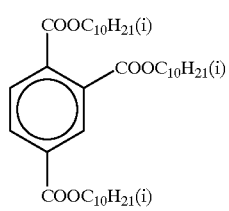

(Solv-8)

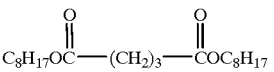

(Solv-9)

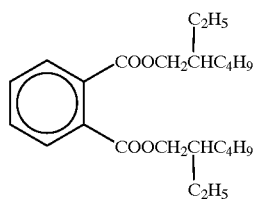

(3) Development Processing

The thus-prepared Light-Sensitive Sample P-1 was worked into a 127 mm-width roll and using Mini-Lab Printer Processor PP350 manufactured by Fuji Photo Film Co., Ltd., Light-Sensitive Sample P-1 was imagewise exposed from a negative film developed to finish with a standard color balance having an average density of 0.7 and then continuously processed until the volume of the color developer replenisher used in the following processing step became 0.5 times the volume of the color developing tank (running test).

| Processing Step | Temperature | Time | Replenishing Amount |
|---|---|---|---|
| Color development | 38.5° C. | 45 sec | 45 mL |
| Bleach-fixing | 38.0° C. | 45 sec | 35 mL |
| Rinsing 1 | 38.0° C. | 20 sec | — |
| Rinsing 2 | 38.0° C. | 20 sec | — |

-continued

| Processing Step | Temperature | Time | Replenishing Amount |
|---|---|---|---|
| Rinsing 3 | 38.0° C. | 20 sec | — |
| Rinsing 4 | 38.0° C. | 20 sec | 121 ml |
| Drying | 80° C. | | |

(Note)
*Replenishing amount was per 1 m² of the light-sensitive material
**Rinse Screening System RC50D manufactured by Fuji Photo Film Co., Ltd. was mounted on Rinse (3) and a rinsing solution was taken out from Rinse (3) and sent by a pump to a reverse osmosis module (RC50D). The permeable water sent from the tank was fed to Rinse (4) and the concentrated solution was returned to Rinse (3). The pump pressure was adjusted such that the permeable water to the reverse osmosis module was kept in an amount of 50 to 300 mL/min. The circulation was continued under temperature control for 10 hours per day. The rinsing employed a four tank counter-current system from (1) to (4).

rinsing solution was taken out from Rinse (3) and sent by a pump to a reverse osmosis module (RC50D). The permeable water sent from the tank was fed to Rinse (4) and the concentrated solution was returned to Rinse (3). The pump pressure was adjusted such that the permeable water to the reverse osmosis module was kept in an amount of 50 to 300 mL/min. The circulation was continued under temperature control for 10 hours per day. The rinsing employed a four tank counter-current system from (1) to (4).

Each processing solution had the following composition.

| [Color Developer] | [Tank Solution] |
|---|---|
| Water | 800 mL |
| Compound of the present invention or Comparative Compound | 2 mmol |
| Fluorescent brightening agent (FL-1) | 0.35 g |
| Triisopropanolamine | 8.8 g |
| Polyethylene glycol (average molecular weight: 300) | 10.0 g |
| Ethylenediaminetetraacetic acid | 4.0 g |
| Sodium sulfite | 0.10 g |
| Potassium chloride | 10.0 g |
| Sodium 4,5-dihydroxybenzene-1,3-disulfonate | 0.50 g |
| Disodium N,N-bis(sulfonatoethyl)-hydroxylamine | 8.5 g |
| 4-Amino-3-methyl-N-ethyl-N-(β-methanesulfonamidoethyl) aniline 3/2-sulfonate monohydrate | 4.8 g |
| Potassium carbonate | 26.3 g |
| Water to make a total of | 1,000 mL |
| pH (at 25° C., adjusted by sulfuric acid and KOH) | 10.15 |

The color developer replenisher used was obtained by 3.8-fold diluting the color developing composition prepared in (1) with water.

| | [Tank Solution] | [Replenisher] |
|---|---|---|
| [Bleach-Fixing Solution] | | |
| Water | 800 mL | 800 mL |
| Ammonium thiosulfate (750 g/mL) | 107 mL | 214 mL |
| m-Carboxybenzenesulfinic acid | 8.3 g | 16.5 g |
| Fe(III) ammonium ethylenediaminetetraacetate | 47.0 g | 94.0 g |
| Ethylenediaminetetraacetic acid | 1.4 g | 2.8 g |
| Nitric acid (67%) | 16.5 g | 33.0 g |
| Imidazole | 14.6 g | 29.2 g |
| Ammonium sulfite | 16.0 g | 32.0 g |
| Potassium metabisulfite | 23.1 g | 46.2 g |
| Water to make a total of | 1,000 mL | 1,000 mL |
| pH (at 25° C., adjusted by nitric acid and aqueous ammonia) | 6.5 | 6.5 |
| [Rising Solution] | | |
| Chlorinated sodium isocyanurate | 0.02 g | 0.02 g |
| Deionized water (electrical conductivity: 5 μs/cm or less) | 1,000 mL | 1,000 mL |
| pH (at 25° C.,) | 6.5 | 6.5 |

(4) Evaluation
1) Stability against Deposition of Precipitates

The prepared color developing composition was poured into a glass bottle and stored at −5° C. or room temperature for 4 weeks. The test results were evaluated by visually judging the liquid state after aging according to a 5-level evaluation such that the level of conspicuous precipitation was xx, the level of apparent precipitation was x, the level of slight precipitation was Δ, the level of no precipitation but clouding was O and the level of complete transparency with neither clouding nor precipitation was OO.

2) Photographic Properties in Color Paper Processing

An unexposed light-sensitive material sample was subjected to a development processing and the reflection spectrum thereof was measured using a spectrophotometer (Model U-3500, manufactured by Hitachi Ltd.) on which a 150-mmφ integrating sphere was mounted. The absorbancy at 450 nm was designated as $D_B$. This sample was then washed with distilled water at 40° C. and dried. Thereafter, the same measurement was performed and the absorbancy at 450 nm here was designated as $D_{BW}$.

$\Delta D_B$ was determined according to the following formula and from the obtained value, the degree of staining ascribable to the residual sensitizing dyes was evaluated.

$$\Delta D_B = D_B - D_{BW}$$

3) Results

TABLE 1

| Sample | Compound Added | Amount Added (mmol) | Evaluation of Deposition (−5° C.) | Evaluation of Deposition (room temperature) | Evaluation of Photographic Properties ($\Delta D_B$) | Remarks |
|---|---|---|---|---|---|---|
| 1-1 | none | — | OO | OO | 0.020 | Comparison |
| 1-2 | FL-2 | 15 | XX | X | 0.005 | Comparison |
| 1-3 | FL-3 | 15 | OO | OO | 0.038 | Comparison |
| 1-4 | A-2 | 15 | OO | OO | 0.004 | Invention |
| 1-5 | A-3 | 15 | OO | OO | 0.003 | Invention |
| 1-6 | A-23 | 15 | OO | OO | 0.006 | Invention |
| 1-7 | A-33 | 15 | OO | OO | 0.003 | Invention |
| 1-8 | A-34 | 15 | OO | OO | 0.003 | Invention |

In the case of Sample 1-2 (comparison) using Comparative Compound FL-2, the staining ascribable to residual sensitizing dyes is on the level equal or close to the staining in the samples using the compound of the present invention, however, precipitation is generated in aging of the processing composition. This precipitation is ascribable to the compound added, because in Sample 1-1 (comparison), precipitation does not occur.

In the case of Sample 1-3 (comparison) using Comparative Compound FL-3, the stability against deposition of precipitates was high similarly to the samples using the compound of the present invention, however, the staining is rather increased.

In the light-sensitive materials of which development processing is performed using the processing composition of the present invention, the staining $D_B$ ascribable to residual sensitizing dyes is small, namely, coloring of the white background is reduced. At the same time, the processing composition is completely transparent at room temperature after the passing of 4 weeks. Even at a low temperature (−5° C.), the processing composition is completely transparent or slightly turbid and precipitation is not generated. From these results, it is verified that the processing composition of the present invention has an excellent effect of reducing the staining ascribable to residual sensitizing dyes of a light-sensitive material and can be free of deposition of precipitates during the storage of the composition at low temperatures.

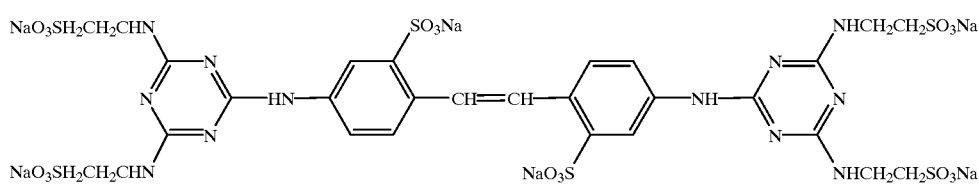

FL-2

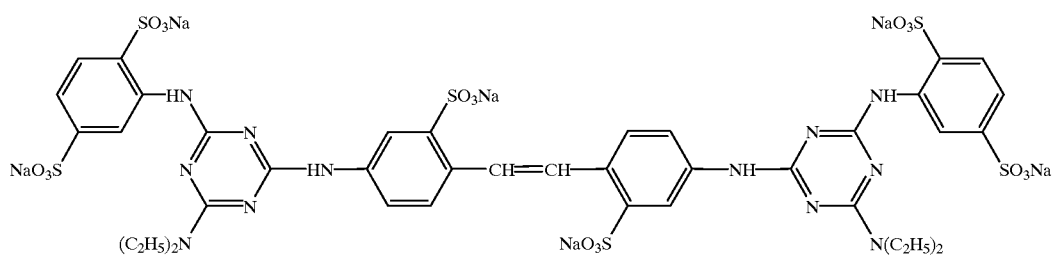

FL-3

EXAMPLE 2
(1) Preparation of Color Developing Composition

| Compound of the present invention | see Table 2 |
| --- | --- |
| Fluorescent brightening agent (FL-4) | 3.5 g |
| Fluorescent brightening agent (FL-5) | 3.5 g |
| Triisopropanolamine | 40.0 g |
| Ethylenediaminetetraacetic acid | 15.0 g |
| Sodium sulfite | 0.80 g |
| Sodium p-toluenesulfonate | 75.0 g |
| Sodium 4,5-dihydroxybenzene-1,3-disulfonate | 2.0 g |
| Disodium N,N-bis(sulfonatoethyl)hydroxylamine | 55.0 g |
| 4-Amino-3-methyl-N-ethyl-N-(β-methanesulfonamidoethyl)aniline.3/2 sulfate.monohydrate | 85.0 g |
| Potassium hydroxide | 34.5 g |
| Sodium hydroxide | 25.0 g |
| Potassium carbonate | 100.0 g |
| Water to make a total of | 1,000 mL |
| PH | 13.2 |

(2) Preparation of Light-Sensitive Material Sample

The same light-sensitive material as in Example 1, namely, Sample P-1 was used.

(3) Development Processing

The Light-Sensitive sample P-1 was worked into a 127 mm-width roll and using an experimental processing apparatus obtained by modifying Mini-Lab Printer Processor PP350 manufactured by Fuji Photo Film Co., Ltd. so that the processing time and the processing temperature could be varied, the light-sensitive sample was imagewise exposed through a developed negative film having a standard color balance with an average density of 0.7 and then continuously processed until the volume of the, color developer replenisher used in the following processing step became 0.5 times the volume of the color developing tank (running test).

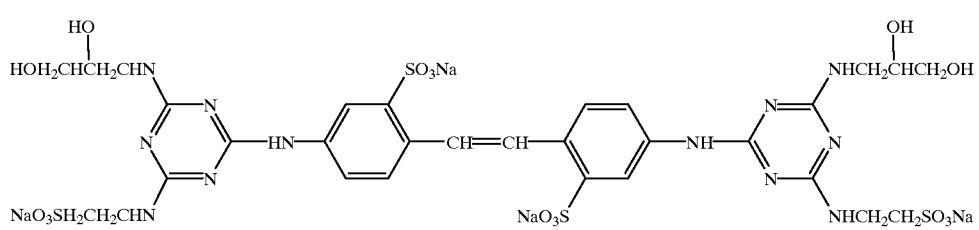

FL-4

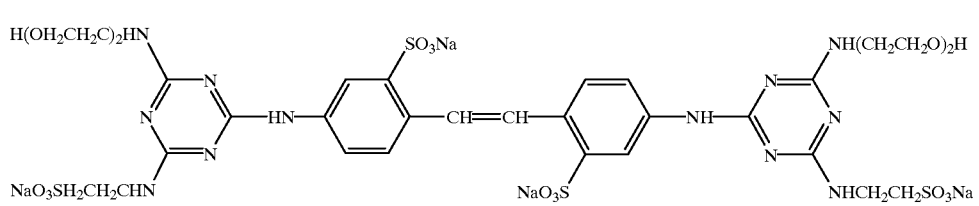

FL-5

| Processing Step | Temperature | Time | Replenishing Amount |
|---|---|---|---|
| Color development | 45.0° C. | 15 sec | 45 mL |
| Bleach-fixing | 40.0° C. | 15 sec | 35 mL |
| Rinsing 1 | 40.0° C. | 8 sec | — |
| Rinsing 2 | 40.0° C. | 8 sec | — |
| Rinsing 3 | 40.0° C. | 8 sec | — |
| Rinsing 4 | 38.0° C. | 8 sec | 121 ml |
| Drying | 80° C. | 15 sec | |

(Note)
*Replenishing amount was per 1 m² of the light-sensitive material
**Rinse Screening System RC50D manufactured by Fuji Photo Film Co., Ltd. was mounted on Rinse (3) and a rinsing solution was taken out from Rinse (3) and sent by a pump to a reverse osmosis module (RC50D). The permeable water sent from the tank was fed to Rinse (4) and the concentrated solution was returned to Rinse (3). The pump pressure was adjusted such that the permeable water to the reverse osmosis module was kept in an amount of 50 to 300 mL/min. The circulation was continued under temperature control for 10 hours per day. The rinsing employed a four tank counter-current system from (1) to (4).

Each processing solution had the following composition.

| [Color Developer] | [Tank Solution] |
|---|---|
| Water | 800 mL |
| Compound of the present invention | 4 mmol |
| Fluorescent brightening agent (FL-4) | 0.50 g |
| Fluorescent brightening agent (FL-5) | 0.50 g |
| Triisopropanolamine | 8.8 g |
| Sodium p-toluenesulfonate | 20.0 g |
| Ethylenediaminetetraacetic acid | 4.0 g |
| Sodium sulfite | 0.10 g |
| Potassium chloride | 10.0 g |
| Sodium 4,5-dihydroxybenzene-1,3-disulfonate | 0.50 g |
| Disodium N,N-bis(sulfonatoethyl)-hydroxylamine | 8.5 g |
| 4-Amino-3-methyl-N-ethyl-N-(β-methanesulfonamidoethyl)aniline.3/2 sulfate.monohydrate | 10.0 g |
| Potassium carbonate | 26.3 g |
| Water to make a total of | 1,000 ml |
| pH (at 25° C., adjusted by sulfuric acid and KOH) | 10.35 |

The color developer replenisher used was obtained by 3.8-fold diluting the color developing composition prepared in (1) with water.

| [Bleach-Fixing Solution] | [Tank Solution] | [Replenisher] |
|---|---|---|
| Water | 800 mL | 800 mL |
| Ammonium thiosulfate (750 g/mL) | 107 mL | 214 mL |
| Succinic acid | 29.5 g | 59.0 g |
| Fe (III) ammonium ethylene-diaminetetraacetate | 47.0 g | 94.0 g |
| Ethylenediaminetetraacetic acid | 1.4 g | 2.8 g |
| Nitric acid (67%) | 17.5 g | 35.0 g |
| Imidazole | 14.6 g | 29.2 g |
| Ammonium sulfite | 16.0 g | 32.0 g |
| Potassium metabisulfite | 23.1 g | 46.2 g |
| Water to make a total of | 1,000 mL | 1,000 mL |
| pH (at 25° C., adjusted by nitric acid and aqueous ammonia) | 6.00 | 6.00 |

| [Rinsing Solution] | [Tank Solution] | [Replenisher] |
|---|---|---|
| Chlorinated sodium isocyanurate | 0.02 g | 0.02 g |
| Deionized water (electrical conductivity: 5 μs/cm or less) | 1,000 mL | 1,000 mL |
| pH (at 25° C.) | 6.5 | 6.5 |

(4) Evaluation

The processed light-sensitive materials were evaluated in the same manner as in Example 1.

TABLE 2

| Sample | Compound Added | Amount Added (mmol) | Evaluation of Deposition (−5° C.) | Evaluation of Deposition (room temperature) | Evaluation of Photographic Properties ($\Delta D_B$) | Remarks |
|---|---|---|---|---|---|---|
| 2-1 | none | — | OO | OO | 0.012 | Comparison |
| 2-2 | FL-2 | 25 | XX | XX | 0.004 | Comparison |
| 2-3 | FL-3 | 25 | O | OO | 0.045 | Comparison |
| 2-4 | A-2 | 25 | OO | OO | 0.003 | Invention |
| 2-5 | A-3 | 25 | OO | OO | 0.003 | Invention |
| 2-6 | A-23 | 25 | O | OO | 0.006 | Invention |
| 2-7 | A-33 | 25 | OO | OO | 0.002 | Invention |
| 2-8 | A-34 | 25 | OO | OO | 0.002 | Invention |

Even when a color developing composition increased in the developing agent concentration is prepared and the processing is performed within a shortened time, the processing composition of the present invention can give a finish reduced in the staining $\Delta D_B$ ascribable to residual sensitizing dyes. Furthermore, even after the passing of 4 weeks, the processing compound is completely transparent at room temperature and even at a low temperature (−5° C.), precipitation is not generated at all. From these results, the processing composition of the present invention is verified to have suitability for rapid processing of color paper.

EXAMPLE 3

(1) Preparation of Fixing Composition

| | |
|---|---|
| Compound of the present invention | see Table 6 |
| Ammonium bisulfite solution (65%) | 65.0 g |
| Aqueous ammonium thiosulfate solution (750 g/L) | 840 mL |
| Imidazole | 40.0 g |
| Water to make a total of | 1,000 mL |
| PH | 7.00 |

(2) Light-Sensitive Material
1) Preparation of Emulsion (2) Light-Sensitive Material
1) Preparation of Emulsion
Silver Halide Emulsions Em-A to Em-O were prepared by the following production method.
Preparation of Em-A
1,200 mL of an aqueous solution containing 1.0 g of a low molecular weight gelatin having a molecular weight of 15,000 and 1.0 g of KBr was vigorously stirred while keeping at 35° C. Thereto, 30 mL of an aqueous solution containing 1.9 g of silver nitrate and 30 mL of an aqueous solution containing 1.5 g of KBr and 0.7 g of a low molecular weight gelatin having a molecular weight of 15,000 were added by a double jet method over 30 seconds to perform the nucleation. At this time, the excess concentration of KBr was kept constant. Then, the resulting solution was ripened by adding 6 g of KBr and elevating the temperature to 75° C. After the completion of ripening, 35 g of succinated gelatin was added and the pH was adjusted to 5.5. Thereto, 150 mL of an aqueous solution containing 30 g of silver nitrate and an aqueous KBr solution were added by a double jet method over 16 minutes. At this time, the silver potential was kept at −25 mV to the saturated calomel electrode. Furthermore, an aqueous solution containing 110 g of silver nitrate and an aqueous KBr solution were added by a double jet method over 15 minutes while accelerating the flow rate such that the final flow rate was 1.2 times the initial flow rate. At this time, an AgI fine grain emulsion having a size of 0.03 μm was simultaneously added to have a silver iodide content of 3.8% while accelerating the flow rate and keeping the silver potential at −25 mV. Thereto, 132 mL of an aqueous solution containing 35 g of silver nitrate and an aqueous KBr solution were added by a double jet method over 7 minutes. The addition of the aqueous KBr solution was controlled such that the potential was −20 mV at the completion of addition. After elevating the temperature to 40° C., 5.6 g (in terms of KI) of Compound 1 was added and then 64 mL of an aqueous 0.8 M sodium sulfite solution was added. Furthermore, the pH was elevated to 9.0 by adding an aqueous NaOH solution and kept for 4 minutes to abruptly produce iodide ion. Thereafter, the pH was returned to 5.5, the temperature was returned to 55° C., and then 1 mg of sodium benzenethiosulfonate was added. Furthermore, 13 g of lime-processed gelatin having a calcium concentration of 1 ppm was added. After the completion of addition, 250 mL of an aqueous solution containing 70 g of silver nitrate and an aqueous KBr solution were added over 20 minutes while keeping the potential at 60 mV. At this time, yellow prussiate of potash was added in an amount of $1.0 \times 10^{-5}$ mol per mol of silver. The obtained emulsion was washed with water and after adding 60 g of lime-processed gelatin having a calcium concentration of 1 ppm, the pH and the pAg were adjusted at 40° C. to 5.8 and 8.7, respectively.

Compound 1

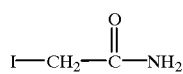

The calcium, magnesium and strontium contents of the thus-obtained emulsion were measured by the ICP emission spectrometry and found to be 15 ppm, 2 ppm and 1 ppm, respectively.

The temperature of the emulsion obtained above was elevated to 56° C. Thereto, 1 g (in terms of Ag) of a pure AgBr fine grain emulsion having a size of 0.05 μm was added to form a shell. Then, Sensitizing dyes 1, 2 and 3 each in the solid fine dispersion form were added in an amount of $5.85 \times 10^{-4}$ mol, $3.06 \times 10^{-4}$ mol and $9.00 \times 10^{-6}$ mol, per mol of silver. The solid fine dispersions of Sensitizing dyes 1, 2 and 3 were prepared as follows. As shown in the preparation conditions of Table 3, an inorganic salt was dissolved in ion exchanged water and a sensitizing dye was added thereto and dispersed at 60° C. using a dissolver blade at 2,000 rpm for 20 minutes to obtain a solid fine dispersion of Sensitizing Dye 1, 2 or 3. When the sensitizing dyes were added and the adsorption of sensitizing dye reached 90% of the adsorption amount in the equilibrium state, calcium nitrate was added to make a calcium concentration of 250 ppm. The adsorption amount was obtained by separating the solid layer and the liquid layer by centrifugal precipitation, measuring the difference between the amount of sensitizing dye initially added and the amount of sensitizing dye in the supernatant and determining the amount of sensitizing dye adsorbed. After calcium nitrate was added, potassium thiocyanate, chloroauric acid, sodium thiosulfate, N,N-dimethylselenourea and Compound 4 were added to optimally perform the chemical sensitization. The N,N-dimethylselenourea was added in an amount of $3.40 \times 10^{-6}$ mol per mol of silver. After the completion of chemical sensitization, Compounds 2 and 3 were added and thereby Em-A was prepared.

TABLE 3

| Sensitizing Dye | Amount of Sensitizing Dye | NaNO$_3$/ Na$_2$SO$_4$ | Water | Dispersion Time | Dispersion Temperature |
| --- | --- | --- | --- | --- | --- |
| 1 | 3 parts by mass | 0.8 parts by mass/ 3.2 parts by mass | 43 parts by mass | 20 min. | 60° C. |
| 2 | 4 parts by mass | 0.6 parts by mass/ 2.4 parts by mass | 42.8 parts by mass | 20 min. | 60° C. |
| 3 | 0.12 parts by mass | 0.6 parts by mass/ 2.4 parts by mass | 42.8 parts by mass | 20 min. | 60° C. |

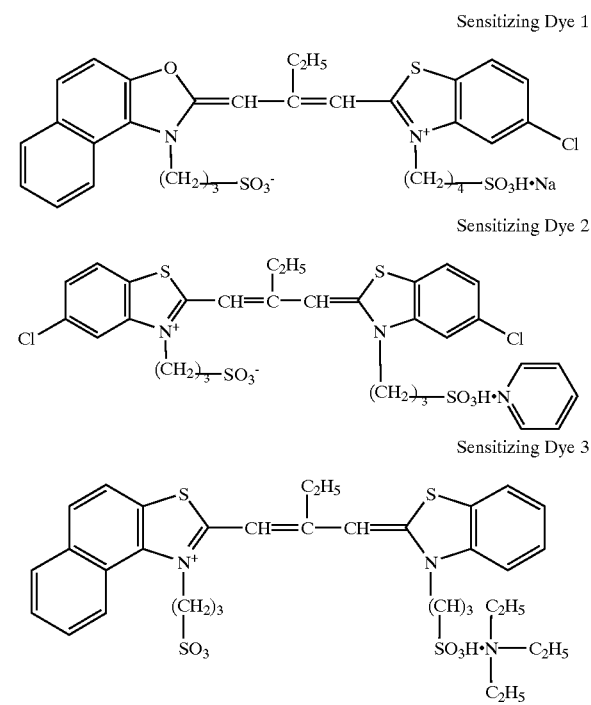

-continued

Compound 2

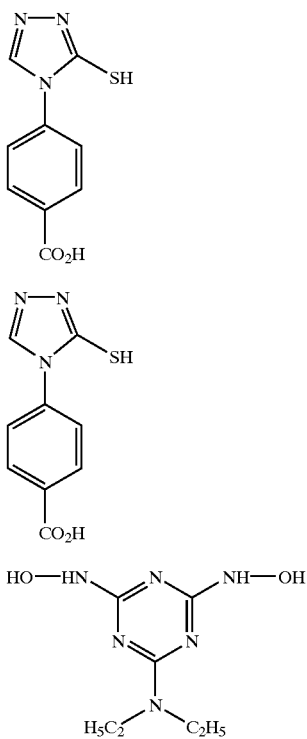

Compound 3

Compound 4

Compound 6

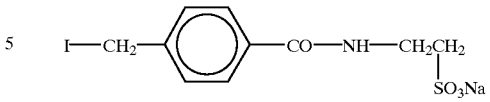

Preparation of Em-E 1,200 mL of an aqueous solution containing 1.0 g of a low molecular weight gelatin having a molecular weight of 15,000 and 1.0 g of KBr was vigorously stirred while keeping at 35° C. Thereto, 30 mL of an aqueous solution containing 1.9 g of silver nitrate and 30 mL of an aqueous solution containing 1.5 g of KBr and 0.7 g of a low molecular weight gelatin having a molecular weight of 15,000 were added by a double jet method over 30 seconds to perform the nucleation. At this time, the excess concentration of KBr was kept constant. Then, the resulting solution was ripened by adding 6 g of KBr and elevating the temperature to 75° C. After the completion of ripening, 15 g of succinated gelatin and 20 g of the above-described trimellited gelatin were added and the pH was adjusted to 5.5. Thereto, 150 mL of an aqueous solution containing 30 g of silver nitrate and an aqueous KBr solution were added by a double jet method over 16 minutes. At this time, the silver potential was kept at −25 mV to the saturated calomel electrode. Furthermore, an aqueous solution containing 110 g of silver nitrate and an aqueous KBr solution were added by a double jet method over 15 minutes while accelerating the flow rate such that the final flow rate was 1.2 times the initial flow rate. At this time, an AgI fine grain emulsion having a size of 0.03 $\mu$m was simultaneously added to have a silver iodide content of 3.8% while accelerating the flow rate and keeping the silver potential at −25 mV. Thereto, 132 mL of an aqueous solution containing 35 g of silver nitrate and an aqueous KBr solution were added by a double jet method over 7 minutes. The addition of the aqueous KBr solution was controlled such that the potential was −20 mV at the completion of addition. After adding KBr to adjust the potential to −60 mV, 1 mg of sodium benzenethiosulfonate was added and then, 13 g of lime-processed gelatin having a calcium concentration of 1 ppm was added. After the completion of addition, 250 mL of an aqueous solution containing 70 g of silver nitrate and an aqueous KBr solution were added over 20 minutes at a potential kept to −60 mV while continuously adding 8.0 g (in terms of KI) of an AgI fine grain emulsion having an equivalent-sphere diameter of 0.008 $\mu$m, which was prepared immediately before the addition by mixing an aqueous solution of a low molecular weight gelatin having a molecular weight of 15,000, an aqueous silver nitrate solution and an aqueous KS solution in a separate chamber having a magnetic coupling induction-type stirrer described in JP-A-10-43570. At this time, yellow prussiate of potash was added in an amount of $1.0 \times 10^{-5}$ mol per mol of silver. The obtained emulsion was washed with water and after adding 80 g of lime-processed gelatin having a calcium concentration of 1 ppm, the pH and the pAg were adjusted at 40° C. to 5.8 and 8.7, respectively.

The calcium, magnesium and strontium contents of the thus-obtained emulsion were measured by the ICP emission spectrometry and found to be 15 ppm, 2 ppm and 1 ppm, respectively.

The chemical sensitization was performed in the same manner as in Em-A except that Sensitizing Dyes 1, 2 and 3 were replaced by Sensitizing Dyes 4, 5 and 6 and the amounts added were changed to $7.73 \times 10^{-4}$ mol, $1.65 \times 10^{-4}$ mol and $6.20 \times 10^{-5}$ mol, and thereby Em-E was prepared.

Preparation of Em-B

Em-3 was prepared in the same manner as Em-A except that in the preparation of Em-A, the amount of KBr added after the nucleation was changed to 5 g, the succinated gelatin was replaced by trimellited gelatin containing 35 $\mu$mol/g of methionine and having a molecular weight of 100,000 and a trimellitation percentage of 98%, the amounts of sensitizing dyes added before the chemical sensitization were changed to $6.50 \times 10^{-4}$ mol, $3.40 \times 10^{-4}$ mol and $1.00 \times 10^{-5}$ mol for Sensitizing Dyes 1, 2 and 3, respectively, and the amount of N,N-dimethylselenourea added at the chemical sensitization was changed to $4.00 \times 10^{-6}$ mol.

Compound 5

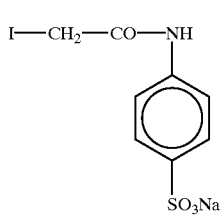

Preparation of Em-C

Em-C was prepared in the same manner as Em-A except that in the preparation of Em-A, the amount of KBr added after the nucleation was changed to 1.5 g, the succinated gelatin was replaced by phthalated gelatin containing 35 $\mu$mol/g of methionine and having a molecular weight of 100,000 and a phthalation percentage of 97%, Compound 1 was replaced by 7.1 g (in terms of KI) of Compound 7, the amounts of sensitizing dyes added before the chemical sensitization were changed to $7.80 \times 10^{-4}$ mol, $4.08 \times 10^{-4}$ mol and $1.20 \times 10^{-5}$ mol for Sensitizing Dyes 1, 2 and 3, respectively, and the amount of N,N-dimethylselenourea added at the chemical sensitization was changed to $5.00 \times 10^{-6}$ mol.

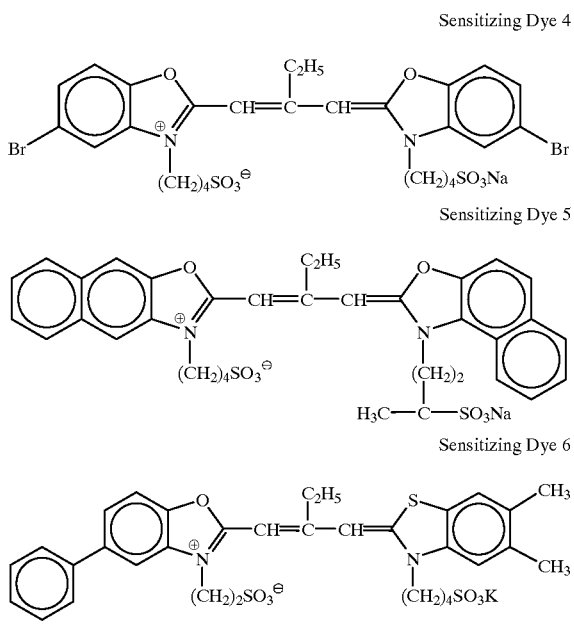

Sensitizing Dye 4

Sensitizing Dye 5

Sensitizing Dye 6

Preparation of Em-F 1,200 mL of an aqueous solution containing 1.0 g of a low molecular weight gelatin having a molecular weight of 15,000 and 1.0 g of KBr was vigorously stirred while keeping at 35° C. Thereto, 30 mL of an aqueous solution containing 1.9 g of silver nitrate and 30 mL of an aqueous solution containing 1.5 g of KBr and 0.7 g of a low molecular weight gelatin having a molecular weight of 15,000 were added by a double jet method over 30 seconds to perform the nucleation. At this time, the excess concentration of KBr was kept constant. Then, the resulting solution was ripened by adding 5 g of KBr and elevating the temperature to 75° C. After the completion of ripening, 20 g of succinated gelatin and 15 g of the phthalated gelatin were added and the pH was adjusted to 5.5. Thereto, 150 mL of an aqueous solution containing 30 g of silver nitrate and an aqueous KBr solution were added by a double jet method over 16 minutes. At this time, the silver potential was kept at −25 mV to the saturated calomel electrode. Furthermore, an aqueous solution containing 110 g of silver nitrate and an aqueous KBr solution were added by a double jet method over 15 minutes while accelerating the flow rate such that the final flow rate was 1.2 times the initial flow rate. At this time, an AgI fine grain emulsion having a size of 0.03 $\mu$m was simultaneously added to have a silver iodide content of 3.8% while accelerating the flow rate and keeping the silver potential at −25 mV. Thereto, 132 mL of an aqueous solution containing 35 g of silver nitrate and an aqueous KBr solution were added by a double jet method over 7 minutes. After adding an aqueous KBr solution to adjust the potential to −60 mV, 9.2 g (in terms of KI) of an AgI fine grain emulsion having a size of 0.03 $\mu$m was added. Furthermore, 1 mg of sodium benzenethiosulfonate was added and then 13 g of lime-processed gelatin having a calcium concentration of 1 ppm was added. After the completion of addition, 250 mL of an aqueous solution containing 70 g of silver nitrate and an aqueous KBr solution were added over 20 minutes while keeping the potential at 60 mV. At this time, yellow prussiate of potash was added in an amount of $1.0 \times 10^{-5}$ mol per mol of silver. The obtained emulsion was washed with water and after adding 80 g of lime-processed gelatin having a calcium concentration of 1 ppm, the pH and the pAg were adjusted at 40° C. to 5.8 and 8.7, respectively.

The calcium, magnesium and strontium contents of the thus-obtained emulsion were measured by the ICP emission spectrometry and found to be 15 ppm, 2 ppm and 1 ppm, respectively.

The chemical sensitization was performed in the same manner as in Em-B except that Sensitizing Dyes 1, 2 and 3 were replaced by Sensitizing Dyes 4, 5 and 6 and the amounts added were changed to $8.50 \times 10^{-4}$ mol, $1.82 \times 10^{-4}$ mol and $6.82 \times 10^{-5}$ mol, respectively, and thereby Em-F was prepared.

Preparation of Em-G 1,200 mL of an aqueous solution containing 1.0 g of a low molecular weight gelatin having a molecular weight of 15,000 and 1.0 g of KBr was vigorously stirred while keeping at 35° C. Thereto, 30 mL of an aqueous solution containing 1.9 g of silver nitrate and 30 mL of an aqueous solution containing 1.5 g of KBr and 0.7 g of a low molecular weight gelatin having a molecular weight of 15,000 were added by a double jet method over 30 seconds to perform the nucleation. At this time, the excess concentration of KBr was kept constant. Then, the resulting solution was ripened by adding 1.5 g of KBr and elevating the temperature to 75° C. After the completion of ripening, 15 g of the above-described trimellited gelatin and 20 g of the above-described phthalated gelatin were added and the pH was adjusted to 5.5. Thereto, 150 mL of an aqueous solution containing 30 g of silver nitrate and an aqueous KBr solution were added by a double jet method over 16 minutes. At this time, the silver potential was kept at −25 mV to the saturated calomel electrode. Furthermore, an aqueous solution containing 110 g of silver nitrate and an aqueous KBr solution were added by a double jet method over 15 minutes while accelerating the flow rate such that the final flow rate was 1.2 times the initial flow rate. At this time, an. AgI fine grain emulsion having a size of 0.03 $\mu$m was simultaneously added to have a silver iodide content of 3.8% while accelerating the flow rate and keeping the silver potential at −25 mV. Thereto, 132 mL of an aqueous solution containing 35 g of silver nitrate and an aqueous KBr solution were added by a double jet method over 7 minutes. The addition of the aqueous KBr solution was controlled to adjust the potential at −60 mV. Thereafter, 7.1 g (in terms of KI) of an AgI fine grain emulsion having a size of 0.03 $\mu$m was added. Furthermore, 1 mg of sodium benzenethiosulfonate was added and then, 13 g of lime-processed gelatin having a calcium concentration of 1 ppm was added. After the completion of addition, 250 mL of an aqueous solution containing 70 g of silver nitrate and an aqueous KBr solution were added over 20 minutes while keeping the potential at 60 mV. At this time, yellow prussiate of potash was added in an amount of $1.0 \times 10^{-5}$ mol per mol of silver. The obtained emulsion was washed with water and after adding 80 g of lime-processed gelatin having a calcium concentration of 1 ppm, the pH and the pAg were adjusted at 40° C. to 5.8 and 8.7, respectively.

The calcium, magnesium and strontium contents of the thus-obtained emulsion were measured by the ICP emission spectrometry and found to be 15 ppm, 2 ppm and 1 ppm, respectively.

The chemical sensitization was performed in the same manner as in Em-C except that Sensitizing Dyes 1, 2 and 3 were replaced by Sensitizing Dyes 4, 5 and 6 and the amounts added were changed to $1.00 \times 10^{-3}$ mol. $2.15 \times 10^{-4}$ mol and $8.06 \times 10^{-5}$ mol, respectively, and thereby Em-G was prepared.

Preparation of Em-J

Em-J was prepared in the same manner as Em-B except that in the preparation of Em-B, the sensitizing dyes added before the chemical sensitization were changed to Sensitizing Dyes 7 and 8 and the amounts added were $7.65 \times 10^{-4}$ mol and $2.74 \times 10^{-4}$ mol, respectively.

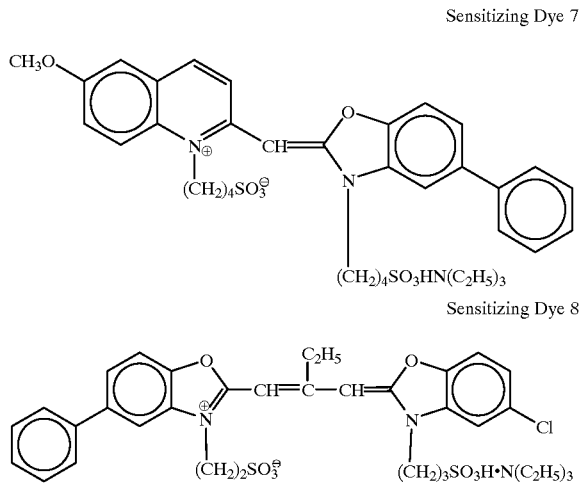

Sensitizing Dye 7

Sensitizing Dye 8

Preparation of Em-L
Preparation of Silver Bromide Seed Crystal Emulsion

A silver bromide tabular emulsion having an average equivalent-sphere diameter of 0.6 μm and an aspect ratio of 9.0 and containing 1.16 mol of silver and 66 g of gelatin, per 1 kg of the emulsion was prepared.

Growth Process 1

To 1,250 g of an aqueous solution containing 1.2 g of potassium bromide and succinated gelatin having a succination percentage of 98%, 0.3 g of modified silicon oil was added. To the resulting solution, the silver bromide tabular emulsion prepared above was added in an amount corresponding to 0.086 mol of silver and the mixture was stirred while keeping at 78° C. Thereto, an aqueous solution containing 18.1 g of silver nitrate was added and silver iodide fine grains having an equivalent-sphere diameter of 0.037 μm was added to have a coverage of 5.4 mol based on silver to which the grain was added. At this time, an aqueous potassium bromide solution was added by a double jet method while controlling the addition to adjust the pAg to 8.1.

Growth Process 2

After adding 2 mg of sodium benzenethiosulfonate, 0.45 g of disodium 3,5-disulfocatechol and 2.5 mg of thiourea dioxide were added.

Furthermore, an aqueous solution containing 95.7 g of silver nitrate and an aqueous potassium bromide solution were added by a double jet method while accelerating the flow rate. At this time, silver iodide fine grains having an equivalent-sphere diameter of 0.037 μm were added to have a coverage of 7.0 mol based on silver to which the grain was added. Also, the amount of potassium bromide added above by the double jet method was controlled to adjust the pAg to 8.1. After the completion of addition, 2 mg of sodium benzenethiosulfonate was added.

Growth Process 3

An aqueous solution containing 19.5 g of silver nitrate and an aqueous potassium bromide solution were added by a double jet method over 16 minutes. At this time, the amount of the aqueous potassium bromide solution was controlled to adjust the pAg to 7.9.

Addition 4 of Sparingly Soluble Silver Halide Emulsion

After adjusting the host grains to 9.3 with an aqueous potassium bromide solution, 25 g of the above-described silver iodide fine grain emulsion having an equivalent-sphere diameter of 0.037 μm was rapidly added within 20 seconds.

Formation 5 of Outermost Shell Layer

An aqueous solution containing 34.9 g of silver nitrate was added over 22 minutes.

This emulsion was tabular grains having an average aspect ratio of 9.8, an average equivalent-sphere diameter of 1.4 μm and an average silver iodide content of 5.5 mol %.

Chemical Sensitization

After water washing, succinated gelatin having a succination percentage of 98% and calcium nitrate were added to adjust at 40° C. the pH and the pAg to 5.8 and 8.7, respectively. The temperature was elevated to 60° C., a silver bromide fine grain emulsion of 0.07 μm was added in an amount of $5 \times 10^{-3}$ mol and after 20 minutes, Sensitizing Dyes 9, 10 and 11 were added. Thereafter, potassium thiocyanate, chloroauric acid, sodium thiosulfate, N,N-dimethylselenourea and Compound 4 were added to optimally perform the chemical sensitization. Compound 3 was added 20 minutes before the completion of chemical sensitization and. Compound 5 was added at the completion of chemical sensitization. The term "optimally perform the chemical sensitization" as used herein means that the amounts of sensitizing dyes and respective compounds added were selected from the range from $10^{-1}$ to $10^{-8}$ mol per mol of silver halide so that highest sensitivity could be attained at the exposure for 1/100 second.

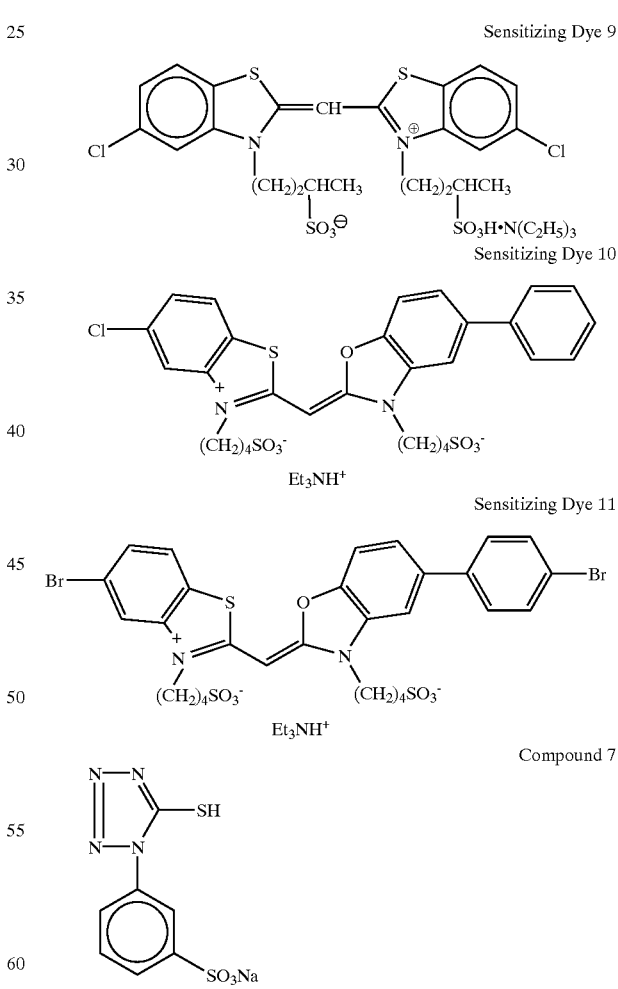

Sensitizing Dye 9

Sensitizing Dye 10

Sensitizing Dye 11

Compound 7

Preparation of Em-O

In a reactor equipped with a stirrer, an aqueous gelatin solution (distilled water: 1,250 mL, deionized gelatin: 48 g, KBr: 0.75 g) was charged and the solution temperature was kept at 70° C. To this solution, 276 mL of an aqueous silver nitrate solution (containing 12.0 g of silver nitrate) and an aqueous KBr solution in an equimolar concentration were added by a double jet method over 7 minutes while keeping the pAg at 7.26. Then, the temperature was lowered to 68° C. and 7.6 mL of 0.05 mass % thiourea dioxide was added.

Subsequently, 592.9 mL of an aqueous silver nitrate solution (containing 108.0 g of silver nitrate) and a mixed aqueous solution of KBr and KI in equimolar concentrations (KI: 2.0 mol %) were added by a controlled double jet method over 18 minutes and 30 seconds while keeping the pAg at 7.30.5 Minutes before the completion of addition, 18.0 mL of 0.1 mass % thiosulfonic acid was added.

The obtained grains were cubic grains having an equivalent-sphere diameter of 0.19 $\mu$m and an average silver iodide content of 1.8 mol %.

Em-O was re-dispersed through desalting and water washing by a normal flocculation method and then adjusted to a pH of 6.2 and a pAg of 7.6 at 40° C.

Thereafter, Em-O was subjected to spectral sensitization and chemical sensitization as follows. First, Sensitizing Dyes 10, 11 and 12 each in an amount of $3.37 \times 10^{-4}$ mol/mol-Ag, KBr in $8.82 \times 10^{-4}$ mol/Mol-Ag, sodium thiosulfate in $8.83 \times 10^{-5}$ mol/mol-Ag, potassium thiocyanate in $5.95 \times 10^{-4}$ mol/mol-Ag and potassium chloroaurate in $3.07 \times 10^{-5}$ mol/mol-Ag were added to perform the ripening at 68° C. The ripening time was adjusted to give highest sensitivity at the exposure for 1/100 second.

Sensitizing Dye 12

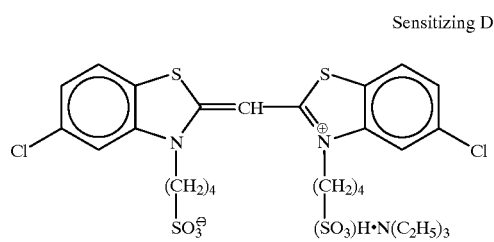

Em-D, H, I, K, M and N

For the preparation of tabular grains, a low molecular weight gelatin was used according to the Example of JP-A-1-158426. Furthermore, according to the Example of JP-A-3-237450, the emulsions were subjected to gold sensitization, sulfur sensitization and selenium sensitization in the presence of spectral sensitizing dyes shown in Table 2 and sodium thiocyanate. Emulsions D, H, I and K contained Ir and Fe each in an optimal amount. Emulsions M and N were subjected to reduction sensitization using thiourea dioxide and thiosulfonic acid at the preparation of grains according to the Example of JP-A-2-191938.

TABLE 4

| Emulsion | Sensitizing Dye | Amount Added (mol/mol-Ag) |
|---|---|---|
| Em-D | Sensitizing Dye 1 | $5.44 \times 10^{-4}$ |
|  | Sensitizing Dye 2 | $2.35 \times 10^{-4}$ |
|  | Sensitizing Dye 3 | $7.26 \times 10^{-6}$ |
| Em-H | Sensitizing Dye 8 | $6.52 \times 10^{-4}$ |
|  | Sensitizing Dye 13 | $1.35 \times 10^{-4}$ |
|  | Sensitizing Dye 6 | $2.48 \times 10^{-5}$ |
| Em-I | Sensitizing Dye 8 | $6.09 \times 10^{-4}$ |
|  | Sensitizing Dye 13 | $1.26 \times 10^{-4}$ |
|  | Sensitizing Dye 6 | $2.32 \times 10^{-5}$ |
| Em-K | Sensitizing Dye 7 | $6.27 \times 10^{-4}$ |
|  | Sensitizing Dye 8 | $2.24 \times 10^{-4}$ |

TABLE 4-continued

| Emulsion | Sensitizing Dye | Amount Added (mol/mol-Ag) |
|---|---|---|
| Em-M | Sensitizing Dye 9 | $2.43 \times 10^{-4}$ |
|  | Sensitizing Dye 10 | $2.43 \times 10^{-4}$ |
|  | Sensitizing Dye 11 | $2.43 \times 10^{-4}$ |
| Em-N | Sensitizing Dye 9 | $3.28 \times 10^{-4}$ |
|  | Sensitizing Dye 10 | $3.28 \times 10^{-4}$ |
|  | Sensitizing Dye 11 | $3.28 \times 10^{-4}$ |

Sensitizing Dye 13

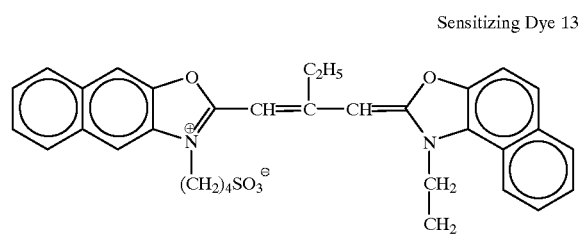

TABLE 5

| Name of Emulsion | Average Iodide (mol %) | Equivalent-Sphere Diameter ($\mu$m) | Aspect Ratio | Equivalent-Circle Diameter ($\mu$m) | Grain Thickness ($\mu$m) | Shape |
|---|---|---|---|---|---|---|
| Em-A | 4 | 0.92 | 14 | 2 | 0.14 | tabular |
| Em-B | 5 | 0.8 | 12 | 1.6 | 0.13 | tabular |
| Em-C | 4.7 | 0.51 | 7 | 0.85 | 0.12 | tabular |
| EM-D | 3.9 | 0.37 | 2.7 | 0.4 | 0.15 | tabular |
| Em-E | 5 | 0.92 | 14 | 2 | 0.14 | tabular |
| Em-F | 5.5 | 0.8 | 12 | 1.6 | 0.13 | tabular |
| Em-G | 4.7 | 0.51 | 7 | 0.85 | 0.12 | tabular |
| Em-H | 3.7 | 0.49 | 3.2 | 0.58 | 0.18 | tabular |
| Em-I | 2.8 | 0.29 | 1.2 | 0.27 | 0.23 | tabular |
| Em-J | 5 | 0.8 | 12 | 1.6 | 0.13 | tabular |
| Em-K | 3.7 | 0.47 | 3 | 0.53 | 0.18 | tabular |
| Em-L | 5.5 | 1.4 | 9.8 | 2.6 | 0.27 | tabular |
| Em-M | 8.8 | 0.64 | 5.2 | 0.85 | 0.16 | tabular |
| Em-N | 3.7 | 0.37 | 4.6 | 0.55 | 0.12 | tabular |
| Em-O | 1.8 | 0.19 | — | — | — | cubic |

In Table 5, when the tabular grains are viewed through a high-pressure electron microscope, dislocation lines as described in JP-A-3-237450 are observed.

2) Support

The support used in this Example was manufactured by the following method.

2-1 First Layer and Undercoat Layer

Both surfaces of a 90 $\mu$m-thick polyethylene naphthalate support were subjected to a glow discharge treatment at a treating atmosphere pressure of $2.66 \times 10$ Pa, a water vapor partial pressure of 75% in the atmosphere gas, a discharge frequency of 30 kHz, an output of 2,500 W and a treating strength of 0.5 kV·A·min/m$^2$. On this support, a coating solution for the first layer having the following composition was coated to a coated amount of 5 mL/m$^2$ using a bar coating method described in JP-B-58-4589 (the term "JP-B" as used herein means an "examined Japanese patent publication").

| | |
|---|---|
| Dispersion solution of electrically conducting fine particles (a water dispersion having an SnO$_2$/Sb$_2$O$_5$ particle concentration of 10%; secondary aggregate of primary particles having a particle diameter of 0.005 μm; the average particle diameter: 0.05 μm) | 50 parts by mass |
| Gelatin | 0.5 parts by mass |
| Water | 49 parts by mass |
| Polyglycerol polyglycidyl ether | 0.16 parts by mass |
| Poly(polymerization degree: 20)-oxyethylene sorbitan monolaurate | 0.1 parts by mass |

After providing the first layer, the support was wound around a 20 cm-diameter stainless steel core and subjected to annealing of performing a heat treatment at 110° C. (Tg of PEN support: 119° C.) for 48 hours to have a heat history. Thereafter, a coating solution having the following composition was coated to a coated amount of 10 mL/m$^2$ to form an undercoat layer for emulsion in the side opposite the first layer with an intervention of the support.

| | |
|---|---|
| Gelatin | 1.01 parts by mass |
| Salicylic acid | 0.30 parts by mass |
| Resorcin | 0.40 parts by mass |
| Poly(polymerization degree: 10)-oxyethylene nonylphenyl ether | 0.11 parts by mass |
| Water | 3.53 parts by mass |
| Methanol | 84.57 parts by mass |
| n-Propanol | 10.08 parts by mass |

Furthermore, a second layer and a third layer, which are described later, were provided in this order on the first layer and finally, a color negative light-sensitive material having a composition shown below was coated to complete multiple layers, whereby a transparent magnetic recording medium with a silver halide emulsion layer was manufactured.

2-2) Second Layer (Transparent Magnetic Recording Layer)

(i) Dispersion of Magnetic Substance 1,100 parts by mass of a Co-doped γ-Fe$_2$O$_3$ magnetic substance (average long axis length: 0.25 μm, S$_{BET}$: 39 m$^2$/g, Hc: 6.56×10$^4$ A/m, σs: 77.1 Am$^2$/kg, σr: 37.4 Am$^2$/kg), 220 parts by mass of water and 165 parts by mass of a silane coupling agent [3-(poly(polymerization degree: 10)oxyethynyl)oxypropyl trimethoxysilane were added and thoroughly kneaded in an open kneader for 3 hours. The resulting crudely dispersed viscous solution was dried at 70° C. over day and night to remove water and then heat-treated at 110° C. for 1 hour to prepare surface-treated magnetic particles.

The thus-obtained magnetic particles were again kneaded in an open kneader for 4 hours according to the following formulation.

| | |
|---|---|
| Surface-treated magnetic particles prepared above | 855 g |
| Diacetyl cellulose | 25.3 g |
| Methyl ethyl ketone | 136.3 g |
| Cyclohexanone | 136.3 g |

The kneaded product was finely dispersed by a sand mill (sand mill of ¼ G) at 2,000 rpm for 4 hours according to the following formulation. The dispersion medium used was 1 mmφ (1 mm diameter) glass beads.

| | |
|---|---|
| Kneaded solution prepared above | 45 g |
| Diacetyl cellulose | 23.7 g |
| Methyl ethyl ketone | 127.7 g |
| Cyclohexanone | 127.7 g |

Furthermore, a magnetic substance-containing intermediate solution was prepared according to the following formulation.

(ii) Preparation of Magnetic Substance-Containing Intermediate Solution

| | |
|---|---|
| Magnetic substance finely dispersed solution prepared above | 674 g |
| Diacetyl cellulose solution (solid content: 4.34%, solvent: methyl ethyl ketone/cyclohexanone (1/1)) | 24,280 g |
| Cyclohexanone | 46 g |

These were mixed and then stirred by Disper to prepare a "magnetic substance-containing intermediate solution".

(iii) Preparation of Dispersion Solution of Sumicolandum AA-1.5 (average primary particle diameter: 1.5 μm, specific surface area: 1.3 m$^2$/g)

An α-alumina abrasive dispersion solution of the present invention was prepared according to the following formulation.

| | |
|---|---|
| Sumicolandum AA-1.5 | 152 g |
| Silane coupling agent KBM903 (produced by Shin-Etsu Silicone) | 0.48 g |
| Diacetyl cellulose solution (solid content: 4.5%, solvent: methyl ethyl ketone/cyclohexanone (1/1)) | 227.52 g |

These were finely dispersed at 800 rpm for 4 hours using a ceramic-coated sand mill (sand mill of ¼ G). The dispersion medium used was 1 mmφ zirconia beads.

(iv) Preparation of Dispersion Solution of Colloidal Silica Particles (fine particles)

"MEK-ST" produced by Nissan Chemical was used.

This is a dispersion solution of colloidal silica having an average primary particle diameter of 0.015 μm using methyl ethyl ketone as the dispersion medium and the solid content thereof is 30%.

(v) Preparation of Coating Solution for Second Layer

| | |
|---|---|
| Magnetic substance-containing intermediate solution prepared above | 19,053 g |
| Diacetyl cellulose solution (solid content: 4.5%, solvent: methyl ethyl ketone/cyclohexanone (1/1)) | 264 g |
| Colloidal silica dispersion solution "MEK-ST" [Dispersion Solution b] (solid content: 30%) | 128 g |
| AA-1.5 dispersion solution [Dispersion Solution a] | 12 g |
| Millionate MR-400 (produced by Nippon Polyurethane) diluted solution (solid content: 20%, diluting solvent: methyl ethyl ketone/cyclohexanone (1/1)) | 203 g |
| Methyl ethyl ketone | 170 g |
| Cyclohexanone | 170 g |

These were mixed and stirred and the obtained coating solution was coated by a wire bar to a coated amount of 29.3 mL/m². The drying was performed at 110° C. The thickness of the formed magnetic layer after the drying was 1.0 μm.

2-3) Third Layer (Higher Fatty Acid Ester Slipping Agent-Containing Layer)

(i) Preparation of Dispersion Stock Solution of Slipping Agent

The following solution (a) was dissolved under heating at 100° C. and after adding thereto the solution (b), dispersed in a high-pressure homogenizer to prepare a dispersion stock solution of slipping agent.

| Solution (a): | |
|---|---|
| Compound shown below $C_6H_{13}CH(OH)(CH_2)_{10}COOC_{50}H_{101}$ | 399 parts by mass |
| Compound shown below n-$C_{50}H_{101}O(CH_2CH_2O)_{16}H$ | 171 parts by mass |
| Solution (b): | |
| Cyclohexanone | 8,600 parts by mass |

(ii) Preparation of Dispersion Solution of Spherical Inorganic Particles

Dispersion Solution [c1] of spherical inorganic particles was prepared according to the following formulation:

| | |
|---|---|
| Isopropyl alcohol | 93.54 parts by mass |
| Silane coupling agent KBM903 (produced by Shin-Etsu Silicone) | |
| Compound 1-1: $(CH_3O)_3Si$-$(CH_2)_3$-$NH_2$ | 5.53 parts by mass |
| Compound 8 | 2.93 parts by mass |

$$(n)C_4H_9-\overset{C_2H_5}{\underset{|}{CH}}-CH_2O\overset{O}{\underset{||}{C}}-\overset{|}{\underset{|}{CH}}-SO_3Na$$
$$(n)C_4H_9-\overset{|}{\underset{C_2H_5}{CH}}-CH_2O\overset{|}{\underset{||}{C}}-CH_2$$
$$\phantom{(n)C_4H_9-CH-CH_2OC-}O$$

SEAHOSTA KEP50 (amorphous spherical silica, average particle diameter: 0.5 μm, produced by Nippon Shokubai K.K.) 88.00 parts by mass These were stirred for 10 minutes while ice-cooling and stirring and the following was added thereto.

| | |
|---|---|
| Diacetone alcohol | 252.93 parts by mass |

The obtained solution was dispersed for 3 hours using an ultrasonic homogenizer "SONIFIER 450, manufactured by BRANSON) to complete Dispersion Solution c1 of spherical inorganic particles.

(iii) Preparation of Dispersion Solution of Spherical Organic Polymer Particles

Dispersion Solution [c2] of spherical organic polymer particles was prepared according to the following formulation:

| | |
|---|---|
| XC99-A8808 (produced by Toshiba Silicone, spherical crosslinked polysiloxane particles, average particle size: 0.9 μm) | 60 parts by mass |
| Methyl ethyl ketone | 120 parts by mass |
| Cyclohexanone (solid content: 20%, solvent: methyl ethyl ketone/cyclohexanone (1/1)) | 120 parts by mass |

These were dispersed for 2 hours using an ultrasonic homogenizer "SONIFIER 450, manufactured by BRANSON) while ice-cooling and stirring to complete Dispersion Solution c2 of spherical organic polymer particles.

(iv) Preparation of Coating Solution for Third Layer

To 542 g of the dispersion stock solution of slipping agent prepared above, the followings were added to prepare a coating solution for the third layer.

| | |
|---|---|
| Diacetone alcohol | 5,950 g |
| Cyclohexanone | 176 g |
| Ethyl acetate | 1,700 g |
| Dispersion Solution [c1] of SEAHOSTA KEP50 prepared above | 53.1 g |
| Dispersion Solution [c2] of spherical organic polymer particles prepared above | 300 g |
| FC431 (produced by 3M, solid content: 50%, solvent: ethyl acetate) | 2.65 g |
| BYK310 (produced by BYK Chemi-Japan, solid content: 25%) | 5.3 g |

The obtained coating solution was coated on the second layer to a coated amount of 10.35 mL/m², dried at 110° C. and further dried at 97° C. for 3 minutes.

3) Coating of Light-Sensitive Layers

On the surface opposite the back layer provided above, the layers each having the following composition were coated one on another to manufacture a color negative film Compositions of Light-Sensitive Materials Main materials used for each layer are classified as follows.

ExC: cyan coupler

ExM: magenta coupler

ExY: yellow coupler

UV: ultraviolet absorbent

HBS: high boiling point organic solvent

H: gelatin hardener (In the following, the specific compound is shown by a symbol with a numerical value and the chemical formula is shown later).

The numerals corresponding to respective components are a coated amount expressed by the unit of g/m². With respect to silver halide, the coated amount is calculated in terms of silver.

| First Layer (First Antihalation Layer) | |
|---|---|
| Black colloidal silver | as silver 0.122 |
| Silver iodobromide emulsion of 0.07 μm | as silver 0.01 |
| Gelatin | 0.919 |
| ExM-1 | 0.066 |
| ExC-1 | 0.002 |

| | |
|---|---|
| ExC-3 | 0.002 |
| Cpd-2 | 0.001 |
| F-8 | 0.010 |
| HBS-1 | 0.005 |
| HBS-2 | 0.002 |
| Second Layer (Second Antihalation Layer) | |
| Black colloidal silver | as silver 0.055 |
| Gelatin | 0.425 |
| ExF-1 | 0.002 |
| F-8 | 0.012 |
| Solid Disperse Dye ExF-7 | 0.120 |
| HBS-1 | 0.074 |
| Third Layer (Interlayer) | |
| ExC-2 | 0.050 |
| Cpd-1 | 0.090 |
| Polyethyl acrylate latex | 0.200 |
| HBS-1 | 0.100 |
| Gelatin | 0.700 |
| Fourth Layer (Low-Sensitivity Red-Sensitive Emulsion Layer) | |
| Em-D | as silver 0.577 |
| Em-C | as silver 0.347 |
| ExC-1 | 0.188 |
| ExC-2 | 0.011 |
| ExC-3 | 0.075 |
| ExC-4 | 0.121 |
| ExC-5 | 0.010 |
| ExC-6 | 0.007 |
| ExC-8 | 0.050 |
| ExC-9 | 0.020 |
| Cpd-2 | 0.025 |
| Cpd-4 | 0.025 |
| HBS-1 | 0.114 |
| HBS-5 | 0.038 |
| Gelatin | 1.474 |
| (Medium-Sensitivity Red-Sensitive Emulsion Layer) | |
| Em-B | as silver 0.431 |
| Em-C | as silver 0.432 |
| ExC-1 | 0.154 |
| ExC-2 | 0.068 |
| ExC-3 | 0.018 |
| ExC-4 | 0.103 |
| ExC-5 | 0.023 |
| ExC-6 | 0.010 |
| ExC-8 | 0.016 |
| ExC-9 | 0.005 |
| Cpd-2 | 0.036 |
| Cpd-4 | 0.028 |
| HBS-1 | 0.129 |
| Gelatin | 1.086 |
| Sixth Layer (High-Sensitivity Red-Sensitive Emulsion Layer) | |
| Em-A | as silver 1.108 |
| ExC-1 | 0.180 |
| ExC-3 | 0.035 |
| ExC-6 | 0.029 |
| ExC-8 | 0.110 |
| ExC-9 | 0.020 |
| Cpd-2 | 0.064 |
| Cpd-4 | 0.077 |
| HBS-1 | 0.329 |
| HBS-2 | 0.120 |
| Gelatin | 1.245 |
| Seventh Layer (Interlayer) | |
| Cpd-1 | 0.089 |
| Cpd-6 | 0.369 |
| Solid Disperse Dye ExF-4 | 0.030 |
| HBS-1 | 0.049 |
| Polyethyl acrylate latex | 0.088 |
| Gelatin | 0.886 |
| Eighth Layer (Layer for Imparting Interimage Effect to Red-Sensitive Layer) | |
| Em-J | as silver 0.293 |
| Em-K | as silver 0.293 |
| Cpd-4 | 0.030 |
| ExM-2 | 0.120 |
| ExH-3 | 0.016 |
| ExM-4 | 0.026 |
| ExY-1 | 0.016 |
| ExY-4 | 0.036 |
| ExC-7 | 0.026 |
| HBS-1 | 0.090 |
| HBS-3 | 0.003 |
| HBS-5 | 0.030 |
| Gelatin | 0.610 |
| Ninth Layer (Low-Sensitivity Green-Sensitive Emulsion Layer) | |
| Em-H | as silver 0.329 |
| Em-G | as silver 0.333 |
| Em-I | as silver 0.088 |
| ExM-2 | 0.378 |
| ExM-3 | 0.047 |
| ExY-1 | 0.017 |
| ExC-7 | 0.007 |
| HBS-1 | 0.098 |
| HBS-3 | 0.010 |
| HBS-4 | 0.077 |
| HBS-5 | 0.548 |
| Cpd-5 | 0.010 |
| Gelatin | 1.470 |
| Tenth Layer (Medium-Sensitivity Green-Sensitive Emulsion Layer) | |
| Em-F | as silver 0.457 |
| ExM-2 | 0.032 |
| ExM-3 | 0.029 |
| ExM-4 | 0.029 |
| ExY-3 | 0.007 |
| ExC-6 | 0.010 |
| ExC-7 | 0.012 |
| ExC-8 | 0.010 |
| HBS-1 | 0.065 |
| HBS-3 | 0.002 |
| HBS-5 | 0.020 |
| Cpd-5 | 0.004 |
| Gelatin | 0.446 |
| Eleventh Layer (High-Sensitivity Green-Sensitive Emulsion Layer) | |
| Em-E | as silver 0.794 |
| ExC-6 | 0.002 |
| ExC-8 | 0.010 |
| ExM-1 | 0.013 |
| ExM-2 | 0.011 |
| ExM-3 | 0.030 |
| ExM-4 | 0.017 |
| ExY-3 | 0.003 |
| Cpd-3 | 0.004 |
| Cpd-4 | 0.007 |
| Cpd-5 | 0.010 |
| HBS-1 | 0.148 |
| HBS-5 | 0.037 |
| Polyethyl acrylate latex | 0.099 |
| Gelatin | 0.939 |
| Twelfth Layer (Yellow Filter Layer) | |
| Cpd-1 | 0.094 |
| Solid Disperse Dye ExF-2 | 0.150 |
| Solid Disperse Dye ExF-5 | 0.010 |
| Oil-Soluble Dye ExF-6 | 0.010 |
| HBS-1 | 0.049 |
| Gelatin | 0.630 |
| Thirteenth Layer (Low-Sensitivity Blue-Sensitive Emulsion Layer) | |
| Em-O | as silver 0.112 |
| Em-M | as silver 0.320 |
| Em-N | as silver 0.240 |
| ExC-1 | 0.027 |
| ExC-7 | 0.013 |
| ExY-1 | 0.002 |
| ExY-2 | 0.890 |
| ExY-4 | 0.058 |

|  |  |
| --- | --- |
| -continued | |
| Cpd-2 | 0.100 |
| Cpd-3 | 0.004 |
| HBS-1 | 0.222 |
| HBS-5 | 0.074 |
| Gelatin | 2.058 |
| Fourteenth Layer (High-Sensitivity Blue-Sensitive Emulsion Layer) | |
| Em-L | as silver 0.714 |
| ExY-2 | 0.211 |
| ExY-4 | 0.068 |
| Cpd-2 | 0.075 |
| Cpd-3 | 0.001 |
| HBS-1 | 0.71 |
| Gelatin | 0.678 |
| Fifteenth Layer (First Protective Layer) | |
| Silver iodobromide emulsion of 0.07 μm | as silver 0.301 |
| UV-1 | 0.211 |
| UV-2 | 0.132 |
| UV-3 | 0.198 |
| UV-4 | 0.026 |
| F-18 | 0.009 |
| S-1 | 0.086 |
| HBS-1 | 0.175 |
| HBS-4 | 0.050 |
| Gelatin | 1.984 |
| Sixteenth Layer (Second Protective Layer) | |
| H-1 | 0.400 |
| B-1 (Diameter: 1.7 μm) | 0.050 |
| B-2 (Diameter: 1.7 μm) | 0.150 |
| B-3 | 0.050 |
| S-1 | 0.200 |
| Gelatin | 0.750 |

Furthermore, in order to improve storability, processability, pressure resistance, antifungal/antibacterial property, antistatic property and coatability, W-1 to W-6, B-4 to B-6, F-1 to F-17, lead salt, platinum salt, iridium salt and rhodium salt were appropriately added to each layer.

Preparation of Dispersion of Organic Solid Disperse Dye

ExF-2 of the twelfth layer was dispersed by the following method.

| | |
| --- | --- |
| Wet cake of ExF-2 (containing 17.6 wt % of water) | 2.800 kg |
| Sodium octylphenyldiethoxy-methanesulfonate (31 wt % aqueous solution) | 0.376 kg |
| F-15 (5% aqueous solution) | 0.011 kg |
| Water | 4.020 kg |
| Total | 7.210 kg |

(pH was adjusted to 7.2 with NaOH)

The slurry having the above-described composition was crudely dispersed by stirring with a dissolver and then dispersed using an agitator mill LMK-4 at a peripheral speed of 10 m/s, an ejection amount of 0.6 kg/min and a 0.3-mmφ zirconia bead-filling percentage of 80% until the absorbancy ratio became 0.29, thereby obtaining a solid fine particle dispersion. The obtained dye fine particles had an average particle diameter of 0.29 μm.

Solid dispersions of ExF-4 and ExF-7 were obtained in the same tanner. The dye fine particles had an average particle size of 0.28 μm and 0.49 μm, respectively. ExF-5 was dispersed by the microprecipitation dispersing method described in Example 1 of EF-A-549489. The average particle diameter was 0.06 μm.

The compounds used in each layer are shown below.

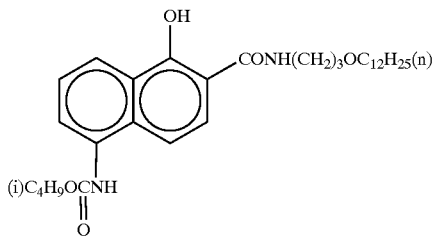

ExC-1

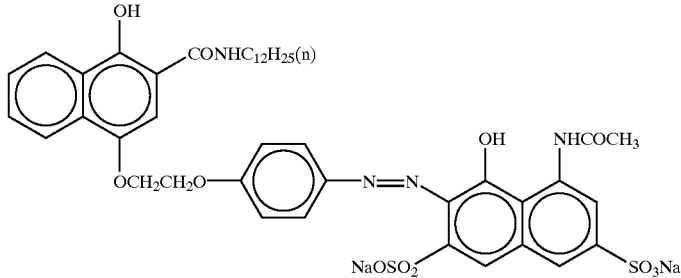

ExC-2

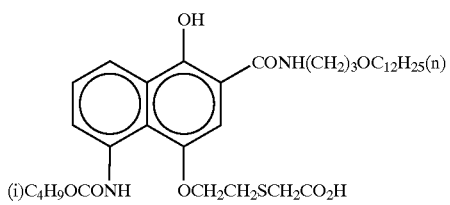

ExC-3

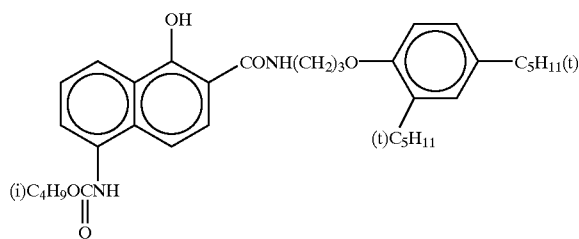

ExC-4

-continued
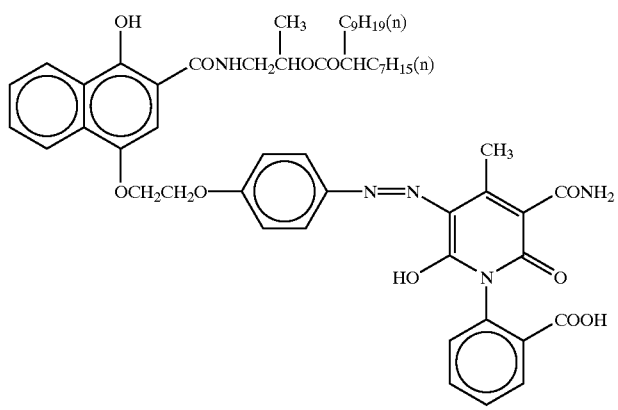
ExC-5
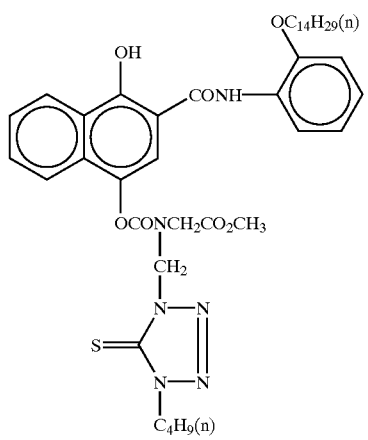
ExC-6
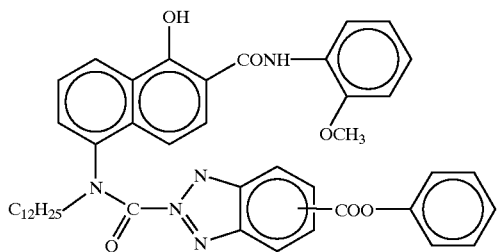
ExC-7
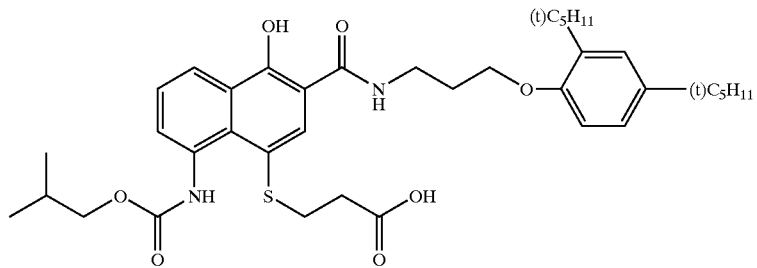
ExC-8
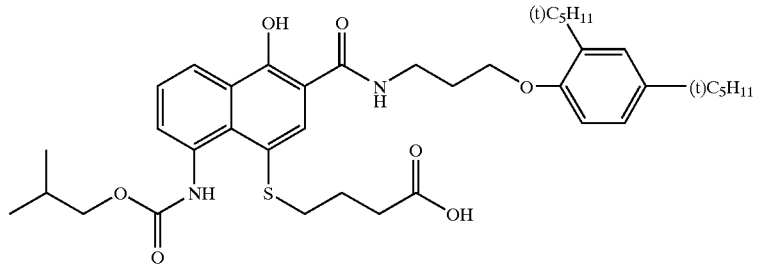
ExC-9

ExM-1
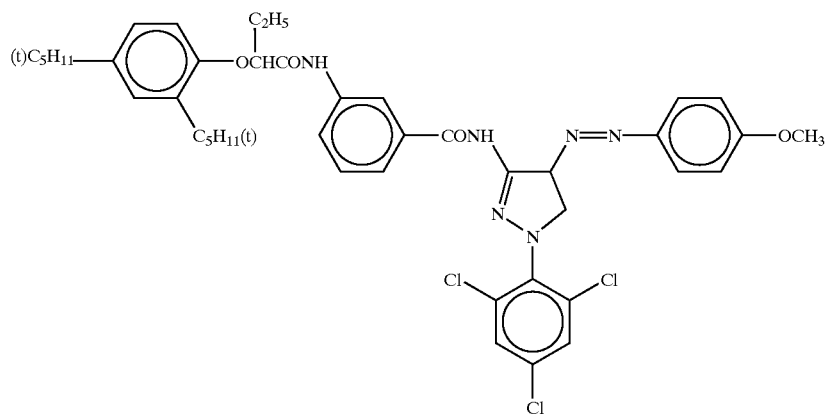
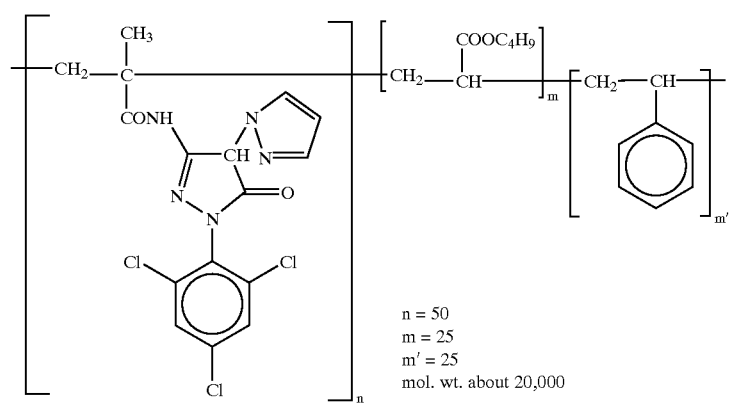
n = 50
m = 25
m' = 25
mol. wt. about 20,000
ExM-3
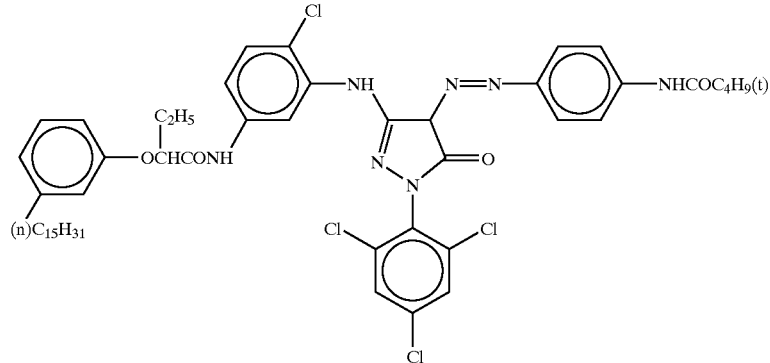
ExM-4
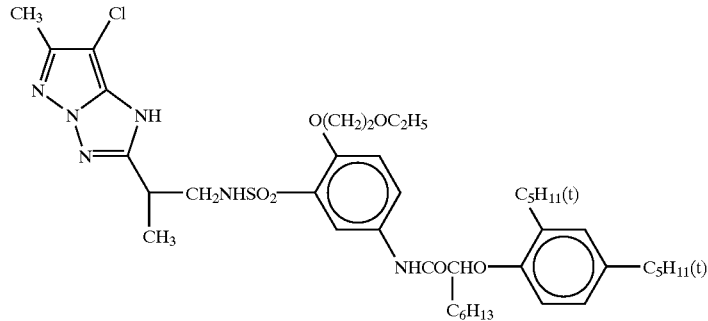

-continued
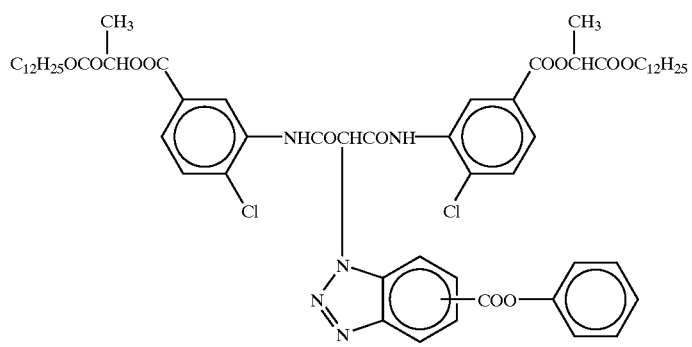
ExY-1
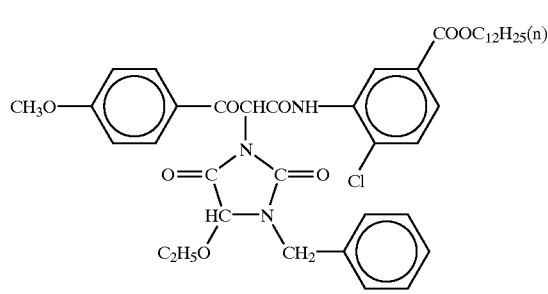
ExY-2
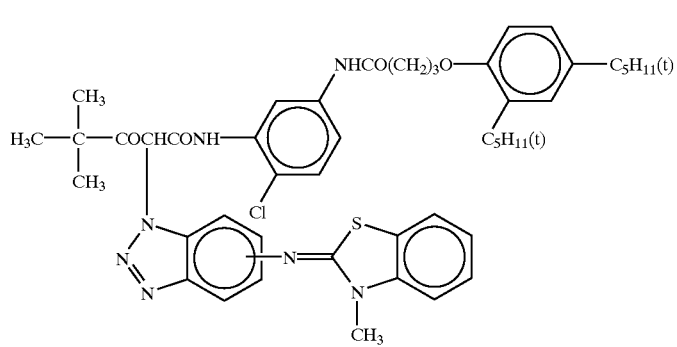
ExY-3
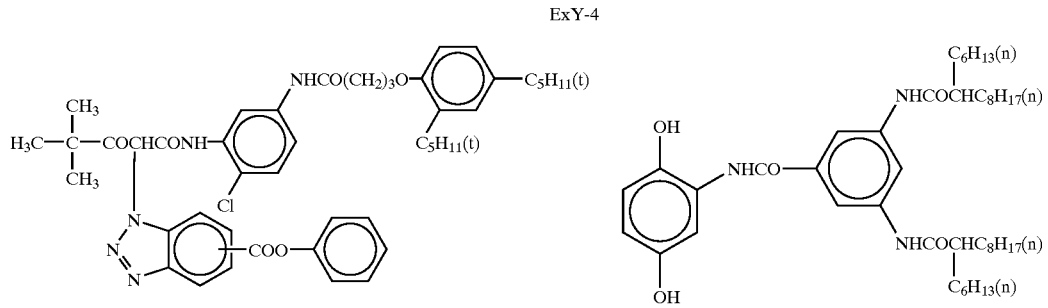
ExY-4
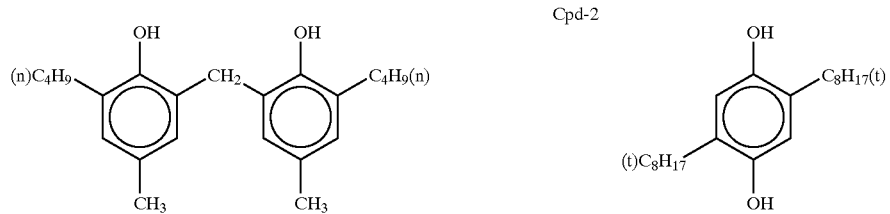
Cpd-1
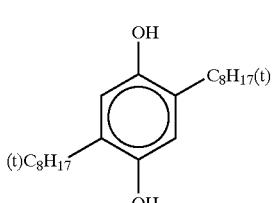
Cpd-2
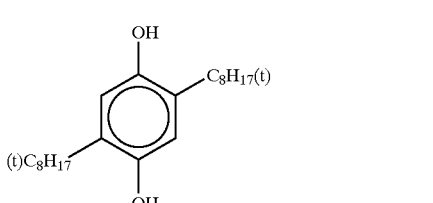
Cpd-3

-continued
Cpd-4
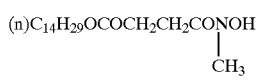
Cpd-5
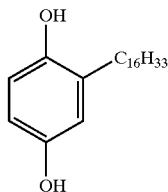
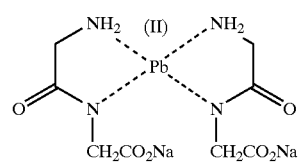
Cpd-6
UV-1
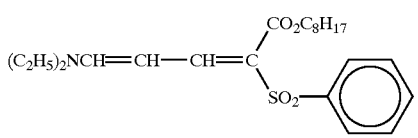
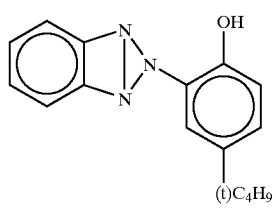
UV-2
UV-3
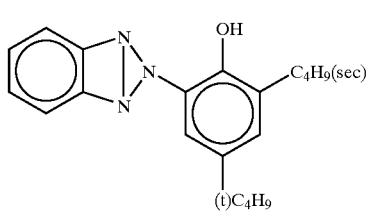
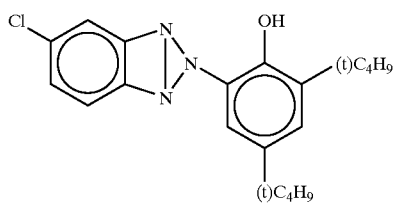
UV-4
B-1
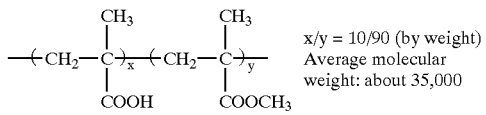
x/y = 10/90 (by weight)
Average molecular weight: about 35,000
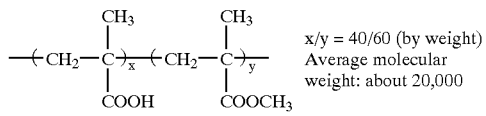
x/y = 40/60 (by weight)
Average molecular weight: about 20,000
B-2 
B-3
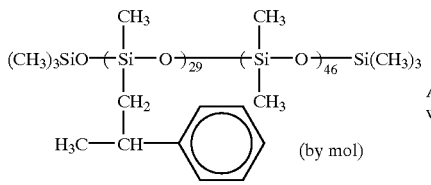 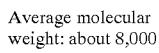
Average molecular weight: about 8,000
(by mol)
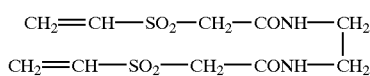
H-1 
Tricresyl phosphate 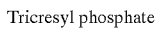
HBS-1 
Di-n-butyl phthalate
HBS-2 
HBS-3 
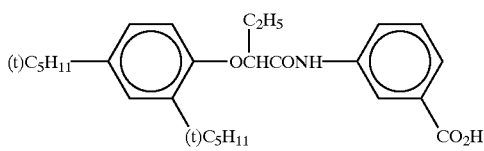
Tri (2-ethylhexyl) phosphate
HBS-4 
HBS-5
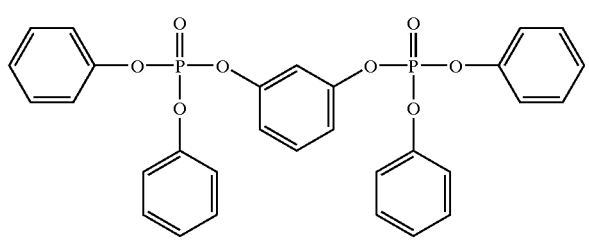

-continued
S-1 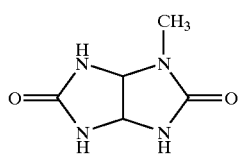
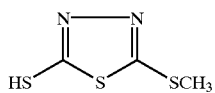
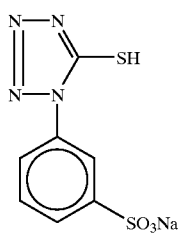
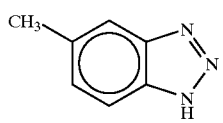
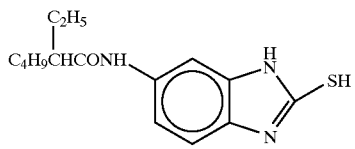
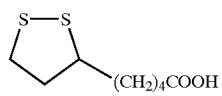
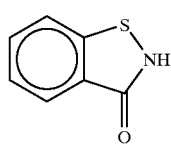
F-18 
F-1 F-2 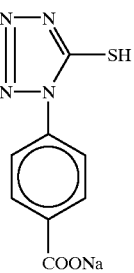
F-3 F-4 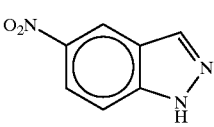
F-5 F-6 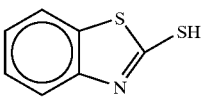
F-7 F-8 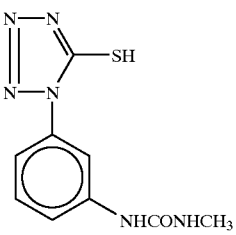
F-9 F-10 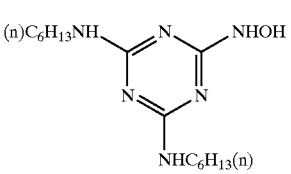
F-11 F-12 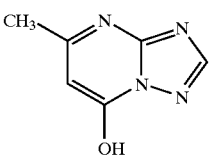
F-13 F-14 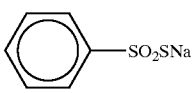
F-15 F-16 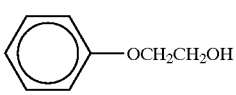

-continued
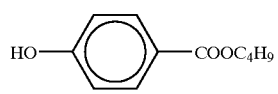
F-17
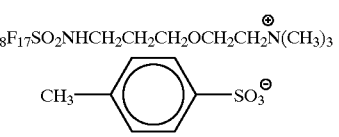
W-1
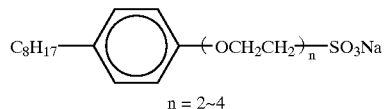
n = 2~4
W-2
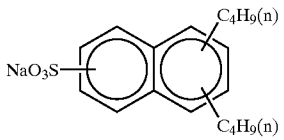
W-3
W-4
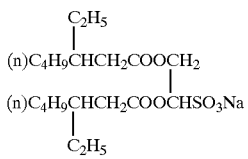
W-5
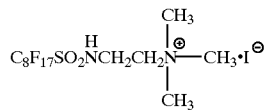
W-6
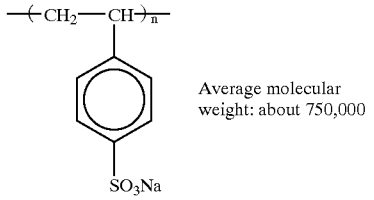
Average molecular weight: about 750,000
B-4
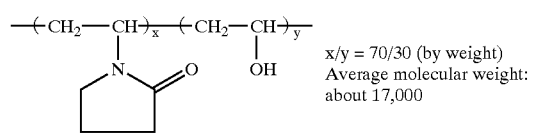
x/y = 70/30 (by weight)
Average molecular weight: about 17,000
B-5
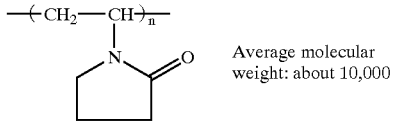
Average molecular weight: about 10,000
B-6
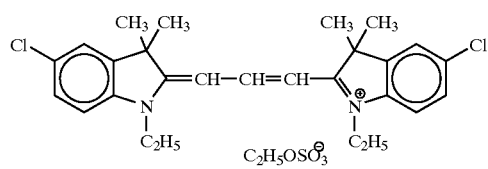
ExF-1
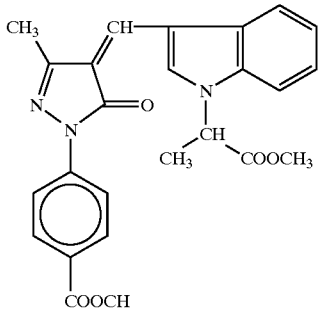
ExF-2
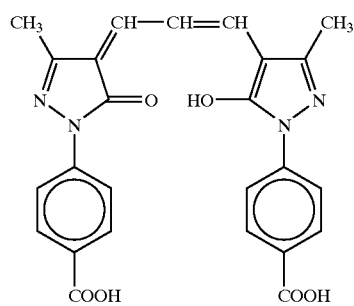
ExF-4
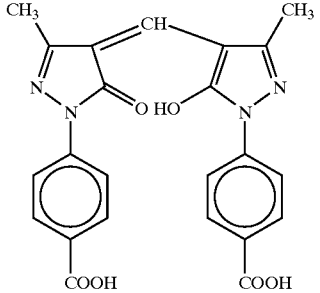
ExF-5
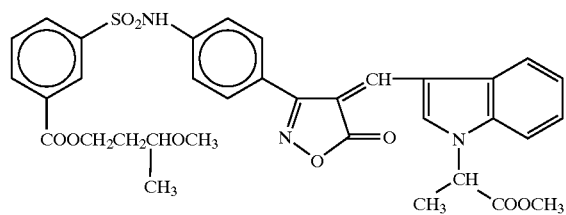
ExF-6

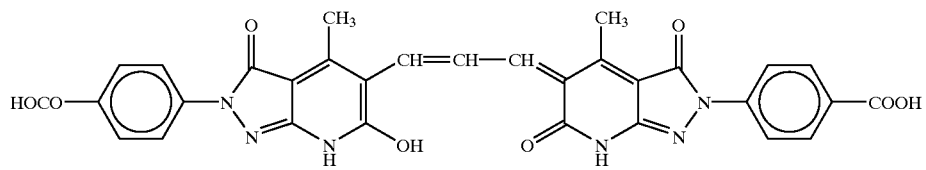

ExF-7

The thus-obtained silver halide color photographic light-sensitive material was designated as Sample N-1.

Sample N-1 was exposed for 1/100 seconds through a gelatin filter SC-39 produced by Fuji Photo Film Co., Ltd., and a continuous wedge.

(3) Development Processing

Using Mini-Lab Film Processor FP363SC manufactured by Fuji Photo Film Co., Ltd., a continuous processing (running test) was performed until the amount of the color developer replenisher used in the following processing step became 0.5 times the volume of the color developing tank.

| Processing Step | Temp-erature | Time | Replen-ishing Amount | Tank Volume |
|---|---|---|---|---|
| Color development | 38.0° C. | 3 min 5 sec | 15 mL | 10.3 L |
| Bleaching | 38.0° C. | 50 sec | 15 mL | 3.6 mL |
| Fixing (1) | 38.0° C. | 50 sec | — | 3.6 mL |
| Fixing (2) | 38.0° C. | 50 sec | 7.5 mL | 3.6 mL |
| Stabilization (1) | 38.0° C. | 20 sec | — | 1.9 mL |
| Stabilization (2) | 38.0° C. | 20 sec | — | 1.9 mL |
| Stabilization (3) | 38.0° C. | 20 sec | 30 mL | 1.9 mL |
| Drying | 60° C. | 1 min 30 sec | | |

*The replenishing amount was per 1.1 m of a 35 mm width light-sensitive (corresponding to one roll of 24 Ex.).

The stabilizing solutions flow in the countercurrent system of (3)→(2)→(1), and the fixing solutions are also connected by a countercurrent piping from (2) to (1). The tank solution of the stabilizing solution (2) is flown to the fixing solution (2) in an amount of 15 mL which corresponds to the replenishing amount. Furthermore, for the color developer, Color Developer (A) replenisher and Color Developer (B) replenisher according to the formulation shown below were replenished in an amount of 12 mL and 3 mL, respectively, totaling to 15 mL which corresponds to the replenishing amount. The amount of developer carried over to the bleaching step, the amount of bleaching solution carried over to the fixing step and the amount of fixing solution carried over to the water washing step were all 2.0 mL per 1.1 m of a 35 mm-width light-sensitive material. Each cross-over time was 6 seconds and this time is included in the processing time of the previous step.

| [Color Developer A] | [Tank Solution] | [Replenisher] |
|---|---|---|
| Water | 800 mL | 800 mL |
| Diethylenetriaminepentaacetic acid | 2.0 g | 4.0 g |
| Sodium 4,5-dihydroxybenzene-1,3-disulfonate | 0.4 g | 0.5 g |
| Disodium N,N-bis(sulfonato-ethyl) hydroxylamine | 10.0 g | 15.0 g |

-continued

| [Color Developer A] | [Tank Solution] | [Replenisher] |
|---|---|---|
| Sodium sulfite | 4.0 g | 9.0 g |
| Potassium bromide | 1.4 g | — |
| Diethylene glycol | 10.0 g | 17.0 g |
| Ethyleneurea | 3.0 g | 5.5 g |
| 2-Methyl-4-[N-ethyl-N-β-hydroxyethyl) aniline sulfate | 4.7 g | 11.0 g |
| Potassium carbonate | 39.0 g | 59.0 g |
| Water to make a total of | 1,000 mL | 1,000 mL |
| pH (at 25° C., adjusted by sulfuric acid and KOH) | 10.05 | 10.50 |

The tank solution above shows the composition of (Color Developer A) when mixed with the following (Color Developer B).

| [Color Developer B] | [Tank Solution] | [Replenisher] |
|---|---|---|
| Hydroxylamine sulfate | 2.0 g | 4.0 g |
| Water to make a total of | 1,000 mL | 1,000 mL |
| pH (at 25° C., adjusted by sulfuric acid and KOH) | 10.05 | 4.0 |

The tank solution above shows the composition of (Color Developer B) when mixed with (Color Developer A).

| [Bleaching Solution] | [Tank Solution] | [Replenisher] |
|---|---|---|
| Water | 800 mL | 800 mL |
| Fe (III) ammonium 1,3-diamino-propanetetraacetate monohydrate | 120 g | 180 g |
| Ammonium bromide | 50.0 g | 70.0 g |
| Succinic acid | 30.0 g | 50.0 g |
| Maleic acid | 40.0 g | 60.0 g |
| Imidazole | 20.0 g | 30.0 g |
| Water to make a total of | 1,000 mL | 1,000 mL |
| pH (at 25° C., adjusted by aqueous ammonia and nitric acid) | 4.60 | 4.00 |

| [Fixing Solution] | [Tank Solution] |
|---|---|
| Compound of the present invention | 2 mmol |
| Ammonium thiosulfate (750 g/L) | 280 mL |
| Aqueous ammonium bisulfite solution (72%) | 20.0 g |
| Imidazole | 35.0 g |
| Ethylenediaminetetraacetic acid | 8.0 g |
| Water to make a total of | 1,000 mL |
| pH (at 25° C., adjusted by aqueous ammonia and nitric acid) | 7.00 |

For the fixing replenisher, a solution obtained by 1.2-fold diluting the fixing composition prepared in (1) with water was used.

| [Stabilizing Solution] | [Tank solution and Replenisher are common] |
|---|---|
| Water | 800 mL |
| Sodium p-toluenesufinate | 0.03 g |
| p-Nonylphenylpolyglycidol (average polymerization degree of glycidol: 10) | 0.40 g |
| Disodium ethylenediaminetetraacetate | 0.05 g |
| 1,2,4-Triazole | 1.3 g |
| 1,4-Bis(1,2,4-triazol-1-ylmethyl)-piperazine | 0.75 g |
| 1,2-Benzoisothiazolin-3-one | 0.10 g |
| Water to make a total of | 1,000 mL |
| pH (at 25° C., adjusted by aqueous ammonia and nitric acid) | 7.00 |

(4) Evaluation

1) Stability against Deposition of Precipitates

The evaluation was performed in the same manner as in Example 1.

2) Photographic Properties in Processing of Color Negative Film

An unexposed light-sensitive material Sample N-1 was subjected to a development processing and the transmission absorption spectrum thereof was measured using a spectrophotometer (Model U-3500, manufactured by Hitachi Ltd.). The absorbancy at 540 nm was designated as $D_G$. Sample 29 without addition of compound was washed with distilled water at 30° C. for 3 minutes and dried. Thereafter, the sane measurement was performed and the absorbancy at 540 nm here was designated as $D_{G0}$.

$\Delta D_G$ was determined according to the following formula and from the obtained value, the degree of staining ascribable to the residual sensitizing dyes was evaluated.

$$\Delta D_G = D_G - D_{G0}$$

3) Results

TABLE 6

| Sample | Compound Added | Amount Added (mmol) | Evaluation of Deposition (−5° C.) | Evaluation of Deposition (room temperature) | Evaluation of Photographic Properties ($\Delta D_G$) | Remarks |
|---|---|---|---|---|---|---|
| 3-1 | none | — | OO | OO | 0.027 | Comparison |
| 3-2 | FL-2 | 5 | XX | X | 0.005 | Comparison |
| 3-3 | FL-3 | 5 | X | Δ | −0.004 | Comparison |
| 3-4 | A-2 | 5 | OO | OO | 0.003 | Invention |
| 3-5 | A-3 | 5 | OO | OO | 0.004 | Invention |
| 3-6 | A-7 | 5 | O | OO | −0.002 | Invention |
| 3-7 | A-23 | 5 | OO | OO | 0.004 | Invention |

Samples 3-2 and 3-3 (Comparison) using Compounds FL-2 and FL-3 are effective in reducing the staining ascribable to residual sensitizing dyes but in either case, precipitation is generated in aging of the processing composition. This precipitation is ascribable to the compound added, because in Sample 3-1 (comparison), precipitation does not occur.

In the light-sensitive material of which development processing is performed using the processing composition of the present invention, the staining ascribable to residual sensitizing dyes is effectively reduced. At the same time, the processing composition is completely transparent at room temperature after the passing of 4 weeks and even at a low temperature (−5° C.), the processing composition is completely transparent or slightly turbid and precipitation is not generated. From these results, it is verified that also when the processing composition of the present invention is used as a fixing composition, the composition provides an excellent effect of reducing the staining ascribable to residual sensitizing dyes of a light-sensitive material and can be free of deposition of precipitates during the storage of the processing composition at low temperatures.

EXAMPLE 4

(1) Preparation of Color Developing Composition

| Water | 800 mL |
|---|---|
| Compound ot the present invention | see Table 4 |
| Diethylenetriaminepentaacetic acid | 9.0 g |
| Sodium 4,5-dihydroxybenzene-1,3-disulfonate | 8.0 g |
| Disodium N,N-bis(sulfonatoethyl)-hydroxylamnine | 12.0 g |
| Sodium sulfite | 14.0 g |
| Diethylene glycol | 22.5 g |
| Ethyleneurea | 7.5 g |
| 4-Amino-3-methyl-N-ethyl-N-(β-hydroxyethyl)aniline sulfate | 15.0 g |
| Potassium carbonate | 100 g |
| Water to make a total of | 1,000 mL |
| pH (at 25° C., adjusted by sulfuric acid and KOH) | 12.25 |

(2) Light-Sensitive Material

The same sample as in Example 3 was used.

(3) Development Processing

Using an experimental processing apparatus obtained by modifying Mini-Lab Printer Processor FP363SC manufactured by Fuji Photo Film Co., Ltd. so that the processing time and the processing temperature could be varied, a continuous processing (running test) was performed until the amount of the color developer replenisher used in the following processing step became 0.5 times the volume of the color developing tank.

| Processing Step | Temperature | Time | Replenishing Amount | Tank Volume |
|---|---|---|---|---|
| Color development | 41.0° C. | 2 min 00 sec | 125 mL | 10.3 L |
| Bleaching | 41.0° C. | 20 sec | 5 mL | 3.6 mL |
| Fixing (1) | 41.0° C. | 20 sec | — | 3.6 ml |
| Fixing (2) | 41.0° C. | 20 sec | 7.5 mL | 3.6 mL |
| Stabilization (1) | 41.0° C. | 130 sec | — | 1.9 mL |
| Stabilization (2) | 41.0° C. | 13 sec | — | 1.9 mL |
| Stabilization (3) | 41.0° C. | 14 sec | 25 mL | 1.9 mL |
| Drying | 60° C. | 30 sec | | |

* The replenishing amount was per 1.1 m of a 35 mm-width light-sensitive material (corresponding to one roll of 24 Ex.).

The stabilizing solutions flow in the countercurrent system of (3)→(2)→(1), and the fixing solutions are also connected by a countercurrent piping from (2) to (1). The tank solution of the stabilizing solution (2) is flown to the fixing solution (2) in an amount of 15 mL which corresponds to the replenishing amount. Furthermore, for the color developer, Color Developer (A) replenisher and Color Developer (B) replenisher according to the formulation shown below were replenished 12 mL and 3 mL, respectively, totaling to 15 mL which corresponds to the replenishing amount. The amount or developer carried over to the bleaching step, the amount of bleaching solution carried over to the fixing step and the amount of fixing solution carried over to the water washing step were all 2.0 mL per 1.1 m of a 35 =m-width light-sensitive material. Each cross-over time was 6 seconds and this time is included in the processing time of the previous step.

| [Color Developer A] | [Tank Solution] |
|---|---|
| Water | 800 mL |
| Compound of the present invention | 4 mmol |
| Diethylenetriaminepentaacetic acid | 2.0 g |
| Sodium 4,5-dihydroxybenzene-1,3-disulfonate | 0.4 g |
| Disodium N,N-bis(sulfonatoethyl)-hydroxylamine | 10.0 g |
| Sodium sulfite | 4.0 g |
| Potassium bromide | 1.4 g |
| Diethylene glycol | 10.0 g |
| Ethyleneurea | 3.0 g |
| 4-Amino-3-methyl-[N-ethyl-N-(β-hydroxyethyl) aniline sulfate | 5.7 g |
| Potassium carbonate | 39.0 g |
| Water to make a total of | 1,000 mL |
| pH (at 25° C., adjusted by sulfuric acid and KOH) | 10.05 |

The tank solution above shows the composition of (Color Developer A) when mixed with the following (Color Developer B).

For the Color Developer A replenisher, a solution obtained by 2.1-fold diluting the color developing composition prepared in (1) with water was used.

| [Color Developer B] | [Tank Solution] | [Replenisher] |
|---|---|---|
| Hydroxylamine sulfate | 2.0 g | 4.0 g |
| Water to make a total of | 1,000 mL | 1,000 mL |
| pH (at 25° C., adjusted by sulfuric acid and KOH) | 10.10 | 4.0 |

| [Bleaching Solution] | [Tank Solution] | [Replenisher] |
|---|---|---|
| Water | 800 mL | 800 mL |
| Fe(III) ammonium 1,3-diaminopropanetetraacetate monohydrate | 150 g | 200 g |
| Ammonium bromide | 50.0 g | 70.0 g |
| Succinic acid | 50.0 g | 80.0 g |
| Imidazole | 50.0 g | 80.0 g |
| Water to make a total of | 1,000 mL | 1,000 mL |
| pH (at 25° C., adjusted by aqueous ammonia and nitric acid) | 4.20 | 3.80 |

| [Fixing Solution] | [Tank Solution] | [Replenisher] |
|---|---|---|
| Ammonium thiosulfate (750 g/L) | 280 mL | 745 mL |
| Aqueous ammonium bisulfite solution (72%) | 20.0 g | 80.0 g |
| Imidazole | 12.0 g | 35.0 g |
| 1-Mercapto-2-(N,N-dimethylaminoethyl)tetrazole | 0.6 g | 1.8 g |
| Ethylenediaminetetraacetic acid | 3.0 g | 9.0 g |
| Water to make a total of | 1,000 mL | 1,000 mL |
| pH (at 25° C., adjusted by aqueous ammonia and nitric acid) | 7.00 | 7.00 |

| [Stabilizing Solution] | [Tank solution and Replenisher are common] |
|---|---|
| Water | 800 mL |
| Sodium p-toluenesufinate | 0.03 g |
| p-Nonylphenylpolyglycidol (average polymerization degree of glycidol: 10) | 0.40 g |
| Disodium ethylenediaminetetraacetate | 0.05 g |
| 1,2,4-Triazole | 1.3 g |
| 1,4-Bis(1,2,4-triazol-1-ylmethyl)-piperazine | 0.75 g |
| 1,2-Benzoisothiazolin-3-one | 0.10 g |
| Water to make a total of | 1,000 mL |
| pH (at 25° C., adjusted by aqueous ammonia and nitric acid) | 7.00 |

(4) Evaluation
  1) Stability against Deposition of Precipitates
  The evaluation was performed in the same manner as in Example 1.
  2) Photographic Properties in Processing of Color Negative Film
  An unexposed sample (Light-Sensitive Material Sample N-1) was subjected to a development processing and the transmission absorption spectrum thereof was measured using a spectrophotometer (Model U-3500, manufactured by Hitachi Ltd.). The absorbancy at 540 nm was designated as $D_G$. Sample 37 without addition of compound was washed with distilled water at 30° C. for 3 minutes and dried. Thereafter, the same measurement was performed and the absorbancy at 540 nm here was designated as $D_{G0}$. $\Delta D_G$ was determined according to the following formula and from the obtained value, the staining ascribable to the residual sensitizing dyes was evaluated.

$$\Delta D_G = D_G - D_{G0}$$

3) Results

TABLE 7

| Sample | Compound Added | Amount Added (mmol) | Evaluation of Deposition (−5° C.) | Evaluation of Deposition (room temperature) | Evaluation of Photographic Properties ($\Delta D_G$) | Remarks |
|---|---|---|---|---|---|---|
| 4-1 | none | — | OO | OO | 0.045 | Comparison |
| 4-2 | FL-2 | 15 | XX | X | 0.003 | Comparison |
| 4-3 | FL-3 | 15 | X | Δ | −0.006 | Comparison |
| 4-4 | A-2 | 15 | OO | OO | 0.000 | Invention |
| 4-5 | A-3 | 15 | OO | OO | 0.003 | Invention |
| 4-6 | A-7 | 15 | O | OO | −0.004 | Invention |
| 4-7 | A-23 | 15 | OO | OO | −0.002 | Invention |

Samples 4-2 and 4-3 (Comparison) using Compounds FL-2 and FL-3 are effective in reducing the staining ascribable to residual sensitizing dyes but in either case, precipitation is generated in aging of the processing composition. This precipitation is ascribable to the compound added, because in Sample 4-1 (comparison), precipitation does not occur.

In the light-sensitive material of which development processing is performed using the processing composition of the present invention, the staining ascribable to residual sensitizing dyes is effectively reduced. At the same time, the processing composition is completely transparent at room temperature after the passing of 4 weeks and even at a low temperature (−5° C.), the processing composition is completely transparent or slightly turbid and precipitation is not generated. From these results, it is verified that when a color negative film is processed within a shortened processing time using the color developing composition of the present inventions the composition provides an excellent effect of reducing the staining ascribable to residual sensitizing dyes of a light-sensitive material and can be free of deposition of precipitates during the storage of the processing composition at low temperatures.

EXAMPLE 5
(1) Preparation of Additive Composition

An additive composition for the addition to a fixing solution was prepared as shown in Table 8.

TABLE 8

| Sample | Compound Added and Amount Added (mmol) | | Dissolution Aid and Amount Added (mol) | | Solubility at the Preparation of Solution | Evaluation of Deposition (−5° C.) | Remarks |
|---|---|---|---|---|---|---|---|
| 5-1 | FL-6 | 70 | none | — | Suspended | not evaluated | Comparison |
| 5-2 | FL-6 | 70 | DEG | 3 | Suspended | not evaluated | Comparison |
| 5-3 | FL-6 | 70 | DEG | 8 | Completely dissolved | OO | Comparison |
| 5-4 | A-2 | 70 | none | — | Completely dissolved | OO | Invention |
| 5-5 | A-3 | 70 | none | — | Completely dissolved | OO | Invention |
| 5-6 | A-3 | 140 | none | — | Completely dissolved | OO | Invention |
| 5-7 | A-34 | 70 | none | — | Completely dissolved | OO | Invention |

*In Table 8, DEG indicates diethylene glycol.

FL-6

An about 1:2:1 (by mol) mixture of the following compounds α, β and γ.

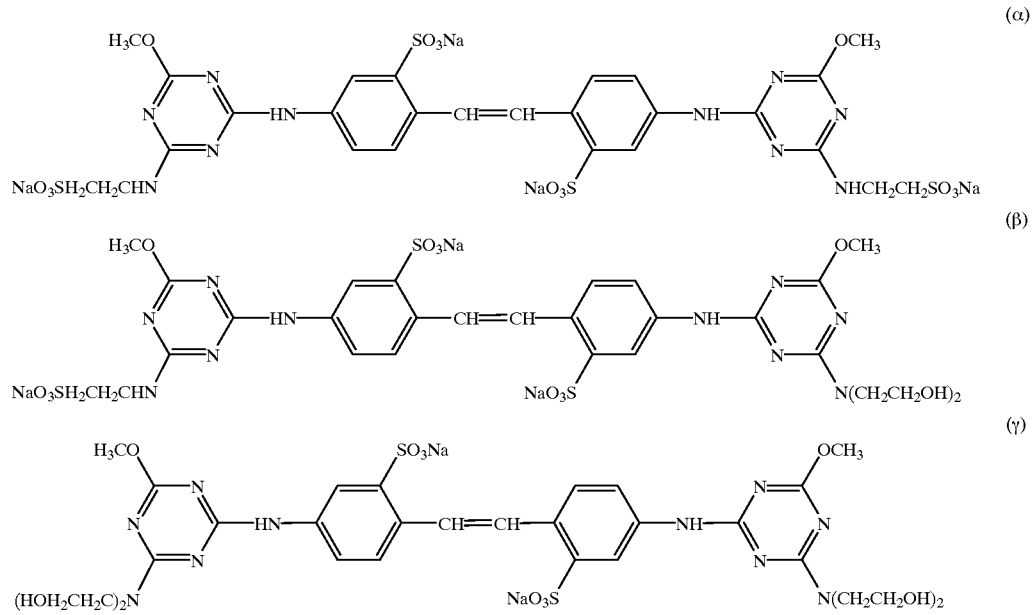

(2) Light-Sensitive Material Sample

The following commercially available color reversal films were used.

Sample A: Fujichrome Provia, produced by Fuji Photo Film Co., Ltd. (Serial No. 156004)

Sample B: Ectachrome E-100S, produced by Eastman Kodak (Serial No. 1411)

(1) Development Processing

The above-descried light-sensitive samples, which were gray exposed to an average density, were subjected to a continuous processing (running test) until the first black-and-white developer in the following processing step became 0.5 round. Sample A and Sample B were used at a ratio of 4:1. The development processing was performed by employing a system of transporting a sample while hooking it on a hanger.

| Processing Step | Temperature | Time | Tank Volume | Replenishing Amount* |
| --- | --- | --- | --- | --- |
| First black-and-white development | 38.0° C. | 6 min | 12 L | 2200 mL |
| First water washing | 38.0° C. | 2 min | 4 L | 7500 mL |
| Reversal | 38.0° C. | 2 min | 4 L | 1100 mL |
| Color development | 38.0° C. | 6 min | 12 L | 2200 mL |
| Pre-bleaching | 38.0° C. | 2 min | 4 L | 1100 mL |
| Bleaching | 38.0° C. | 6 min | 2 L | 220 mL |
| Fixing | 38.0° C. | 4 min | 8 L | 1100 mL |
| Second water washing | 38.0° C. | 6 min | 8 L | 7500 mL |
| Final rinsing | 25.0° C. | 1 min | 2 L | 1100 mL |

(Note)
*The replenishing amount was per 1 m² of light-sensitive material.

Each processing solution had the following composition.

| [First Black-and-White Developer] | [Tank Solution] | [Replenisher] |
| --- | --- | --- |
| Pentasodium nitrilo-N,N,N-trimethylenephosphonate | 1.5 g | 1.5 g |
| Pentasodium salt diethylenetriaminepentaacetate | 2.0 g | 2.0 g |
| Sodium sulfite | 30 g | 30 g |
| Potassium hydroquinone monosulfonate | 15 g | 20 g |
| Sodium bicarbonate | 12 g | 15 g |
| 1-Phenyl-4-methyl-4-hydroxymethyl-3-pyrazolidone | 1.5 g | 2.0 g |
| Potassium bromide | 2.5 g | 1.4 g |
| Potassium thiocyanate | 1.2 g | 1.2 g |
| Potassium iodide | 2.0 mg | — |
| Diethylene glycol | 13 g | 15 g |
| Water to make a total of | 1,000 mL | 1,000 mL |
| pH (at 25° C., adjusted by sulfuric acid and KOH) | 9.60 | 9.60 |

| [Reversal Solution] | [Tank Solution] | [Replenisher] |
| --- | --- | --- |
| Pentasodium nitrilo-N,N,N-trimethylenephosphonate | 3.0 g | Same as the tank solution |
| Stannous chloride dihydrate | 1.0 g | |
| p-Aminophenol | 0.1 g | |
| Sodium hydroxide | 8 g | |
| Propionic acid | 15 mL | |
| Water to make a total of | 1,000 mL | |
| pH (at 25° C., adjusted by acetic acid and KOH) | 6.00 | |

| [Color Developer] | [Tank Solution] | [Replenisher] |
| --- | --- | --- |
| Pentasodium nitrilo-N,N,N-trimethylenephosphonate | 2.0 g | 2.0 g |
| Sodium sulfite | 7.0 g | 7.0 g |
| Trisodium phosphate dodecahydrate | 36 g | 36 g |
| Sodium bromide | 0.7 g | — |
| Potassium iodide | 40 mg | — |
| Sodium hydroxide | 3.0 g | 3.0 g |
| Citrazinic acid | 0.5 g | 0.5 g |
| N-ethyl-N-β-methanesulfonamidoethyl)-3-methyl-4-aminoaniline 3/2 sulfate monohydrate | 11 g | 11 g |
| 3,6-Dithiaoctane-1,8-diol | 1.0 g | 1.0 g |
| Water to make a total of | 1,000 mL | 1,000 mL |
| pH (at 25° C., adjusted by sulfuric acid and KOH) | 11.80 | 12.00 |

| [Pre-bleaching] | [Tank Solution] | [Replenisher] |
| --- | --- | --- |
| Disodium ethylenediaminetetraacetate dihydrate | 8.0 g | 8.0 g |
| Sodium sulfite | 6.0 g | 8.0 g |
| 1-Thioglycerol | 0.4 g | 0.4 g |
| Formaldehyde/sodium bisulfite adduct | 20 g | 25 g |
| Methanol | 2 g | 2 g |
| Water to make a total | 1,000 mL | 1,000 mL |
| pH (at 25° C., adjusted by acetic acid and NaOH) | 6.30 | 6.10 |

| [Bleaching Solution] | [Tank Solution] | [Replenisher] |
| --- | --- | --- |
| Disodium ethylenediaminetetraacetate dihydrate | 2.0 g | 4.0 g |
| Fe(III) ammonium ethylenediaminetetraacetate dihydrate | 120 g | 240 g |
| Potassium bromide | 100 g | 200 g |
| Ammonium nitrate | 10 g | 20 g |
| Water to make a total of | 1,000 mL | 1,000 mL |
| pH (at 25° C., adjusted by nitric acid and NaOH) | 5.70 | 5.50 |

| [Fixing Solution] | [Tank Solution] | [Replenisher] |
| --- | --- | --- |
| Additive composition shown in Table 8 or no addition | 1 mL | Same as the tank solution |
| Ammonium thiosulfate | 80 g | |
| Sodium sulfite | 5.0 g | |
| Sodium bisulfite | 5.0 g | |
| Water to make a total of | 1,000 mL | |
| pH (at 25° C., adjusted by acetic acid and aqueous ammonia) | 6.60 | |

| [Stabilizing Solution] | [Tank Solution] | [Replenisher] |
| --- | --- | --- |
| 2-Benzoisothiazolon-3-one | 0.02 g | same as the tank solution |
| Dipropylene glycol | 0.3 g | |
| Organic silicon surfactant | 0.2 g | |
| Water to make a total of | 1,000 mL | |
| pH (at 25° C.) | 7.0 | |

(4) Evaluation
1) Stability against Deposition of Precipitates

The same evaluation as in Example 1 was performed only at −5° C.

Samples 5-1 and 5-2 became a suspension at the preparation of composition and therefore, evaluation therefor was not performed.

2) Photographic Properties in Processing of Color Reversal Film

A tank solution and a replenisher for use in the fixing step were prepared by adding 1 mL of the additive composition per 1 L of the tank solution and per 1 L of the replenisher and using these, a continuous processing was performed. Thereafter, an unexposed light-sensitive material sample was subjected to a development processing and the transmission absorption spectrum thereof was measured using a spectrophotometer (Model U-3500, manufactured by Hitachi Ltd.). The absorbancy at 570 nm of this sample was designated as $D_G$. Separately, a continuous processing was performed using an addition-free fixing solution and the same development processing and measurement of absorption spectrum were performed. The absorbency at 570 nm of the light-sensitive material sample here was designated as $D_{G0}$. $\Delta D_G$ was determined according to the following formula and from the obtained value, the effect of reducing staining ascribable to the residual sensitizing dyes, which was provided by the additive composition for the fixing solution, was evaluated.

$$\Delta D_G = D_G - D_{G0}$$

After the completion of continuous processing, the processing step was stopped for 60 hours and again the development processing was performed. Using the obtained light-sensitive material, the absorption spectrum thereof was measured in the same manner and then, the effect of reducing staining was evaluated.

TABLE 9

| Light-Sensitive Material Sample | Sample | Photographic Properties at Continuous Processing ($\Delta D_G$) | Photographic Properties at Restarting of Processing ($\Delta D_G$) | Remarks |
|---|---|---|---|---|
| Fujichrome Provia | 5-3 | −0.007 | −0.001 | Comparison |
| | 5-4 | −0.005 | −0.004 | Invention |
| | 5-5 | −0.004 | −0.003 | Invention |
| | 5-6 | −0.007 | −0.006 | Invention |
| | 5-7 | −0.007 | −0.006 | Invention |
| Ectachrome E-100s | 5-3 | −0.015 | −0.004 | Comparison |
| | 5-4 | −0.009 | −0.008 | Invention |
| | 5-5 | −0.007 | −0.007 | Invention |
| | 5-6 | −0.014 | −0.013 | Invention |
| | 5-7 | −0.008 | −0.007 | Invention |

In Table 8, when Compound FL-6 is used, the solubility of compound is low and for obtaining a uniform composition, 100 equivalents or more of diethylene glycol must be used as a dissolution aid, like Sample 5-3 (Comparison). The compound of the present invention can provide a uniform additive composition without using a dissolution aid and at the same time, this composition is stable in the low-temperature storage and generates no deposit or precipitate.

As seen from Table 9, in the case of using Sample 5-3 (comparison), when a continuous processing is stopped for a predetermine time and then the processing is restarted, the effect of reducing staining decreases. On the other hand, when the additive composition of the present invention is used, the effect of reducing staining does not lower even after stopping and then restarting a continuous processing and stable photographic performance free of change in the minimum density can be attained.

By performing the development processing using a processing agent composition of the present invention containing a bistriazinyl arylenediamine derivative, not only in a normal processing but also in a rapid processing, coloration due to residual sensitizing dyes does not occur, and the staining in the highlight are can be suppressed to a low level. At the same time, this compound has high solubility in the composition and therefore, the processing composition can be stably stored without causing deposition of precipitates during the storage.

Furthermore, when this compound is used in combination with a fluorescent whitening agent, the fluorescent whitening effect and the effect of preventing coloration staining can be independently controlled, The above-described effects can be obtained not only when the compound is added to a color developing solution but also when used in other processing compositions such as fixing composition and bleaching composition.

The entire disclosure of each and every foreign patent application from which the benefit of foreign priority has been claimed in the present application is incorporated herein by reference, as if fully set forth herein.

What is claimed is:

1. A processing composition for a silver halide photographic material, which comprises a compound represented by the following formula (I):

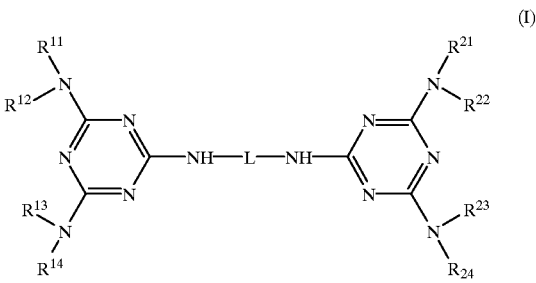

wherein $R^{11}$, $R^{12}$, $R^{13}$, $R^{14}$, $R^{21}$, $R^{22}$, $R^{23}$ and $R^{24}$ each represents a hydrogen atom, an alkyl group, an aryl group or a heterocyclic group; L represents a phenylene group or a naphthylene group; each of pairs $R^{11}$ and $R^{12}$, $R^{13}$ and $R^{14}$, $R^{21}$ and $R^{22}$, and $R^{23}$ and $R^{24}$ may be combined with each other to form a ring; the compound contains at least one group represented by —SO$_3$M, —CO$_2$M or —OH in the molecule, wherein M represents a hydrogen atom, an alkali metal, an alkaline earth metal, ammonium or pyridinium; with the proviso that the case where three or more of $R^{11}$, $R^{12}$, $R^{13}$, $R^{14}$, $R^{21}$, $R^{22}$, $R^{23}$ and $R^{24}$ are an aryl group is excluded; with the proviso that the case where at least one of $R^{11}$, $R^{12}$, $R^{13}$ and $R^{14}$ are combined with at least one of $R^{21}$, $R^{22}$, $R^{23}$ and $R^{24}$ to form a ring is excluded; and with the proviso that the compound does not contain a group represented by —N=N— in the molecule.

2. The processing composition according to claim 1, wherein $R^{11}$, $R^{12}$, $R^{13}$, $R^{14}$, $R^{21}$, $R^{22}$, $R^{23}$ and $R^{24}$ each independently represents a hydrogen atom, an alkyl group or an aryl group.

3. The processing composition according to claim 1, wherein $R^{11}$, $R^{12}$, $R^{13}$, $R^{14}$, $R^{21}$, $R^{22}$, $R^{23}$ and $R^{24}$ each independently represents a hydrogen atom, a methyl group, an ethyl group, an n-propyl group, a sulfomethyl group, a 2-hydroxyethyl group, a 3-hydroxypropyl group, a 2-hydroxypropyl group, a 2-sulfoethyl group, a 2-methoxyethyl group, 2-(2-hydroxyethoxy)ethyl group, a 2-[2-(2-hydroxyethoxy)ethoxy]ethyl group, a 2,3-dihydroxypropyl group, a 3,4-dihydroxybutyl group, a phenyl group, a 3-carboxyphenyl group, a 4-carboxyphenyl group, a 3,5-dicarboxyphenyl group, a 4-methoxyphenyl group, a 2-sulfophenyl group or a 4-sulfophenyl group.

4. The processing composition according to claim 1, wherein L is a substituted or unsubstituted phenylene or naphthylene group having 6 to 20 carbon atoms.

5. The processing composition according to claim 1, wherein L represents 1,4-phenylene, 1,3-phenylene, 1,2-phenylene, 1,5-naphthylene, 1,8-naphthylene, 4-carboxy-1,2-phenylene, 5-carboxy-1,3-phenylene, 3-sulfo-1,4-phenylene, 5-sulfo-1,3-phenylene, 2,5-dimethoxy-1,4-phenylene or 2,6-dichloro-1,4-phenylene.

6. The processing composition according to claim 1, wherein the ring formed by combining each of pairs $R^{11}$ and $R^{12}$, $R^{13}$ and $R^{14}$, $R^{21}$ and $R^{22}$, and $R^{23}$ and $R^{24}$ is a 5- or 6-membered ring.

7. The processing composition according to claim 1, wherein the ring formed by each pair $R^{11}$ and $R^{12}$, $R^{13}$ and $R^{14}$, $R^{21}$ and $R^{22}$, or $R^{23}$ and $R^{24}$ combined with each other is a pyrrolidine ring, a piperidine ring, a piperazine ring or a morpholine ring.

8. The processing composition according to claim 1, which further comprises a bis(triazinylamino)stilbene disulfonic acid compound.

9. The processing composition according to claim 1, wherein the concentration of the compound of formula (I) is from 0.05 to 20 mmol/L in a working solution.

10. The processing composition according to claim 1, which is a color developing composition, a bleaching composition, a bleach-fixing composition, a fixing composition, a water washing composition, a stabilizing composition, or an additive composition.

11. An image formation method comprising processing a silver halide photographic material with a processing composition for a silver halide photographic material according to claim 1.

12. The image formation method according to claim 10, wherein the silver halide photographic material is a color paper obtained by coating on a support a high silver chloride emulsion containing at least 90 mol % or more of silver chloride.

13. The image formation method according to claim 10, wherein the silver halide photographic material is a color negative film or color reversal film obtained by coating on a support a high silver bromide emulsion containing at least 50 mol % or more of silver bromide.

* * * * *